United States Patent
Sugawara et al.

(10) Patent No.: US 6,458,347 B1
(45) Date of Patent: Oct. 1, 2002

(54) DRUG COMPLEX

(75) Inventors: Shuichi Sugawara; Masahiro Kajiki; Hiroshi Kuriyama; Nobuya Kitaguchi, all of Fuji (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 0 days.

(21) Appl. No.: 09/172,085

(22) Filed: Oct. 14, 1998

Related U.S. Application Data

(63) Continuation-in-part of application No. PCT/JP97/01303, filed on Apr. 15, 1997.

(30) Foreign Application Priority Data

Apr. 15, 1996 (JP) .............................................. 8-115257
Nov. 22, 1996 (JP) .............................................. 8-325880

(51) Int. Cl.$^7$ ...................... A61K 31/77; A61K 31/721; A61K 31/337; A61K 38/06; A61K 38/08

(52) U.S. Cl. .................... 424/78.17; 424/78.3; 514/449; 514/59; 514/17; 514/18; 514/2; 514/169

(58) Field of Search .............................. 424/486, 78.17, 424/78.3; 514/59, 17, 18, 449, 2, 169

(56) References Cited

U.S. PATENT DOCUMENTS

| 5,037,883 A | 8/1991 | Kopecek et al. |
| 5,362,831 A | 11/1994 | Mongelli et al. |
| 5,646,176 A | 7/1997 | Golik et al. |
| 5,648,506 A * | 7/1997 | Desai et al. |
| 5,688,931 A | 11/1997 | Nogusa et al. |

FOREIGN PATENT DOCUMENTS

| EP | 0 624 377 | 11/1994 |
| JP | 60-67503 | 4/1985 |
| JP | 6-293665 | 10/1994 |
| WO | WO 93/24476 | 12/1993 |
| WO | WO 95/11020 | 4/1995 |

OTHER PUBLICATIONS

K.C. Nicolaou et al., "Design, synthesis and biological activity of protaxols", pp. 464–466, Nature, vol. 364, Jul. 29, 1993.

H. Sezaki, "Drug Delivery System", with partial translation, pp. 46–63, Nankodo, Japan.

R. Duncan et al., "Anticancer Agents Coupled to N–(2–Hydroxypropyl) Methacrylamide Copolymers. 3. Evaluation of Adriamycin conjugates Against Mouse Leukaemia L1210 In Vivo", pp. 51–63, Journal of Controlled Release, No. 10, 1989.

(List continued on next page.)

Primary Examiner—Edward J. Webman
(74) Attorney, Agent, or Firm—Young & Thompson

(57) ABSTRACT

Disclosed is a drug complex of a drug having a hydroxyl group, which is capable of controlling the rate of the release of the drug therefrom in blood, the drug complex being represented by the following formula (1):

A—B—C (1)

wherein A represents at least one carrier selected from the group consisting of saccharides each having a carboxyl group, polyethylene glycols each having a carboxyl group, aliphatic carboxylic acids each having a carboxyl group, and derivatives thereof each having a carboxyl group; B represents at least one spacer comprised of a compound having a amino group and a carboxyl group; C represents at least one drug having a hydroxyl group, wherein the carrier A is bonded to the spacer B through an amide bond formed between the carboxyl group of the carrier A and the amino group of the spacer B; and the spacer B is bonded to the drug C through an ester bond formed between the carboxyl group of the spacer B and the hydroxyl group of the drug C.

28 Claims, 27 Drawing Sheets

Release of drug in mouse serum

OTHER PUBLICATIONS

R. Duncan et al., "Preclinical evaluation of polymer–bound doxorubicin", pp. 331–346, Journal of Controlled Release, No. 19, 1992.

F. Eckhardt, et al., "A Phase I and Bioavailability Study of Oral Topotecan", p. S193, Eur. J. Caner, 31A (Suppl. 5), Nov. 1, 1995.

R.B. Greenwald et al., "Highly Water Soluble Taxol Derivatives: 2' –Polyethyeneglycol Esters As Potential Prodrugs", pp. 2465–2470, Bioorganic & Medicinal Chemistry Letters, vol. 4, No. 20, 1994.

H. Susaki et al., "Synthesis of Artificial Glycoconjugates of Argninine–Vasopressin and Their Antidiuretic Activities", pp. 2090–2096, Chem. Pharm. Bull., vol. 42, No. 10, 1994.

R.B. Greenward et al., "Drug Delivery System 2. Campto–thecin 20–0–Poly (ethylene glycol) Ester Transport Forms", pp. 1938–1940, J. Med. Chem. vol. 39, 1996.

C. Hansch et al., "Exploring QSAR Fundamentals and Applications in Chemistry and Biology", pp. pp. 69–96, The American Chemical Society, 1995.

F.M. Veronase et al., "Preparation, Physico–Chemical and Pharmacokinetic Characterization of Monomethoxypoly (Eth–ylene Glycol) –Derivatized Supperoxide Dismutase", pp. 145–154, Journal of Controlled Release, No. 10, 1989.

H. Gehrhardt et al., "Soluble polymers in organic chemistry", pp. 487–493, Polymer Bulletin No. 18, 1987.

H. Mase et al., "Determination of New Anticancer Drug, Paclitaxel, in Biological Fluids by High Performance Liquid Chromatography", with Partial Translation, pp. 351–355, Yakugaku Zasshi, vol. 114, 1994.

* cited by examiner

Release of drug in mouse serum

Release of drug in mouse serum

Release of drug in human serum

DRUG COMPLEX

This application is a continuation-in-part of PCT Application No. PCT/JP97/01303, filed on Apr. 15, 1997, which designated the United States and on which priority is claimed under 35 U.S.C. §120.

BACKGROUND OF THE INVENTION

1. Field of the Invention

The present invention relates to a drug complex of a drug having a hydroxyl group, wherein the drug complex is capable of controlling the rate of the release of the drug therefrom in blood when administered to a living body. The present invention also relates to a novel polysaccharide-taxane complex which is capable of not only obviating the defect (poor water-solubility) of a drug, for example, a taxane compound which is useful as an antitumor drug, but also delaying the disappearance of the taxane compound from blood and also enhancing the transferability of the taxane compound to tumor tissues.

2. Prior Art

Paclitaxel (tradename: Taxol; manufactured and sold by Bristol-Myers Squibb, U.S.A.) is a naturally occurring product, which is extracted from the bark of a taxaceous tree, *Taxus brevifolia,* native to Pacific-rim countries, and has been confirmed to have excellent antitumor activities by assays using animal models. In recent studies, it has been reported that the antitumor activities of paclitaxel is due to a specific mechanism involving the induction of abnormal polymerization of tubulin and the inhibition of mitosis. Further, in recent years, promising results have been obtained in the studies with respect to the antitumor activities of paclitaxel against various types of tumors, such as oophoroma, mastocarcinoma, carcinoma of colon and rectum, and lung cancer. A semi-synthesized homologue of paclitaxel, called docetaxel (tradename: Taxotere; manufactured and sold by Rhône-Poulenc Rorer Pharmaceuticals Limited, U.S.A./France), has also been found to have good antitumor activities.

One of the defects of taxane compounds, a representative example of which is paclitaxel, is poor solubility in water. Therefore, paclitaxel needs to be formulated into a pharmaceutical composition by use of a non-aqueous adjuvant for dissolving medicines. One of the dissolving adjuvants, which are currently used, is Cremophor EL (manufactured and sold by Sigma, U.S.A.). However, Cremophor EL itself may cause undesirable adverse side effects, such as anaphylaxis in human. For that reason, a lot of researches have been made with respect to water-soluble derivatives of paclitaxel. For example, the technique of using phosphonooxymethyl ether derivatives of taxane compounds [Unexamined Japanese Patent Application Laid-Open Specification (Japanese Kokai) No. 7-149779] and the technique of using carbonate type and ester type pro-drugs of taxane compounds having a leaving moiety which can be removed under basic conditions [Nature, 365, 464–466 (1993)] are known. However, satisfactory techniques have not yet been developed with respect to prodrugs of taxane compounds.

In the techniques to improve various defects of a drug by chemically modifying the molecular structure of the drug, the effectiveness of the prodrug comprising a drug having bonded thereto a leaving moiety depends heavily on the selection of the mode of a bonding between the drug and the leaving moiety [see "Doraggu Deribarii Sisutemu" (Drug Delivery System), edited by Hitoshi Sezaki and published by Nankodo, Japan]. In general, when it is intended to restore a drug from a prodrug by utilizing an enzymatic reaction, the types of enzymes distributed broadly in a living body, such as an esterase, an amidase and a carbamidase, will be determining factors for selecting the appropriate bonding mode. Therefore, when the drug has a hydroxyl group, the bonding mode is frequently selected among a carboxylic ester bond, a phosphoric ester bond and an acyloxymethyl ether bond, and when the drug has a carboxyl group, the bonding mode is frequently selected between an ester and an amide bond.

On the other hand, in general, high molecular weight compounds exhibit various unique properties and functions and, therefore, interact with a living body in manners which are largely different from the manners in which low molecular weight compounds interact with a living body. Therefore, a large number of attempts have been made, in which a drug having a low molecular weight is bonded to a high molecular weight compound as a leaving moiety to thereby produce a prodrug and the prodrug is used so as to control the behavior of the drug in a living body and the interactions between the drug and cells. Also in this case, the selection of the mode of a bonding between the drug and the high molecular weight compound is an important factor of determining the effectiveness of the prodrug. Usually, in a prodrug comprising a drug having bonded thereto a leaving moiety, the functional group of the drug is directly bonded to the functional group of the leaving moiety. It is still rare that a prodrug is constructed such that the drug is bonded to the leaving moiety through a spacer.

With respect to examples of such prodrugs comprising a drug, a spacer and a leaving moiety, although the number of examples thereof is small, there can be mentioned an example in which a carboxymethylated dextran (carboxymethyldextran), which is a high molecular-weight polysaccharide, is used as a carrier. In this example of prodrug, doxorubicin having an amino group in the structure thereof is used as a drug, wherein a carboxymethyl dextran is introduced into the amino group of doxorubicin through the spacer (see, International Application Publication No. WO 94/19376). As mentioned above, doxorubicin has an amino group in the structure thereof. In this technique, a peptide is used as a spacer. Therefore, each of the mode of the bonding formed between the amino group of the spacer and the carboxyl group of the carboxymethyldextran and the mode of the bonding formed between the carboxyl group of the spacer and the amino group of the drug is an amide bond. However, an amide bond is extremely stable in blood and, therefore, the rate of the release of the drug from the drug complex (prodrug) is very low in blood. Further, it is noted that, in this WO publication, there is no description with respect to the release of a drug having a hydroxyl group.

As examples of prodrugs containing a synthetic polymer as a carrier, there can be mentioned prodrugs comprising doxorubicin as a drug, in which a high molecular weight compound (HPMA) (which is a product of copolymerization of a plurality of hydroxypropyl methacrylamide derivatives) is bonded to doxorubicin at the amino group thereof through a peptide as a spacer [see, J. Contr. Rel., 10, 51–63 (1989), J. Contr. Rel., 19, 331–346 (1992), Eur. J. Cancer, 31A (suppl 5), S193 (1995)]. In these examples also, each of the mode of each of the bonding between the drug and the spacer and the mode of the bonding between the spacer and the carrier is an amide bond. Further, as mentioned above, the carrier is a synthetic polymer. Therefore, it is predicted that the carrier would not be degraded (metabolized) at all in a living body. As a result, when a drug complex (prodrug) containing the above-mentioned synthetic polymer as a carrier is administered to a living body, there is a danger of the accumulation of the toxicity and antigenicity of the carrier because the carrier stays as a foreign substance in a living body for a long period of time. Therefore, the molecular weight of the carrier should be controlled to a level such that the carrier is not accumulated in a living body, but can be excreted rapidly.

As another example of a prodrug containing, as a carrier, a synthetic polymer produced in substantially the same manner as mentioned above, there can be mentioned a prodrug comprising paclitaxel (a drug having hydroxyl groups) as a drug, in which a high molecular weight compound (HPMA) (which is a product of copolymerization of a plurality of hydroxypropylmethacrylamide derivatives) is bonded to the paclitaxel at least at one of the hydroxyl groups thereof through a peptide as a spacer (see, U.S. Pat. No. 5,362,831). In this case also, since the carrier is a synthetic polymer, it is predicted that the carrier would not be degraded at all in a living body. As a result, when a drug complex (prodrug) having the above-mentioned synthetic polymer as a carrier is administered to a living body, there is a danger of the accumulation of the toxicity and antigenicity of the carrier because the carrier stays as a foreign substance in a living body for a long period of time. Therefore, the molecular weight of the carrier should be controlled to a level such that the carrier is not accumulated in a living body, but can be excreted rapidly.

Further, as still another example of a prodrug containing a synthetic polymer as a carrier, there can be mentioned a prodrug comprising paclitaxel (a drug having hydroxyl groups) as a drug, and a polyethylene glycol having introduced thereinto a carboxyl group (hereinafter, simply referred to as "PEG-COOH"), in which a PEG-COOH is bonded, at the carboxyl group thereof, directly to the paclitaxel at least at one of the hydroxyl groups thereof through an ester bond [see, Bioorganic & Medicinal Chemistry Letters, Vol. 4, No. 20, 2465–2470 (1994)]. In this case, the water-solubility of paclitaxel has been improved by bonding paclitaxel to a PEG-COOH so as to form a prodrug.

However, although the prodrug thus formed is stable in a buffer, the ester bond of the prodrug is likely to be rapidly cleaved in blood. Therefore, this prodrug (comprising a drug having bonded thereto a polymer by chemical modification) is still unsatisfactory for attaining the purpose of stably delivering the drug to a target site in a living body.

As apparent from the above, in the techniques of delivering a drug in the form of a prodrug comprising a carrier having bonded thereto a drug through a chemical bond, especially when the chemical bond is an ester bond, the rapid cleavage of an ester bond by an esterase or the like present is likely to occur in a living body. Therefore, the problems of the difficulty of the control of the rate of the release of a drug from a drug complex (prodrug) have not yet been fully solved.

SUMMARY OF THE INVENTION

In this situation, the present inventors have made extensive and intensive studies toward developing a drug complex which is capable of controlling the rate of the release of a drug therefrom, and which is obtained by introducing a spacer into the drug and then bonding the introduced spacer to a carrier.

As a result, it has unexpectedly been found that, when a drug complex of a drug having a hydroxyl group is constructed such that it comprises at least one a carrier having at least one carboxyl group, at least one spacer having at least one amino group and at least one carboxyl group, and at least one drug having a hydroxyl group, wherein the spacer is introduced to the drug through an ester bond formed between the hydroxyl group of the drug and the carboxyl group of the spacer, and wherein the spacer is bonded to the carrier through an amide bond formed between the amino group of the spacer and the carboxyl group of the carrier, the so constructed drug complex is capable of controlling the rate of the release of the drug from the drug complex.

It has also been found that a very effective control of the rate of the release of the drug from the drug complex can be achieved by appropriately selecting at least one spacer having a substituent X at the α-position relative to the carboxyl group of the spacer, wherein the substituent X has a specific Es value.

It has also been found that, when a drug complex of a drug having a hydroxyl group is constructed such that it comprises at least one carrier having at least one carboxyl group, at least one spacer having at least one amino group and at least one carboxyl group and having a substituent X at the α-position relative to the carboxyl group thereof, and at least one water-insoluble drug having a hydroxyl group, such as a taxane compound, wherein the spacer is introduced to the drug through an ester bond formed between the hydroxyl group of the drug and the carboxyl group of the spacer, wherein the spacer is bonded to the carrier through an amide bond formed between the amino group of the spacer and the carboxyl group of the carrier, and wherein the spacer is selected so that substituent X has a specific Es value, the so constructed drug complex is capable of not only controlling the rate of the release of the drug from the drug complex, but also improving the water-solubility of the drug, so that not only can the transferability of the drug to target tissues, such as tumor tissues, be enhanced, but also the exertion of the effect of the drug can be controlled.

Further, it has been found that, when the drug complex has a structure in which a taxane compound is used as the drug, a spacer is introduced into the 2'- or, 7-positioned hydroxyl group of the taxane compound through an ester bond, and a carboxyalkyldextran is used as the carrier, the so constructed drug complex is capable of not only extremely improving the water-solubility of the taxane compound, but also decreasing the rate of the disappearance of the taxane compound in blood, and increasing the transferability of the drug to tumor tissues, thereby enhancing the effect of the taxane compound.

Still further, it has been found that, when the drug complex has a structure in which at least one steroid having a primary hydroxyl group, such as beta-methasone or prednisolone, is used as the drug, at least one spacer (such as an amino acid) having a substituent X at the α-position relative to the carboxyl group thereof, wherein the spacer is appropriately selected so that the substituent X has a specific Es value, is introduced into the primary hydroxyl group of the steroid through an ester bond, and a carboxyalkylmonosaccharide or an aliphatic carboxylic acid, such as acetic acid and propionic acid, is used as the carrier, the so constructed drug complex is capable of controlling the rate of the release of the steroid from the drug complex in a living body, whereas, in a compound (drug complex) prepared by directly bonding a carboxyalkylmonosaccharide as a carrier, [use of a carboxyalkylmonosaccharide as a carrier has been reported in Chem. Pharm. Bull., 42(10), 2090–2096(1994)], or an aliphatic carboxylic acid, such as acetic acid and propionic acid, as a carrier, to the primary hydroxyl group of the steroid, such as betamethasone or prednisolone, through an ester bond, the release of the steroid from the compound is disadvantageously rapid.

Furthermore, it has been found that, when the drug complex has a structure in which at least one paclitaxel having hydroxyl groups is used as the at least one drug, at least one spacer (such as an amino acid) having a substituent X at the α-position relative to the carboxyl group thereof, wherein the spacer is appropriately selected so that the substituent X has a specific Es value, is introduced into one of the hydroxyl groups of the paclitaxel through an ester bond, and a PEG-COOH is used as the carrier, the so constructed drug complex is capable of controlling the rate of the release of paclitaxel from the drug complex in a living body, whereas, in a compound prepared by directly bonding PEG-COOH as a carrier to the hydroxyl group of a drug having hydroxyl groups through an ester bond in a conventional manner, the release of the drug from the compound is disadvantageously rapid in a plasma of rat or human, although the compound is so stable in a buffer that the-half-life of the above-mentioned compound in a buffer is 3 hours or more [see J. Med. Chem., 39, 1938–1940(1996)].

The present invention has been completed based on the above novel findings.

Accordingly, it is an object of the present invention to provide a drug complex of a drug which is capable of not only surely controlling the rate of the release of the drug from the drug complex, but also enhancing the transferability of the drug to the target tissues and the effectiveness of the drug.

It is another object of the present invention to provide a drug complex comprising a taxane compound as a drug, wherein the drug complex is not only capable of extremely improving the solubility of the taxane compound in water, but also surely controlling the rate of the release of taxane compound from the drug complex and enhancing the transferability of the taxane compound to the target tissues and the effectiveness of the taxane compound.

It is still another object of the present invention to provide a medicine, which comprises the above-mentioned drug complex.

The foregoing and other objects, features and advantages of the present invention will be apparent to those skilled in the art from the following detailed description and appended claims taken in connection with the accompanying drawings.

DETAILED DESCRIPTION OF THE INVENTION

Figure 1:
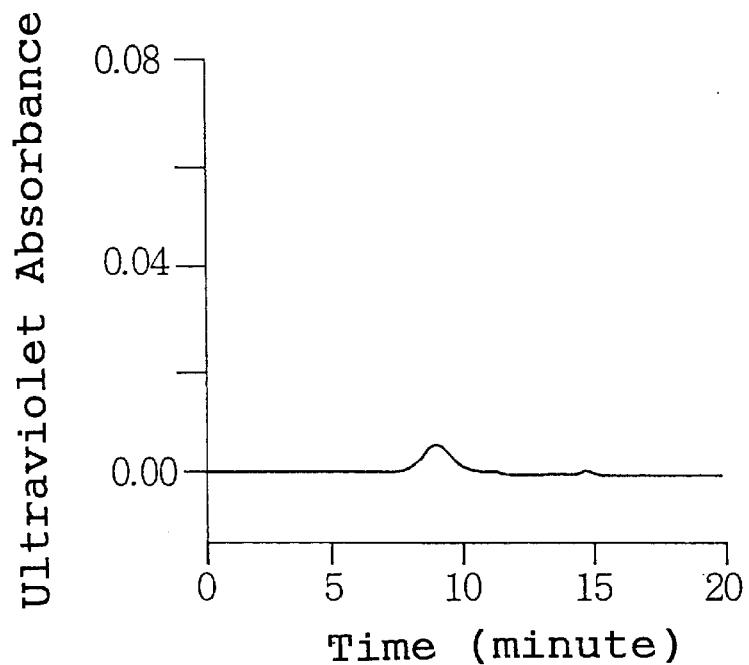
FIG. 1 is a chart showing the gel filtration chromatogram of carboxymethylated dextran sodium salt (1) obtained in Example 1, wherein the chromatogram was obtained using an ultraviolet detector (wavelength: 214 nm).

Essentially, according to the present invention, there is provided a drug complex of a drug having a hydroxyl group, which is capable of controlling the rate of the release of the drug therefrom in blood, the drug complex comprising:

(A) at least one carrier selected from the group consisting of saccharides each having at least one carboxyl group, polyethylene glycols each having at least one carboxyl group, straight or branched $C_2$–$C_8$ aliphatic carboxylic acids each having at least one carboxyl group, and derivatives thereof each having at least one carboxyl group;

(B) at least one spacer comprised of a compound having at least one amino group and at least one carboxyl group; and (C) at least one drug having a hydroxyl group, wherein the at least one drug (C) is bonded to the at least one spacer (B) through an ester bond formed between the hydroxyl group of the drug (C) and the carboxyl group of the spacer (B) to form at least one drug-spacer block, and wherein the at least one drug-spacer block is bonded to the at least one carrier (A) through an amide bond formed between the amino group of the spacer (B) of the at least one drug-spacer block and the carboxyl group of the at least one carrier (A).

For easy understanding of the present invention, the essential features and various embodiments of the present invention are enumerated below.

1. A drug complex of a drug having a hydroxyl group, which is capable of controlling the rate of the release of the drug therefrom in blood, the drug complex comprising:

(A) at least one carrier selected from the group consisting of saccharides each having at least one carboxyl group, polyethylene glycols each having at least one carboxyl group, straight or branched $C_2$–$C_8$ aliphatic carboxylic acids each having at least one carboxyl group, and derivatives thereof each having at least one carboxyl group;

(B) at least one spacer comprised of a compound having at least one amino group and at least one carboxyl group; and (C) at least one drug having a hydroxyl group, wherein the at least one drug (C) is bonded to the at least one spacer (B) through an ester bond formed between the hydroxyl group of the drug (C) and the carboxyl group of the spacer (B) to form at least one drug-spacer block, and wherein the at least one drug-spacer block is bonded to the at least one carrier (A) through an amide bond formed between the amino group of the spacer (B) of the at least one drug-spacer block and the carboxyl group of the at least one carrier (A).

2. The drug complex according to item 1 above, wherein the hydroxyl group of the at least one drug (C), which is bonded to the carboxyl group of the at least one spacer (B) to form the ester bond, is a primary hydroxyl group, and the at least one spacer (B) has a substituent X at the α-position relative to the carboxyl group of the at least one spacer (B), wherein the substituent X has a steric hindrance parameter (Es) value of from −1.0 to −2.5, the Es value being defined by the following formula (1):

$$Es = \log(k_X/k_H) \qquad (1)$$

wherein $k_X$ is the reaction rate constant for the acid hydrolysis reaction of an α-monosubstituted acetic acid ester, wherein the acid hydrolysis reaction is represented by the following formula:

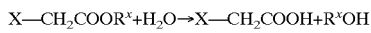
X—CH$_2$COOR$^x$+H$_2$O→X—CH$_2$COOH+R$^x$OH wherein X is as defined above and R$^x$ is a group selected from the group consisting of C$_1$–C$_8$ alkyl groups and C$_6$–C$_{18}$ aryl groups; and $k_H$ is the reaction rate constant for the acid hydrolysis reaction of an unsubstituted acetic acid ester corresponding to the α-monosubstituted acetic acid ester, wherein the acid hydrolysis reaction is represented by the following formula:

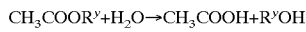
CH$_3$COOR$^y$+H$_2$O→CH$_3$COOH+R$^y$OH wherein R$^y$ has the same meaning as defined for R$^x$.

3. The drug complex according to item 1 above, wherein the hydroxyl group of the at least one drug (C), which is bonded to the carboxyl group of the at least one spacer (B) to form the ester bond, is a secondary hydroxyl group, and the at least one spacer (B) has a substituent X at the α-position relative to the carboxyl group of the at least one spacer (B), wherein the substituent X has a steric hindrance parameter (Es) value of from –0.0 to –2.5, the Es value being defined by the following formula (1):

$$Es = \log(k_X/k_H) \tag{1}$$

wherein $k_X$ is the reaction rate constant for the acid hydrolysis reaction of an α-monosubstituted acetic acid ester, wherein the acid hydrolysis reaction is represented by the following formula:

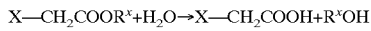
X—CH$_2$COOR$^x$+H$_2$O→X—CH$_2$COOH+R$^x$OH wherein X is as defined above and R$^x$ is a group selected from the group consisting of C$_1$–C$_{18}$ alkyl groups and C$_6$–C$_{18}$ aryl groups; and $k_H$ is the reaction rate constant for the acid hydrolysis reaction of an unsubstituted acetic acid ester corresponding to the α-monosubstituted acetic acid ester, wherein the acid hydrolysis reaction is represented by the following formula:

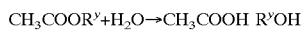
CH$_3$COOR$^y$+H$_2$O→CH$_3$COOH R$^y$OH wherein R$^y$ has the same meaning as defined for R$^x$.

4. The drug complex according to item 1 above, wherein the carrier (A) is selected from the group consisting of polysaccharides each having at least one carboxyl group and derivatives thereof each having at least one carboxyl group.

5. The drug complex according to item 4 above, wherein the carrier (A) is a carboxyalkyldextran.

6. The drug complex according to item 1 above, wherein the at least one carrier (A) is selected from the group consisting of monosaccharides each having at least one carboxyl group and derivatives thereof each having at least one carboxyl group.

7. The drug complex according to item 1 above, wherein the at least one spacer (B) is selected from the group consisting of glycine, alanine, leucine, isoleucine and phenylalanine.

8. The drug complex according to any one of items 1, 3, 4, 5, 6 and 7 above, wherein the at least one drug (C) is selected from the group consisting of taxane compounds.

9. The drug complex according to any one of items 1, 2, 4, 5, 6 and 7 above, wherein the at least one drug (C) is selected from the group consisting of steroids.

10. A medicine comprising the drug complex of any one of items 1 to 7 above.

11. A medicine comprising the drug complex of item 8 above.

12. A medicine comprising the drug complex of item 9 above.

13. The drug complex according to item 1 above, wherein:
the drug (C) is at least one taxane compound represented by the following formula (2):

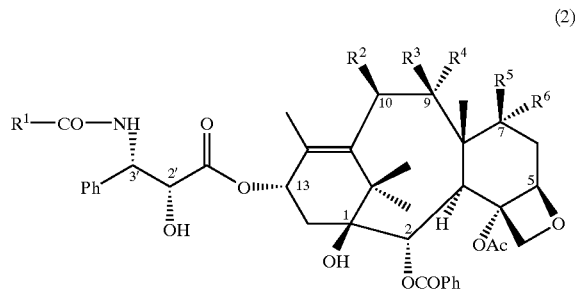

wherein R$^1$ represents a group selected from the group consisting of a straight or branched C$_1$–C$_6$ alkyl group, a straight or branched C$_2$–C$_6$ alkenyl group, a straight or branched C$_2$–C$_6$ alkynyl group, a straight or branched C$_1$–C$_6$ alkoxy group and an unsubstituted or substituted phenyl group; R$^2$ represents a group selected from the group consisting of a hydrogen atom, a hydroxyl group and an acetyloxy group; one of R$^3$ and R$^4$ represents a hydrogen atom and the other represents a hydroxyl group, or R$^3$ and R$^4$ together form an oxo group; one of R$^5$ and R$^6$ represents a hydrogen atom and the other represents a hydroxyl group; Ac represents an acetyl group; and Ph represents a phenyl group, the at least one taxane compound of formula (2) is bonded, at the 2'- or 7-positioned hydroxyl group thereof, to the at least one spacer (B) at the carboxyl group thereof through the ester bond formed between the hydroxyl group and the carboxyl group, the carrier (A) is a carboxyalkyldextran represented by the following formula (3):

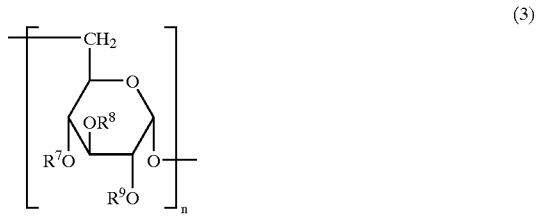

wherein each of R$^7$, R$^8$ and R$^9$ independently represents a hydrogen atom or a carboxylalkyl group selected from the group consisting of —(CH$_2$)$_m$—COOH, —CH(CH$_3$)—COOH, —CH$_2$CH(CH$_3$)—COOH and —CH(CH$_3$)CH$_2$—COOH, wherein m represents an integer of from 1 to 4; and n represents an integer of from 50 to 1000, with the proviso that the ratio of the number of carboxylalkyl groups to the number of n is 0.1 to 2.0, and the carboxyalkyldextran is bonded, at the carboxyl moiety of at least one of the carboxyalkyl groups thereof, to the at least one spacer (B) at the amino group thereof through the amide bond formed between the amino group and the carboxyl group.

14. The drug complex according to item 13 above, wherein the at least one spacer (B) has a substituent X at the α-position relative to the carboxyl group, wherein the substituent X has a steric hindrance parameter (Es) value of from −0.0 to −2.5, the Es value being defined by the following formula (1):

$$Es = \log(k_X/k_H) \tag{1}$$

wherein $k_X$ is the reaction rate constant for the acid hydrolysis reaction of an α-monosubstituted acetic acid ester, wherein the acid hydrolysis reaction is represented by the following formula:

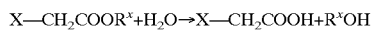

$$X\text{—}CH_2COOR^x + H_2O \rightarrow X\text{—}CH_2COOH + R^xOH$$

wherein X is as defined above and $R^x$ is a group selected from the group consisting of $C_1$–$C_{18}$ alkyl groups and $C_6$–$C_{18}$ aryl groups; and $k_H$ is the reaction rate constant for the acid hydrolysis reaction of an unsubstituted acetic acid ester corresponding to the α-monosubstituted acetic acid ester, wherein the acid hydrolysis reaction is represented by the following formula:

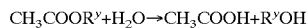

$$CH_3COOR^y + H_2O \rightarrow CH_3COOH + R^yOH$$

wherein $R_y$ has the same meaning as defined for $R^x$.

15. The drug complex according to item 13 or 14 above, wherein the drug (C) is at least one paclitaxel.
16. The drug complex according to item 13 or 14 above, wherein the drug (C) is at least one docetaxel.
17. An antitumor medicine, which comprises the drug complex of item 13 or 14 above.
18. An antitumor medicine, which comprises the drug complex of item 15 above.
19. An antitumor medicine, which comprises the drug complex of item 16 above.

With respect to the drug used in the present invention, there is no particular limitation, as long as the drug has a hydroxyl group. With respect to the type of the hydroxyl group, there is no particular limitation, and the hydroxyl group may be either a primary hydroxyl group or a secondary hydroxyl group.

In the present invention, the term "primary hydroxyl group" means a hydroxyl group directly bonded to a primary carbon atom, such as a hydroxyl group of ethanol or 1-butanol, and the term "secondary hydroxyl group" means a hydroxyl group directly bonded to a secondary carbon atom, such as a hydroxyl group of 2-propanol or 2-butanol. Examples of drugs having a primary hydroxyl group, which can be used in the present-invention, include betamethasone, prednisolone, dexamethasone (each of which is a steroid) and the like. On the other hand, examples of drugs having a secondary hydroxyl group, which can be used in the present invention include taxane compounds represented by the following formula (2):

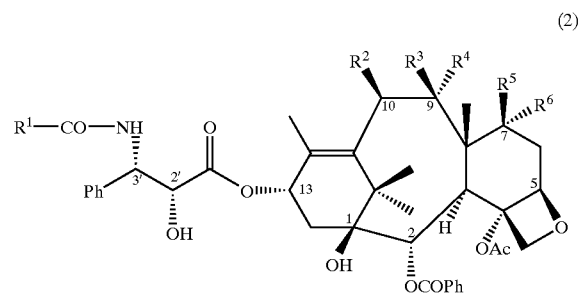

wherein $R^1$ represents a group selected from the group consisting of a straight or branched $C_1$–$C_6$ alkyl group, a straight or branched $C_2$–$C_6$ alkenyl group, a straight or branched $C_2$–$C_6$ alkynyl group, a straight or branched $C_1$–$C_6$ alkoxy group and an unsubstituted or substituted phenyl group; $R^2$ represents a group selected from the group consisting of a hydrogen atom, a hydroxyl group and an acetyloxy group; one of $R^3$ and $R^4$ represents a hydrogen atom and the other represents a hydroxyl group, or $R^3$ and $R^4$ together form an oxo group; one of $R^5$ and $R^6$ represents a hydrogen atom and the other represents a hydroxyl group; Ac represents an acetyl group; and Ph represents a phenyl group.

As specific examples of taxane compounds, there can be mentioned paclitaxel (tradename: Taxol; manufactured and sold by Brystol-Myers Squibb, U.S.A.) represented by the following formula (4) and docetaxel (tradename: Taxotere; manufactured and sold by Rhône-Poulenc Rorer Pharmaceuticals Limited, U.S.A./France) represented by the following formula (5). Further, derivatives of paclitaxel and docetaxel are also included in the taxane compounds which can be used in the present invention.

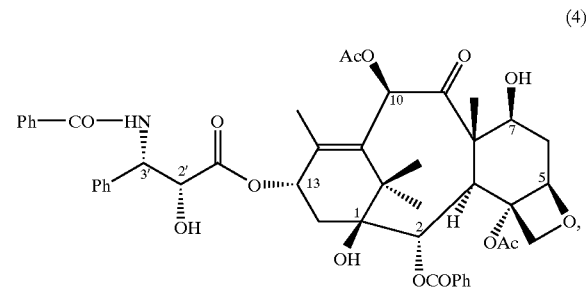

and

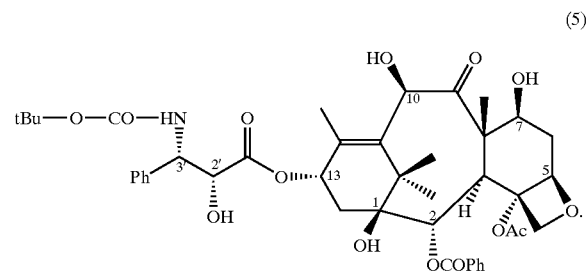

The spacer which can be used in the present invention comprises a compound having at least one amino group and at least one carboxyl group in a molecular structure. In the drug complex, such a spacer having bonded thereto a drug can usually release the drug or active molecular species thereof therefrom rapidly or, occasionally, gradually by the action of enzymes present in organs, such as a protease, a peptidase and an esterase. As examples of such spacers, there can be mentioned amino acids occurring in proteins, amino acids not occurring in proteins, and peptides comprising these amino acids, wherein mutually adjacent two amino acids contained in the peptide are bonded through a peptide (amide) bond.

In the present invention, the term "amino acid occurring in proteins" means a constituent amino acid of proteins, such as glycine, alanine, phenylalanine, leucine, isoleucine or the like. On the other hand, the term "amino acid not occurring in proteins" means an amino acid other than constituent amino acids of proteins, such as norleucine, norvaline, hydroxyproline, pyroglutamic acid, β-cyclohexylalanine, β-alanine, ε-aminocaproic acid, γ-aminobutyric acid or the like.

In the present invention, when a compound having a substituent X at the α-position relative to the carboxyl group of the compound is used as a spacer, the magnitude of the steric hindrance caused by the substituent X has a great influence on the rate of the release of the drug from the drug complex of the present invention. Therefore, the rate of the release of the drug from the drug complex can be controlled by appropriately selecting a spacer having a substituent X at the α-position relative to the carboxyl group, wherein the substituent X has a specific magnitude of steric hindrance.

In general, in a chemical reaction, when a substituent is present in the neighborhood of the center of the reaction, the substituent has various effects on the progress of the reaction. Steric hindrance is one of these effects. The term "steric hindrance" means such an effect that the presence of a bulky substituent X in the neighborhood of the center of the reaction inhibits the progress of the chemical reaction. It is considered that the bulky substituent X present in the neighborhood of the center of the reaction inhibits the approach of a reagent to the center of the reaction, so that the steric hindrance occurs. The magnitude of the steric hindrance depends on the bulkiness of the substituent X.

As a value for numerically expressing the magnitude of the steric hindrance of a substituent, the so-called "Es value" defined by Taft et al. is known (American Chemical Society Professional Reference Book, "Exploring QSAR", written by C. Hansch and A. Leo and edited by S. R. Hell). The rate of the release of the drug from the drug complex can be effectively controlled by selecting a spacer having a substituent X at the α-position relative to the carboxyl group of the spacer, wherein the substituent X has a specific Es value. Explanation on the Es value is made below.

From the results of various experiments, it is known that, in the acid hydrolysis reaction of an ester, the effect of the substituent of the ester on the progress of the reaction can be considered to be the steric hindrance only. This known fact was utilized for numerically expressing the magnitude of the steric hindrance of the substituent. Thus, a concept of the "Es value" has been established.

The Es value of a substituent X can be determined by the following formula (1):

$$Es = \log(k_X/k_H) \quad (1)$$

wherein $k_X$ is the reaction rate constant for the acid hydrolysis reaction of an α-monosubstituted acetic acid ester which is derived from an α-monosubstituted acetic acid obtained by substituting one hydrogen atom of the methyl group of acetic acid with a substituent X, wherein the acid hydrolysis reaction is represented by the following formula:

$$X-CH_2COOR^x + H_2O \rightarrow X-CH_2COOH + R^xOH$$

wherein X is as defined above and $R^x$ is a group selected from the group consisting of $C_1-C_{18}$ alkyl groups and $C_6-C_{18}$ aryl groups; and $k_H$ is the reaction rate constant for the acid hydrolysis reaction of an acetic acid ester corresponding to the above-mentioned α-monosubstituted acetic acid ester, wherein the acid hydrolysis reaction is represented by the following formula:

$$CH_3COOR^y + H_2O \rightarrow CH_3COOH + R^yOH$$

wherein $R^y$ has the same meaning as define for 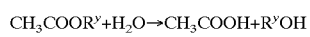

The reaction rate is lowered by the steric hindrance caused by the substituent X and, therefore, $k_X$ is smaller than $k_H$, so that the Es value usually becomes negative.

When the Es value is actually determined, first, the above-mentioned two reaction rate constants for the acid hydrolysis reaction, i.e., $k_X$ and $k_H$, are determined, followed by calculation of the Es value by formula (1) described above. In the above-mentioned textbook (American Chemical Society Professional Reference Book, 'Exploring QSAR' p.81 Table 3–3), specific examples of Es values obtained by the actual measurements are described. Some examples of Es values are shown below.

| Types of substituents X | Es values |
|---|---|
| H | 0 (standard) |
| CH$_3$ | −1.24 |
| CH$_2$C$_6$H$_5$ | −1.61 |
| CH$_2$CH(CH$_3$)$_2$ | −2.17 |
| CH(CH$_3$)CH$_2$CH$_3$ | −2.37 |

In the present invention, as mentioned above, an amino acid occurring in proteins can be used as a spacer. The amino acids having the substituents shown above at the α-positions relative to the carboxyl groups thereof are glycine (Gly), Alanine (Ala), Phenylalanine (Phe), Leucine (Leu) and isoleucine (Ile). When, among these amino acids, Gly, Ala, Leu and Ile are arranged in the order of magnitude of Es value (in absolute value) of the substituent at the α-position relative to the carboxyl group thereof, the order can be shown by Ile>Leu>Ala>Gly. That is, the magnitude of the steric hindrance of the substituent of the amino acid becomes smaller in this order. Further, the magnitude of the steric hindrance of the substituent correlates with the rate of the release of the drug from the drug complex of the present invention.

For example, with respect to the drug complexes which are so constructed that the spacer is Gly, Ala, Leu or Ile, the drug is-paclitaxel, and the carrier is carboxymethyldextran, when-the amino acids used as the spacer in the drug complexes are arranged in the order of the rate of the release of the drug from the drug complex in a living body, the order can be shown by Gly>Ala>Leu>Ile.

On the other hand, with respect to the drug complexes which are substantially the same as mentioned above, except that the amino acids used as the spacer in the drug complexes are Gly or Phe, when the amino acids used as the spacer in the drug complexes are arranged in the order of the rate of the release of the drug from the drug complex in a living body, the order can be shown by Gly>Phe.

Therefore, with respect to the above-mentioned drug complexes, the Es value (i.e., the magnitude of the steric hindrance) of the substituent of the spacer at its α-position relative to the carboxyl group of the spacer has a correlation with the rate of the release of the drug.

In another example where the drug complexes are so constructed that the spacer is Gly, Ala, Leu or Ile, the drug is dexamethasone and the carrier is propionic acid, when the amino acids used as the spacer in the drug complexes are arranged in the order of the rate of the release of the drug in a living body, the order can be shown by Gly>Ala>Leu>Ile. Therefore, also with respect to the above-mentioned drug complexes, the Es value (i.e., the magnitude of the steric hindrance) of the substituent of the spacer at its α-position relative to the carboxyl group of the spacer has a correlation with the a rate of the release of the drug.

In still another example where the drug complexes are so constructed that the spacer is a peptide Gly-Phe or a peptide Phe-Gly, the drug is paclitaxel and the carrier is carboxymethyldextran, when the peptides used as the spacer in the drug complexes are arranged in the order of the rate of the release of the drug from the drug complex in a living body, the order can be shown by Phe-Gly>Gly-Phe. Therefore, also with respect to the above-mentioned drug complexes, the Es value (i.e., the magnitude of the steric hindrance) of the substituent at the α-position relative to the carboxyl group of the spacer has a correlation with the rate of the release of the drug. Further, as apparent from the above, even in the case of the drug complex wherein the spacer is a peptide or the like, the important factor for the control of the rate of the release of the drug from the drug complex is the magnitude of the steric hindrance of the substituent of the spacer at its α-position relative to the carboxyl group of the spacer, wherein the carboxyl group of the spacer is bonded directly to the hydroxyl group of the drug in the drug complex.

The carrier which can be used in the present invention is selected from the group consisting of saccharides each having at least one carboxyl group, polyethylene glycols each having at least one carboxyl group, straight or branched $C_2$–$C_8$ aliphatic carboxylic acids each having at least one carboxyl group, and derivatives thereof each having at least one carboxyl group.

With respect to the saccharides each having at least one carboxyl group and derivatives thereof each having at least one carboxyl group, which can be used in the present invention, there is no particular limitation as long as they have at lest one carboxyl group. However, a carboxyalkylated dextran (carboxyalkyldextran) is especially preferred.

The carboxyalkyldextran which can be used in the present invention as a carrier has a structure wherein the hydrogen atom or atoms of part or all of the hydroxyl groups of dextran is/are substituted with a carboxyalkyl group, and the carboxyalkyldextran is composed mainly of a unit (a sugar residue) represented by the following formula (3):

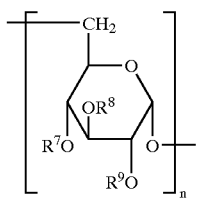

(3)

wherein each of $R^7$, $R^8$ and $R^9$ independently represents a hydrogen atom or a carboxyalkyl group selected from the group consisting of —$(CH_2)_m$—COOH, —CH($CH_3$)—COOH, —$CH_2CH(CH_3)$—COOH and —CH($CH_3$)$CH_2$—COOH, wherein m represents an integer of from 1 to 4; and n represents an integer of from 50 to 1000, with the proviso that the ratio of the number of carboxylalkyl groups to the number of n is 0.1 to 2.0.

Further, the carboxyalkyldextran may have a branched chain structure.

As examples of preferable carboxyalkyl groups, there can be mentioned a carboxymethyl group, a carboxyethyl group, a carboxy-n-propyl group, a carboxyisopropyl group, a carboxy-n-butyl group and the like.

With respect to the above-mentioned carboxyalkyldextran, the degree of introduction of the carboxyalkyl groups can be represented by the "degree of substitution" defined as the number of the carboxyalkyl groups (including carboxyalkyl groups each having introduced thereto a peptide as a spacer) per saccharide residue. That is, the degree of substitution of carboxyalkyldextran is represented by the following formula:

$$\text{Degree of substitution of carboxyalkyldextran} = \frac{\text{Total number of carboxyalkyl groups in the molecule of carboxyalkyldextran}}{\text{Total number of sugar residues in the molecule of carboxyalkyldextran}}$$

Hereinafter, when a carboxyalkyl group is a carboxymethyl group, the above-mentioned degree of substitution may be referred to as a "degree of carboxymethylation." With respect to a carboxyalkyldextran, when all of the hydrogen atoms of the hydroxyl groups are substituted with a carboxyalkyl group, the degree of substitution is 3. In the present invention, it is preferred that the degree of substitution is 0.1 or more, more advantageously from 0.1 to 2.0 from the viewpoint of the pharmacokinetics of the drug in a living body.

A carboxyalkyldextran which can be preferably used as a carrier in the present invention can be obtained by introducing carboxyalkyl groups into hydroxyl groups of dextran. For example, dextran is dissolved in an appropriate solvent in the presence of alkali (for example, when water is used as the solvent, in the presence of sodium bicarbonate, potassium carbonate, aqueous ammonia, sodium hydroxide or the like, and when an appropriate organic solvent, such as N,N-dimethylformamide, dimethylsulfoxide or the like is used as a solvent, in the presence of pyridine, triethylamine or the like), and monochloroacetic acid is then added thereto, followed by effecting a reaction at a temperature of from an ice-cooled temperature to room temperature for a period of from several minutes to several days, to thereby obtain a reaction mixture. Subsequently, the pH value of the obtained reaction mixture is adjusted to 8 by adding thereto an acid, such as acetic acid, and the reaction mixture is added dropwise into ethanol, to thereby obtain a carboxymethyldextran as a precipitate. In this case, the "degree of substitution" of carboxyalkyldextran can be adjusted by changing the reaction solvent, reaction time, reaction temperature, or amount of monochloroacetic acid or alkali to be added.

In the present invention, when the carrier is selected from the group consisting of polyethylene glycols each having at least one carboxyl group and derivatives thereof each having at least one carboxyl group, it is preferred that the polyethylene glycol or derivative thereof has a molecular weight of from 1,000 to 40,000.

Hereinbelow, a description is made with respect to the method for producing the drug complex of the present invention. The drug complex of the present invention is obtained by introducing at least one spacer into at least one drug thereby obtaining at least one drug-spacer block, followed by introducing the obtained at least one drug-spacer block into at least one carrier. It is preferred that the synthetic reactions for producing the drug complex of the present invention are conducted under as mild conditions as possible in order to avoid the lowering of the activity of the drug or, in order to avoid the crosslinking or aggregation of the carrier in the synthetic processes when the carrier is a high molecular weight compound. From this point of view, for producing the drug complex of the present invention, it is preferred to use the same method as used in the peptide synthesis.

Now, description is made with respect to the method for introducing a spacer into a drug to thereby obtain a drug-spacer block. In the present invention, the spacer is introduced into the drug by forming an ester bond between the carboxyl group of the spacer and the hydroxyl group of the drug.

The formation of an ester bond can be achieved by a method comprising reacting a predetermined amount of the drug and a predetermined amount of the spacer in a solvent which can be used for ordinary organic synthetic reactions, such as methylene chloride, N,N-dimethylformamide, tetrahydrofuran or the like, in an amount sufficient for dissolving the drug, spacer and other reagents, in the presence of an appropriate condensing agent, such as N,N'-dicyclohexylcarbodiimide, N,N'-diisopropylcarbodiimide, 1-ethyl-(3-dimethylaminopropyl)carbodiimide hydrochloride, 1-ethoxycarbonyl-2-ethoxy-1,2-dihydroquinoline or the like, in an amount equivalent to the molar amount of the drug, and, if desired, in the presence of N,N-dimethylaminopyridine, in an amount equivalent to the molar amount of the drug or in a catalytic amount, at room temperature or under heating, if desired, in an atmosphere of dry inert gas, such as argon and helium, and under atmospheric pressure for a period of from several hours to several days. Further, it is preferred that, prior to the above-mentioned reaction, a functional group of the spacer or drug which may cause undesirable side reactions is protected by a protective group as used for peptide synthesis. For example, it is preferred that an amino group is protected by an Fmoc (9-fluorenylmethyloxycarbonyl) group, a Trt [triphenylmethyl (trityl)] group, a Z (benzyloxycarbonyl) group or the like, that a carboxyl group is protected by a benzyl ester group, a tertially butyl ester group, a phenacyl ester group or the like, and that a hydroxyl group is protected by a benzyl ether group, a tertially butyl ether group or the like.

Next, description is made below with respect to the method for introducing the drug-spacer block into a carrier.

When the amino group of the spacer of the drug-spacer block is protected, the amino group of the spacer is deprotected by the method as used for peptide synthesis. For example, when a Z group is used as a protective group, deprotection can be achieved by hydrogenation in the presence of palladium, or the like. When an Fmoc group is used as a protective group, deprotection can be achieved by the treatment with piperidine or the like. When a Trt group is used as a protective group, deprotection can be achieved by the treatment with acetic acid or the like.

Subsequently, an amide bond is formed between the amino group of the spacer of the drug-spacer block and the carboxyl group of the carrier. The formation of the amide bond can be achieved by a method comprising reacting a predetermined amount of the drug-spacer block with a predetermined amount of the carrier in a solvent which can be used for ordinary organic synthetic reactions, such as methylene chloride, N,N-dimethylformamide, tetrahydrofuran or the like (or, especially when the carrier is water-soluble, in a mixed solvent of water with a hydrophilic organic solvent, such as N,N-dimethylformamide, dimethylsulfoxide or the like) in an amount sufficient for dissolving the drug-spacer block, carrier and other reagents [occasionally, in the presence of a predetermined amount of an appropriate condensing agent, such as N,N'-dicyclohexylcarbodiimide, N,N'diisopropylcarbodiimide, 1-ethyl-(3-dimethylaminopropyl) carbodiimide hydrochloride, 1-ethoxycarbonyl-2-ethoxy-1,2-dihydroquinoline or the like] at 4° C. or room temperature under atmospheric pressure for a period of from several hours to several days. Further, the amount of the drug to be introduced into the drug complex can be controlled by changing the amount of the drug-spacer block relative to the amount of the carrier, the reaction time or the amount of the condensing agent.

In the present invention, with respect to the spacer used for bonding the carrier having at least one carboxyl group to the drug having a hydroxyl group, there is no particular limitation as long as it has at least one amino group and at least one carboxyl group. Hereinbelow, description is made with respect to a peptide as an example of the spacer.

From the viewpoint of the preferred drug-releasing properties of the drug complex and avoidance of complicatedness of the synthetic process of a peptide, it is preferred that the peptide used as a spacer in the present invention comprises six amino acids residues or less, more advantageously four amino acid residues or less. Further, "a peptide comprising amino acids" includes a peptide comprising a compound (or compounds) other than amino acids as a part thereof, as well as a peptide consisting of only amino acids. For example, the peptide can comprise a dibasic carboxylic acid, such as succinic acid, in the peptide chain or at a terminus thereof. Further, an amino acid contained in the above peptide can be an amino acid other than an α-amino acid, such as an amino acid occurring in proteins. Examples of such other types of amino acids include β-alanine, ε-aminocaproic acid or γ-aminobutylic acid. Further, with respect to the manner of bonding the peptide to the carrier, the peptide is usually bonded, at the amino group of the N-terminus thereof, to the carrier at the carboxyl group thereof through an amide bond. However, the peptide can be bonded to the carrier in such a manner that an amino acid having two amino groups is bonded, at one of the two amino groups thereof (e.g., at the ε-amino group thereof when a peptide containing lysine is used) to a carrier at the carboxyl group thereof, that the amino acid having two amino groups is bonded, at the other amino group thereof, to the peptide at the carboxyl group of the C-terminus thereof, thereby reversing the bonding direction of the peptide, and that an amino acid having two carboxyl groups, such as glutamic acid, is bonded, at one carboxyl group thereof, to the peptide at the amino group of the N-terminus thereof, and bonded, at the other carboxyl group thereof, to a drug at the hydroxyl group.

There is no particular limitation with respect to the types of the amino acids contained in the peptide, as long as the peptide has a structure such that the drug or corresponding active molecular species can be released rapidly or, if desired, gradually from the drug complex by the action of enzymes present in organs, such as a protease, a peptidase and an esterase. The amino acid contained in the peptide can be a neutral, basic or acidic amino acid. In one preferred embodiment of the present invention, the peptide is Phe-Gly, or a peptide containing amino acid sequence -Phe-Gly- in the peptide chain. Such a peptide is bonded, at the amino group of the N-terminus thereof, to the carrier at the carboxyl group thereof through an amide bond.

Now, description is made with respect to the method for introducing a peptide into a taxane compound, as an example of the methods for introducing a peptide as a spacer into a drug for obtaining a drug-spacer block. In this case, the introduction of a peptide into a taxane compound is achieved by bonding the taxane compound, at the 2'- or 7-positioned hydroxyl group thereof, to the peptide at the C-terminus thereof through an ester bond.

The introduction of a peptide into a taxane compound at the 2'-positioned hydroxyl group thereof can be achieved by reacting the peptide directly with the taxane compound in the presence of an appropriate condensing agent, such as N,N'-dicyclohexylcarbodiimide, N,N'-diisopropylcarbodiimide, 1-ethyl-(3-dimethylaminopropyl) carbodiimide hydrochloride, 1-ethoxycarbonyl-2-ethoxy-1, 2-dihydroquinoline or the like. Further, it is preferred that prior to the above reaction, each of the N-terminus of the peptide and the functional groups of the side chain of the peptide which may cause side reactions is protected by protective groups as used for peptide synthesis, such as an Fmoc (9-fluorenylmethyloxycarbonyl) group, a Trt [triphenylmethyl (trityl)] group, a Z (benzyloxycarbonyl) group or the like.

When a peptide is introduced into a taxane compound at the 7-positioned hydroxyl group thereof, the 2'-positioned hydroxyl group of the taxane compound is protected by an appropriate protective group, for example, which is frequently used for peptide synthesis, such as a Z group, followed by introduction of the desired peptide into the taxane compound at 7-positioned hydroxyl group thereof in the same manner as mentioned above. In both of the above two cases, it is preferred that, after introduction of the protected peptide, the protective groups are removed under such conditions that the taxane compound is not decomposed, e.g., by hydrogenation, or under weakly acidic or weakly basic conditions.

Next, as an example of the method for introducing a drug-spacer block into a carrier, description is made with respect to the method for introducing a drug-spacer block (which consists of a peptide as a spacer and a taxane compound having introduced thereinto the peptide at the 2'- or 7-positioned hydroxyl group thereof as obtained by the above-mentioned method) into a carboxyalkyldextran as a carrier. In this case, the introduction of the drug-spacer block into the carrier can be achieved by bonding the N-terminus of the peptide as a spacer to the carrier at the carboxyl group thereof through an amide bond. The formation of the amide bond can be achieved by reacting the carboxyalkyldextran with the above-mentioned drug-spacer block in a mixed solvent of a hydrophilic organic solvent, such as N,N-dimethylformamide, dimethylsulfoxide or the like and water (occasionally, in the presence of an appropriate condensing agent, such as N,N'-dicyclohexylcarbodiimide, N,N'-diisopropylcarbodiimide, 1-ethyl-(3-dimethylaminopropyl) carbodiimide hydrochloride, 1-ethoxycarbonyl-2-ethoxy-1, 2-dihydroquinoline, O-(7-azabenzotriazole-1-yl)-1,1,3,3-tetramethyluronium hexafluorophosphate (HATU) or the like).

Hereinbelow, description is made with respect to the drug introduction ratio and administration method of the drug complex, which comprises a drug having a hydroxyl group, a spacer having at least one amino group and at least one carboxyl group and a carrier having at least one carboxyl group.

The drug introduction ratio into the carrier is appropriately selected depending on the type of the drug. However, generally, the drug introduction ratio is preferably from 1 to 30% by weight, more preferably from 1 to 15% by weight, based on the weight of the drug complex, so that the preferable kinetics of the carrier in a living body can be reflected on the kinetics of the drug complex.

The drug complex obtained in the above-mentioned manner can be used in the same manner as in the case of the drug as such. The dose, dosage form and dosage schedule of the drug complex of the present invention are not particularly limited and may be varied depending on the drug complex used. The drug complex of the present invention can be administered in any appropriate route, preferably in a parenteral manner, and the dose of the drug complex may be varied depending on the composition of the formulation containing the drug complex, the administration route or the administration site for the drug complex, the species of the host, the disease to be treated or the like. Further, when the dose of the drug complex is selected, a variety of factors which may change the effectiveness of the drug, such as age, body weight, sex, diet and physical conditions of the patient and the like must be taken into consideration.

Hereinbelow, description is made of the drug introduction ratio, solubility and administration method with respect to one example of the drug complex of the present invention, wherein the drug is paclitaxel, the spacer is an amino acid or a peptide and the carrier is a carboxyalkyldextran.

Generally, the introduction ratio of paclitaxel into the carboxyalkyldextran is preferably from 1 to 30% by weight, more preferably from 1 to 10% by weight, based on the weight of the drug complex, so that the preferable kinetics of carboxyalkyldextran as a carrier in a living body can be reflected on the kinetics of the drug complex.

The above-obtained drug complex comprising a carboxyalkyldextran as a carrier, an amino acid or peptide as a spacer and paclitaxel as a drug shows extremely high water-solubility as compared to paclitaxel per se. That is, the water-solubility of the above drug complex is as high as 1.6 mg/ml or more in terms of the solubility of paclitaxel, whereas the water-solubility of paclitaxel is reported to be less than 0.004 mg/ml [Nature, 365, 464–466 (1993)]. Therefore, in an antitumor assay, the drug complex of the present invention can be dissolved directly in a physiological saline without using a dissolving adjuvant, and can be administered intravenously.

The drug complex of the present invention can be used in the same manner as in the case of the drug per se. The dose, dosage form and dosage schedule of the drug complex of the present invention are not particularly limited and can be varied depending on the drug complex used. The drug complex of the present invention can be administered in any appropriate route, preferably in a parenteral manner. When the drug is paclitaxel, the dose is, generally, approximately 20 to 1,000 mg/m$^2$ of the total body surface area per day for an adult, in terms of the amount of paclitaxel. The actual dose can be varied depending on the composition of the formulation containing the drug complex, the administration route or the administration site for the drug complex, the species of the host, the tumor to be treated or the like. Further, when the dose of the drug complex is selected, a variety of factors which may change the effectiveness of the drug, such as age, body weight, sex, diet and physical conditions of the patient and the like must be taken into consideration.

BEST MODE FOR CARRYING OUT THE INVENTION

Hereinbelow, the present invention will be described in more detail with reference to the following Examples, Reference Examples and Experiments, which, however, should not be construed as limiting the scope of the present invention.

The compound numbers used in Examples correspond to the numbers used in the schemes showing synthetic processes mentioned below.

Further, the degree of carboxymethylation of polysaccharide derivative was determined by titration with alkali. The introduction ratio of the drug (weight %) was determined from the absorbance analysis of the drug (at a wavelength of 254 nm). Gel filtration was conducted under the following conditions:

Column: TSKgel G4000PW$_{XL}$ (manufactured and sold by Tosoh Corporation, Japan);

eluate: 0.1 M Nacl;

flow rate: 0.8 ml/min.;

temperature of the column: 40° C.; and amount of the sample per injection: approximately 50 μg.

High resolution mass spectrum (hereinafter simply referred to as "HRMS") was obtained by fast atom bombardment mass spectrometry (FAB-MS) by means of a mass spectrometer HX-110 (manufactured and sold by JEOL, Ltd., Japan) using glycerin or a mixture of glycerin and 3-nitrobenzylalcohol as a matrix.

In the following Reference Examples and Examples, the following abbreviations are used.

DMF: N,N-dimethylformamide

Trt: triphenylmethyl (trityl) group

Z: benzyloxycarbonyl group

Fmoc: 9-fluorenylmethyloxycarbonyl group

PEG: poly (ethyleneglycol) methyl ether having a molecular weight of 5,000 tBuOK: Potassium t-butoxide

DMSO-d$_6$: deuterated dimethylsulfoxide

EXAMPLE 1

(Step 1) Production of a carboxymethylated dextran sodium salt (1)

Figure 2:
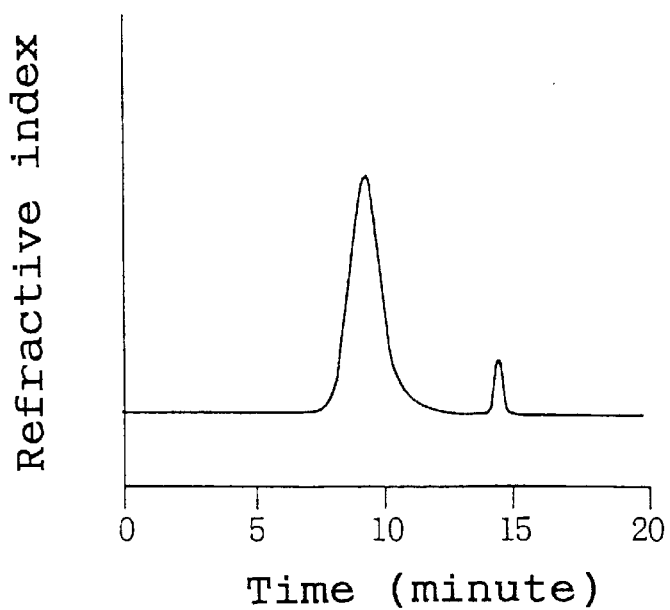
FIG. 2 is a chart showing the gel filtration chromatogram of carboxymethylated dextran sodium salt (1) obtained in Example 1, wherein the chromatogram was obtained using a differential refractometer as a detector.

40 g of sodium hydroxide was added to and dissolved into 200 ml of purified water while cooling over ice. Into the resultant solution was dissolved 10 g of dextran T110, (manufactured and sold by Extrasyntese, France), to thereby obtain a mixture. To the obtained mixture was added 50 g of monochloroacetic acid at room temperature to effect a reaction for 20 hours, to thereby obtain a reaction mixture. The pH value of the obtained reaction mixture was adjusted to 8 with acetic acid. The reaction mixture having a pH value of 8 was poured into 1.5 liters of methanol, to thereby generate a precipitate. The generated precipitate was collected and dissolved in 200 ml of purified water, to thereby obtain a solution. The obtained solution was dialyzed against purified water using a dialysis membrane (cut off molecular weight: 12,000 to 14,000, manufactured and sold by Spectrum Medical Ind., Inc., U.S.A) at 4° C. for two days, to thereby obtain a dialyzate. The obtained dialyzate was subjected to filtration using a membrane filter (pore size: 0.22 μm), followed by lyophilization to thereby obtain compound (1) (11.5 g). The degree of carboxymethylation of the obtained compound (1) per sugar residue was 0.6. The gel filtration chromatograms of compound (1) are shown in FIGS. 1 and 2. The chromatogram shown in FIG. 1 was obtained using an ultraviolet detector (wavelength: 214 nm). The chromatogram shown in FIG. 2 was obtained using a differential refractometer as a detector. The molecular weight of compound (1) was approximately 150,000, as measured by gel filtration using pullulan as a standard.

(Step 2) Production of 2'-Gly-paclitaxel (2)

Fmoc-Gly (178 mg, 0.6 mmol), dimethylaminopyridine (73 mg, 0.6 mmol) and paclitaxel (manufactured and sold by DABUR, India, 427 mg, 0.5 mmol) were dissolved in 20 ml of methylene chloride, to thereby obtain a solution. To the obtained solution was added N,N'-diisopropylcarbodiimide (76 mg, 0.6 mmol) and stirred overnight at room temperature, to thereby obtain a reaction mixture. The obtained reaction mixture was evaporated to dryness, to thereby obtain a residue. The obtained residue was purified by silica gel column chromatography (silica gel: Art No. 9385, Silica gel 60, 200–400 mesh, manufactured and sold by E. Merck, Darmstadt, Germany, column: 4.0×30 cm, eluent: methylene chloride/acetonitrile=70/30), to thereby obtain 499 mg of 2'-Fmoc-Gly-paclitaxel. 420 mg of the obtained compound was dissolved in 10 ml of N,N-dimethylformamide, followed by adding thereto 2 ml of piperidine at room temperature, to thereby obtain a mixture. The obtained mixture was stirred for 5 minutes to effect a reaction for removing the Fmoc group, to thereby obtain a reaction mixture. The obtained reaction mixture was evaporated to dryness, to thereby obtain a residue. The obtained residue was purified by silica gel column chromatography (silica gel: Art No. 9385, Silica gel 60, 200–400 mesh, manufactured and sold by E. Merck, Darmstadt, Germany, column: 4.0×50 cm, eluent: acetonitrile/methylene chloride=80/20) to thereby obtain 141 mg of compound (2).

$^1$H-NMR (DMSO-d$_6$): δ1.01 (s, 3H, Me-17), 1.05 (s, 3H, Me-16), 1.52 (dd, 1H, J=14.6, 9.2 Hz, H-14b), 1.51 (s, 3H, Me-19), 1.65 (t, 1H, J=11.6 Hz, H-6b), 1.81 (dd, 1H, J=15.5, 9.6 Hz, H-14a), 1.86 (s, 3H, Me-18), 2.11 (s, 3H, Ac-10), 2.23 (s, 3H, Ac-4), 2.32 (m, 1H, H-6a), 3.58 (d, 1H, J=7.0 Hz, H-3), 3.96–4.07 (m, 3H, GlyCH$_2$, H-20), 4.10 (dd, 1H, J=6.7, 10.7 Hz, H-7), 4.63 (s, 1H, OH-1), 4.90 (brs, 1H, OH-7), 4.91 (dd, 1H, J=4.9 Hz, H-5), 5.43 (d, 1H, J 7.0 Hz, H-2), 5.46 (d, 1H, J=8.2 Hz, H-2'), 5.58 (t, 1H, J=8.4 Hz, H-3'), 5.87 (t, 1H, J=8.6 Hz, H-13), 6.30 (s, 1H, H-10), 7.19–8.00 (aromatic, 15H), 8.40 (brs, 2H, GlyNH$_2$), 9.25 (d, 1H, J=8.6 Hz, CONH-3')

HRMS: m/z 911.3604 (M+H)$^+$: the molecular weight calculated for C$_{49}$H$_{55}$O$_{15}$N$_2$ 911.3602

(Step 3) Production of carboxymethylated dextran-2'-Gly-paclitaxel (3)

100 mg of carboxymethylated dextran sodium salt (1) obtained in step 1 was dissolved in 2 ml of water. To the resultant solution was added 2 ml of N,N-dimethylformamide while cooling over ice. To the resultant mixture were added 0.5 ml of a solution containing 30 mg of 2'-Gly-paclitaxel (2) obtained in step 2, which was dissolved in a mixture of water and N,N-dimethylformamide (1:1), and 0.5 ml of a solution containing 100 mg of 1-ethoxycarbonyl-2-ethoxy-1,2-dihydroquinoline dissolved in N,N-dimethylformamide, followed by stirring at room temperature for two hours, to thereby obtain a reaction mixture. The obtained reaction mixture was poured into 100 ml of ethanol, to thereby generate a precipitate. The generated precipitate was collected and dissolved in 10 ml of purified water. The resultant solution was poured into 100 ml of ethanol, to thereby generate a precipitate. The generated precipitate was collected and washed with acetone and ether successively, to thereby obtain 105 mg of compound (3) (drug complex) as a white amorphous substance.

Figure 3:
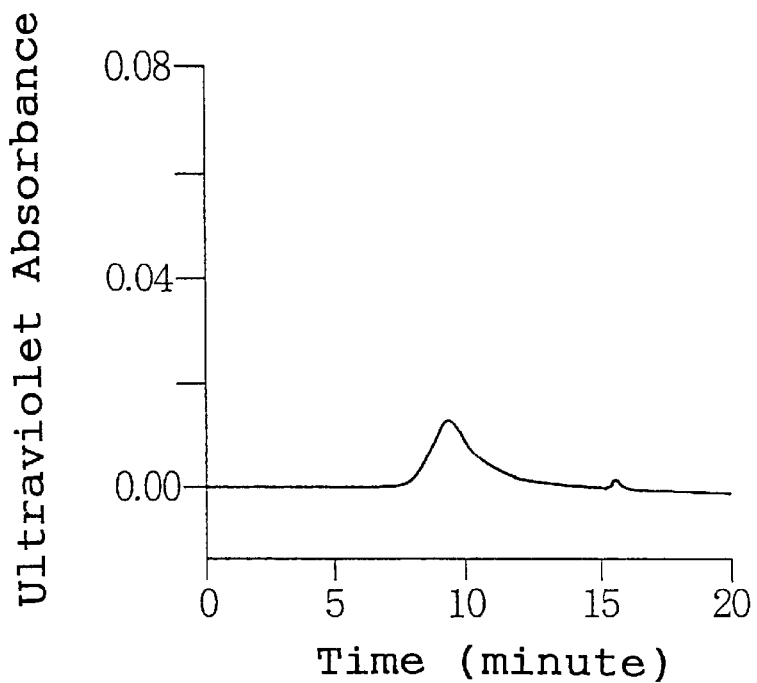
FIG. 3 is a chart showing the gel filtration chromatogram of carboxymethylated dextran-2'-Gly-paclitaxel (3) obtained in Example 1, wherein the chromatogram was obtained using an ultraviolet detector (wavelength: 227 nm).
Figure 4:
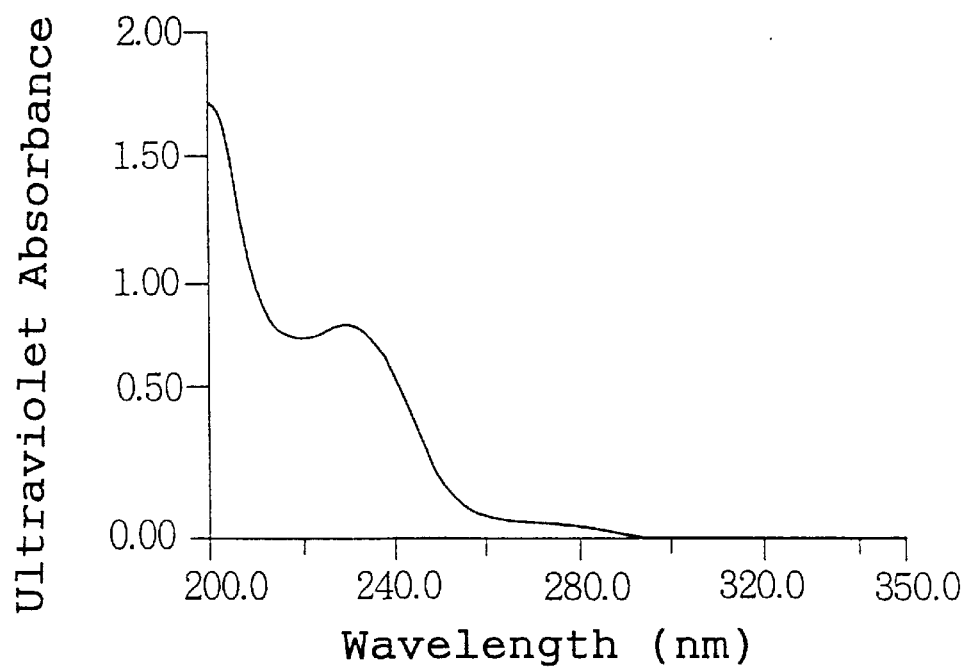
FIG. 4 is a chart showing the ultraviolet absorption spectrum of carboxymethylated dextran-2'-Gly-paclitaxel (3) obtained in Example 1 (concentration: 672 µg/ml, solvent: water).

The amount of the drug introduced into compound (3) was calculated from the ultraviolet absorbance at 254 nm, and found to be 3.7% by weight, based on the weight of compound (3). The gel filtration chromatogram of compound (3) was obtained using an ultraviolet detector (wavelength: 227 nm), and is shown in FIG. 3. The ultraviolet absorption spectrum of compound (3) is shown in FIG. 4.

(Step 4) Production of propanoyl-2'-Gly-paclitaxel (4)

Propionic acid (7.4 mg, 0.1 mmol) was dissolved in 2 ml of N,N-dimethylformamide, to thereby obtain a solution. To the obtained solution were added 2'-Gly-paclitaxel (2) (45 mg, 0.05 mmol) obtained in step 2, 4-dimethylaminopyridine (12 mg, 0.1 mmol) and N,N'-diisopropylcarbodiimide (12.6 mg, 0.1 mmol), followed by stirring overnight at room temperature, to thereby obtain a reaction mixture. The obtained reaction mixture was evaporated to dryness, to thereby obtain a residue. The obtained residue was purified by silica gel column chromatography (silica gel: Art No. 9365, Silica gel 60, 200–400 mesh, manufactured and sold by E. Merck, Darmstadt, Germany, eluent: methylene chloride/acetonitrile=70/30) to thereby obtain 30 mg of compound (4) (drug complex).

$^1$H-NMR (DMSO-d$_6$): δ1.01 (s, 3H, Me-17), 1.05 (s, 3H, Me-16), 1.06 (t, 3H, J -=7.5 Hz, Me-Pr), 1.52 (dd, 1H, J=14.6, 9.2 Hz, H-14b), 1.51 (s, 3H, Me-19), 1.65 (t, 1H, J=11.6 Hz, H-6b), 1.81 (dd, 1H, J=15.5, 9.6 Hz, H-14a), 1.86 (s, 3H, Me-18), 2.11 (s, 3H, Ac-10), 2.23 (s, 3H, Ac-4), 2.32 (m, 1H, H-6a), 2.40 (q, 2H, J=7.5 Hz, CH$_2$-Pr), 3.58 (d, 1H, J=7.0 Hz, H-3), 3.96–4.07 (m, 3H, GlyCH$_2$, H-20), 4.10 (dd, 1H, J=6.7, 10.7 Hz, H-7), 4.63 (s, 1H, OH-1), 4.90 (brs, 1H, OH-7), 4.91 (dd, 1H, J=4.9 Hz, H-5), 5.43 (d, 1H, J=7.0 Hz, H-2), 5.46 (d, 1H, J=8.2 Hz, H-2'), 5.58 (t, 1H, J=8.4 Hz, H-3'), 5.87 (t, 1H, J=8.6 Hz, H-13), 6.30 (s, 1H, H-10), 7.19–8.00 (aromatic, 15H), 8.40 (brs, 2H, GlyNH$_2$), 9.25 (d, 1H, J=8.6 Hz, CONH-3')

(Step 5) Production of PEG-2'-Gly-paclitaxel (5)

Figure 5:
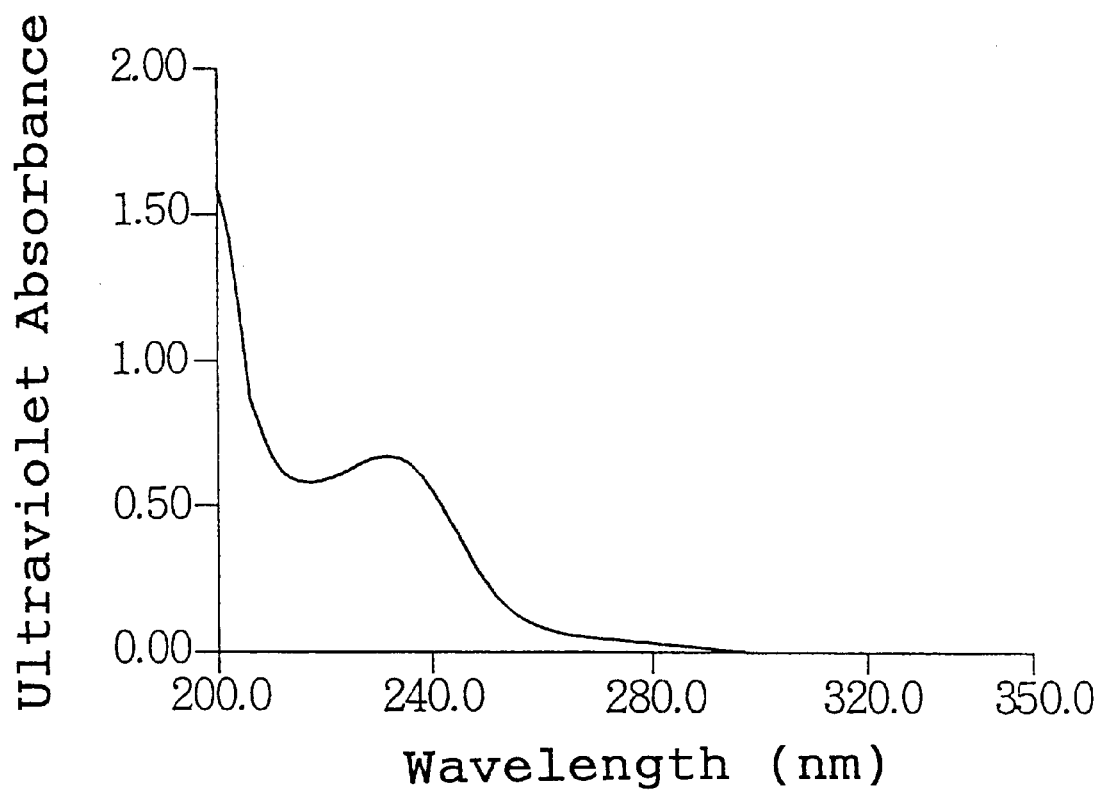
FIG. 5 is a chart showing the ultraviolet absorption spectrum of PEG-2'-Gly-paclitaxel (5) obtained in Example 1 (concentration: 205 µg/ml, solvent: water).

Carboxymethylated PEG (CM-PEG) was prepared from PEG [poly(ethylene glycol)methyl ether, Mw=5,000, manufactured and sold by Aldrich, U.S.A] using ethyl monobromoacetate and tBuOK, according to the methods described in Journal of Controlled Release, 10, 145–154 (1989) and Polymer Bulletin, 18, 487–493 (1987). The prepared CM-PEG (500 mg, 0.1 mmol) was dissolved in 5 ml of N,N-dimethylformamide, to thereby obtain a solution. To the obtained solution were added 2'-Gly-paclitaxel (2) (45 mg, 0.05 mmol) obtained in step 2, 4-dimethylaminopyridine (12mg, 0.1 mmol) and N,N'-diisopropylcarbodiimide (12.6 mg, 0.1 mmol), followed by stirring overnight at room temperature, to thereby obtain a reaction mixture. The obtained reaction mixture was evaporated to dryness, to thereby obtain a residue. The obtained residue was dissolved into 2-propanol while heating, and the resultant solution was subjected to recrystallization, to thereby generate a precipitate. The generated precipitate was washed with cooled 2-propanol and ether successively, followed by drying under reduced pressure, to thereby obtain 150 mg of compound (5) (drug complex). The ultraviolet absorption spectrum of compound (5) is shown in FIG. 5.

EXAMPLE 2

(Step 1) Production of 2'-Ala-paclitaxel (6)

Z-Ala (145 mg, 0.65 mmol), dimethylaminopyridine (79 mg, 0.65 mmol) and paclitaxel (manufactured and sold by DABUR, India, 427 mg, 0.5 mmol) were dissolved in 20 ml of methylene chloride, to thereby obtain a solution. To the obtained solution was added N,N'-diisopropylcarbodiimide (82 mg, 0.65 mmol) and stirred overnight at room temperature, to thereby obtain a reaction mixture. The obtained reaction mixture was evaporated to dryness, to thereby obtain a residue. The obtained residue was purified by silica gel column chromatography (silica gel: Art No. 9385, Silica gel 60, 200–400 mesh, manufactured and sold by E. Merck, Darmstadt, Germany, column: 4.0×30 cm, eluent: methylene chloride/acetonitrile=70/30), to thereby obtain 431 mg of 2'-Z-Ala-paclitaxel. 400 mg of the obtained compound was dissolved in 20 ml of dioxane, to thereby obtain a mixture. To the obtained mixture was added 200 mg of a palladium-carbon catalyst, followed by stirring for 4 hours in an atmosphere of hydrogen, to thereby obtain a reaction mixture. The obtained reaction mixture was subjected to filtration to remove the catalyst, thereby obtaining a solution. The obtained solution was evaporated to dryness under reduced pressure, to thereby obtain a residue. The obtained residue was purified by silica gel column chromatography (silica gel: Art No. 9385, Silica gel 60, 200–400 mesh, manufactured and sold by E. Merck, Darmstadt, Germany, column: 2.0×30 cm, eluent: methylene chloride/methanol/acetonitrile=95/5/5), to thereby obtain 231 mg of compound (6).

$^1$H-NMR (DMSO-d$_6$): δ1.01 (s, 3H, Me-17), 1.03 (s, 3H, Me-16), 1.14 (s, 3H, Me-Ala), 1.51 (s, 3H, Me-19), 1.61 (dd, 1H, J=15.6, 9.2 Hz, H-14b), 1.64 (t, 1H, J=12.8 Hz, H-6b), 1.81 (s, 3H, Me-18), 1.88 (dd, 1H, J=15.3, 9.5 Hz, H-14a), 2.11 (s, 3H, Ac-10), 2.27 (s, 3H, Ac-4), 2.33 (m, 1H, H-6a), 3.52 (q, 1H, J=7.0 Hz, H-Ala), 3.60 (d, 1H, J=7.3 Hz, H-3), 4.02 (d, 1H, J=15.0 Hz, H-20), 4.03 (d, 1H, J=15.0 Hz, H-20), 4.12 (ddd, 1H, J=6.6, 6.6, 17.4 Hz, H-7), 4.66 (s, 1H, OH-1), 4.91 (d, 1H, J=6.6 Hz, OH-7), 4.92 (dd, 1H, J=9.8 Hz, H-5), 5.35 (t, 1H, J=8.6 Hz, H-2$^1$), 5.43 (d, 1H, J=7.0 Hz, H-2), 5.64 (t, 1H, J-8.6 Hz, H-3'), 5.87 (t, 1H, J=9.2 Hz, H-13), 6.30 (s, 1H, H-10), 7.20–8.00 (aromatic, 15H), 9.17 (d, 1H, J=8.9 Hz, CONH-3')

HRMS: m/z 925.3797 (M+H)$^+$: the molecular weight calculated for C$_{50}$H$_{57}$O$_{15}$N$_2$ 925.3759

(Step 2) Production of carboxymethylated dextran-2'-Ala-paclitaxel (7)

100 mg of carboxymethylated dextran sodium salt (1) obtained in Example 1 was dissolved in 2 ml of water. To the resultant solution was added 2 ml of N,N-dimethylformamide while cooling over ice. To the resultant mixture were added 0.5 ml of a solution containing 30 mg of 2'-Ala-paclitaxel (6) obtained in step 1, which was dissolved in a mixture of water and N,N-dimethylformamide (1:1), and 0.5 ml of a solution containing 100 mg of 1-ethoxycarbonyl-2-ethoxy-1,2-dihydroquinoline dissolved in N,N-dimethylformamide, followed by stirring at room temperature for two hours, to thereby obtain a reaction mixture. The obtained reaction mixture was poured into 100 ml of ethanol, to thereby generate a precipitate. The generated precipitate was collected and dissolved in 10 ml of purified water. The resultant solution was poured into 100 ml of ethanol, to thereby generate a precipitate. The generated precipitate was collected and washed with acetone and ether successively, to thereby obtain 105 mg of compound (7) (drug complex) as a white amorphous substance.

Figure 6:
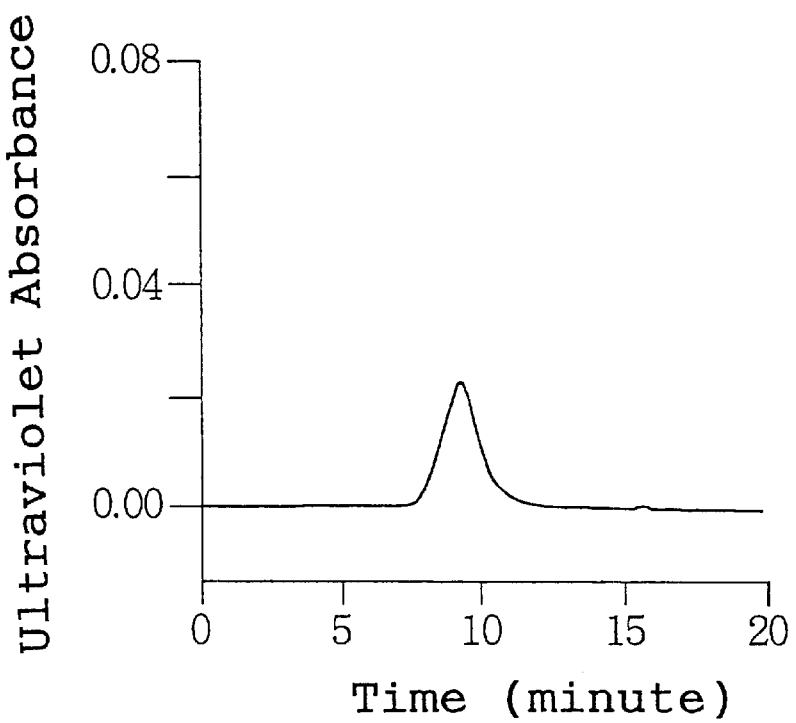
FIG. 6 is a chart showing the gel filtration chromatogram of carboxymethylated dextran-2'-Ala-paclitaxel (7) obtained in Example 2, wherein the chromatogram was obtained using an ultraviolet detector (wavelength: 227 nm).
Figure 7:
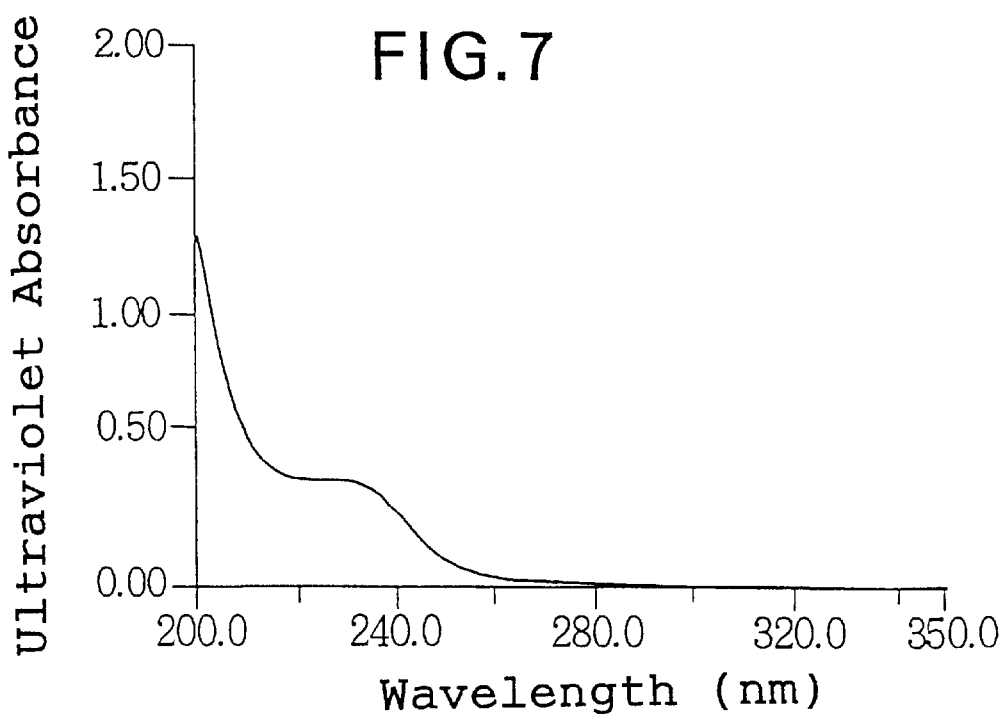
FIG. 7 is a chart showing the ultraviolet absorption spectrum of carboxymethylated dextran-2'-Ala-paclitaxel (7) obtained in Example 2 (concentration: 698 µg/ml, solvent: water).

The amount of the drug introduced into compound (7) was calculated from the ultraviolet absorbance at 254 nm, and found to be 1.7% by weight, based on the weight of compound (7). The gel filtration chromatogram of compound (7) was obtained using an ultraviolet detector (wavelength: 227 nm), and is shown in FIG. 6. The ultraviolet absorption spectrum of compound (7) is shown in FIG. 7.

(Step 3) Production of propanoyl-2'-Ala-paclitaxel (8)

Propionic acid (7.4 mg, 0.1 mmol) was dissolved in 2 ml of N,N-dimethylformamide, to thereby obtain a solution. To the obtained solution were added 2'-Ala-paclitaxel (6) (45 mg, 0.05 mmol) obtained in step 1, 4-dimethylaminopyridine (12mg, 0.1 mmol) and N,N'-diisopropylcarbodiimide (12.6 mg, 0.1 mmol), followed by stirring overnight at room temperature, to thereby obtain a reaction mixture. The obtained reaction mixture was evaporated to dryness, to thereby obtain a residue. The obtained residue was purified by silica gel column chromatography (silica gel: Art No. 9385, Silica gel 60, 200–400 mesh, manufactured and sold by E. Merck, Darmstadt, Germany, eluent: methylene chloride/acetonitrile=70/30) to thereby obtain 32 mg of compound (8) (drug complex).

$^1$H-NMR (DMSO-$d_6$): δ1.01 (s, 3H, Me-17), 1.03 (s, 3H, Me-16), 1.06 (t, 3H, J=7.5 Hz, Me-Pr), 1.14 (s, 3H, Me-Ala), 1.51 (s, 3H, Me-19), 1.61 (dd, 1H, J=15.6, 9.2 Hz, H-14b), 1.64 (t, 1H, J=12.8 Hz, H-6b), 1.81 (s, 3H, Me-18), 1.88 (dd, 1H, J=15.3, 9.5 Hz, H-14a), 2.11 (s, 3H, Ac-10), 2.27 (s, 3H, Ac-4), 2.33 (m, 1H, H-6a), 2.40 (q, 2H, J=7.5 Hz, CH$_2$-Pr), 3.52 (q, 1H, J=7.0 Hz, H-Ala), 3.60 (d, 1H, J=7.3 Hz, H-3), 4.02 (d, 1H, J=15.0 Hz, H-20), 4.03 (d, 1H, J=15.0 Hz, H-20), 4.12 (ddd, 1H, J=6.6, 6.6, 17.4 Hz, H-7), 4.66 (s, 1H, OH-1), 4.91 (d, 1H, J=6.6 Hz, OH-7), 4.92 (dd, 1H, J=9.8 Hz, H-5), 5.35 (d, 1H, J=8.6 Hz, H-2'), 5.43 (d, 1H, J=7.0 Hz, H-2), 5.64 (t, 1H, J=8.6 Hz, H-3'), 5.87 (t, 1H, J=9.2 Hz, H-13), 6.30 (s, 1H, H-10), 7.20–8.00 (aromatic, 15H), 9.17 (d, 1H, J=8.9 Hz, CONH-3')

(Step 4) Production of PEG-2'-Ala-paclitaxel (9)

Figure 8:
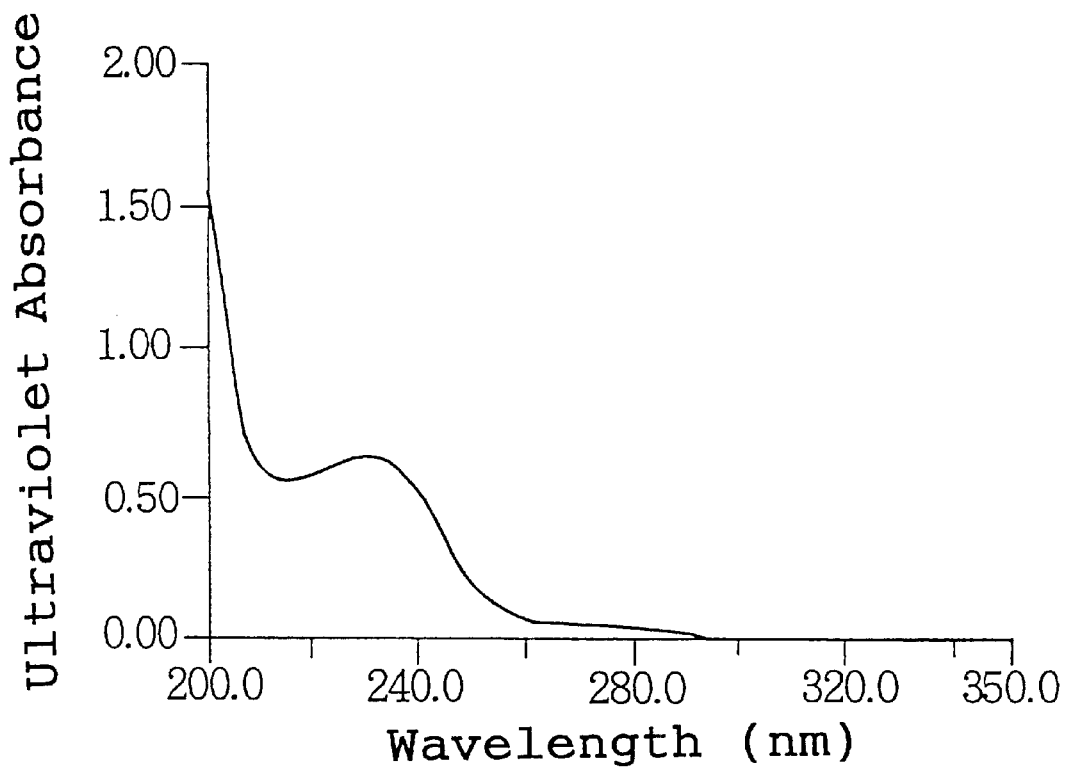
FIG. 8 is a chart showing the ultraviolet absorption spectrum of PEG-2'-Ala-paclitaxel (9) obtained in Example 2 (concentration: 204 µg/ml, solvent: water).

CM-PEG (500 mg, 0.1 mmol) obtained in step 5 of Example 1 was dissolved in 5 ml of N,N-dimethylformamide, to thereby obtain a solution. To the obtained solution were added 2'-Ala-paclitaxel (6) (45 mg, 0.05 mmol) obtained in step 1, 4-dimethylaminopyridine (12 mg, 0.1 mmol) and N,N'-diisopropylcarbodiimide (12.6 mg, 0.1 mmol), followed by stirring overnight at room temperature, to thereby obtain a reaction mixture. The obtained reaction mixture was evaporated to dryness, to thereby obtain a residue. The obtained residue was dissolved into 2-propanol while heating, and the resultant solution was subjected to recrystallization, to thereby generate a precipitate. The generated precipitate was washed with cooled 2-propanol and ether successively, followed by drying under reduced pressure, to thereby obtain 160 mg of compound (9) (drug complex). The ultraviolet absorbance spectrum of compound (9) is shown in FIG. 8.

EXAMPLE 3

(Step 1) Production of 2'-Leu-paclitaxel (10)

Z-Leu (172 mg, 0.65 mmol), dimethylaminopyridine (79 mg, 0.65 mmol) and paclitaxel (manufactured and sold by DABUR, India, 427 mg, 0.5 mmol) were dissolved in 20 ml of methylene chloride, to thereby obtain a solution. To the obtained solution was added N,N'-diisopropylcarbodiimide (82 mg, 0.65 mmol) and stirred overnight at room temperature, to thereby obtain a reaction mixture. The obtained reaction mixture was evaporated to dryness, to thereby obtain a residue. The obtained residue was purified by silica gel column chromatography (silica gel: Art No. 9385, Silica gel 60, 200–400 mesh, manufactured and sold by E. Merck, Darmstadt, Germany, column: 4.0×30 cm, eluent: methylene chloride/acetonitrile=70/30), to thereby obtain 454 mg of 2'-Z-Leu-paclitaxel. 400 mg of the obtained compound was dissolved in 20 ml of dioxane, to thereby obtain a mixture. To the obtained mixture was added 200 mg of a palladium-carbon catalyst, followed by stirring for 4 hours in an atmosphere of hydrogen, to thereby obtain a reaction mixture. The obtained reaction mixture was subjected to filtration to remove the catalyst, thereby obtaining a solution. The obtained solution was evaporated to dryness under reduced pressure, to thereby obtain a residue. The obtained residue was purified by silica gel column chromatography (silica gel: Art No. 9385, Silica gel 60, 200–400 mesh, manufactured and sold by E. Merck, Darmstadt, Germany, column: 4.0×30 cm, eluent: methylene chloride/methanol/acetonitrile=95/5/5), to thereby obtain 289 mg of compound (10).

$^1$H-NMR (DMSO-$d_6$): δ0.66 (d, 3H, Me-Leu), 0.70 (d, 3H, Me-Leu), 1.01 (s, 3H, Me-17), 1.03 (s, 3H, Me-16), 1.26 (ddd, 1H, J=6.4, 8.5, 13.4 Hz, H-Leu), 1.36 (ddd, 1H, J=5.8, 7.6, 13.4 Hz, H-Leu), 1.51 (s, 3H, Me-19), 1.56 (dd, 1H, J=15.3, 9.0 Hz, H-14b), 1.64 (m, 1H, H-6b), 1.67 (m, 1H, H-Leu), 1.79 (s, 3H, Me-18), 1.84 (dd, 1H, J=15.3, 9.5 Hz, H-14a), 2.10 (s, 3H, Ac-10), 2.25 (s, 3H, Ac-4), 2.33 (ddd, 1H, J=14.7, 9.5, 6.4 Hz, H-6a), 3.38 (dd, 1H, J=8.6, 5.8 Hz, H-Leu), 3.59 (d, 1H, J=7.0 Hz, H-3), 4.01 (d, 1H, J=16.8 Hz, H-20), 4.03 (d, 1H, J=16.8 Hz, H-20), 4.12 (ddd, 1H, J=6.9, 6.9, 11.0 Hz, H-7), 4.64 (s, 1H, OH-1), 4.90 (d, 1H, J=7.0 Hz, OH-7), 4.92 (d, 1H, J=10.1 Hz, H-5), 5.34 (d, 1H, J=9.2 Hz, H-2'), 5.42 (d, 1H, J=7.0 Hz, H-2), 5.62 (t, 1H, J=9.0 Hz, H-3'), 5.86 (t, 1H, J=9.2 Hz, H-13), 6.30 (s, 1H, H-10), 7.20–8.00 (aromatic, 15H), 9.16 (d, 1H, J=8.9 Hz, CONH-3')

HRMS: m/z 967.4321 (M+H)$^+$: the molecular weight calculated for $C_{53}H_{63}O_{15}N_2$ 967.4228

(Step 2) Production of carboxymethylated dextran-2'-Leu-paclitaxel (11)

100 mg of carboxymethylated dextran sodium salt (1) obtained in Example 1 was dissolved in 2 ml of water. To the resultant solution was added 2 ml of N,N-dimethylformamide while cooling over ice. To the resultant mixture were added 0.5 ml of a solution containing 30 mg of 2'-Leu-paclitaxel (10) obtained in step 2, which was dissolved in a mixture of water and N,N-dimethylformamide (1:1), and 0.5 ml of a solution containing 100 mg of 1-ethoxycarbonyl-2-ethoxy-1,2-dihydroquinoline dissolved in N,N-dimethylformamide, followed by stirring at room temperature for two hours, to thereby obtain a reaction mixture. The obtained reaction mixture was poured into 100 ml of ethanol, to thereby generate a precipitate. The generated precipitate was collected and dissolved in 10 ml of purified water. The resultant solution was poured into 100 ml of ethanol, to thereby generate a precipitate. The generated precipitate was collected and washed with acetone and ether successively, to thereby obtain 106 mg of compound (11) (drug complex) as a white amorphous substance.

Figure 9:
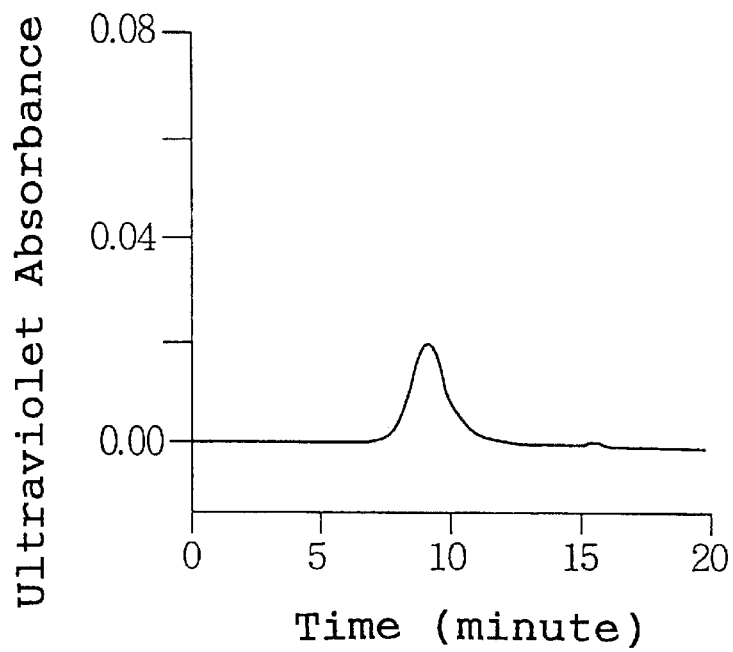
FIG. 9 is a chart showing the gel filtration chromatogram of carboxymethylated dextran-2'-Leu-paclitaxel (11) obtained in Example 3, wherein the chromatogram was obtained using an ultraviolet detector (wavelength: 227 nm).
Figure 10:
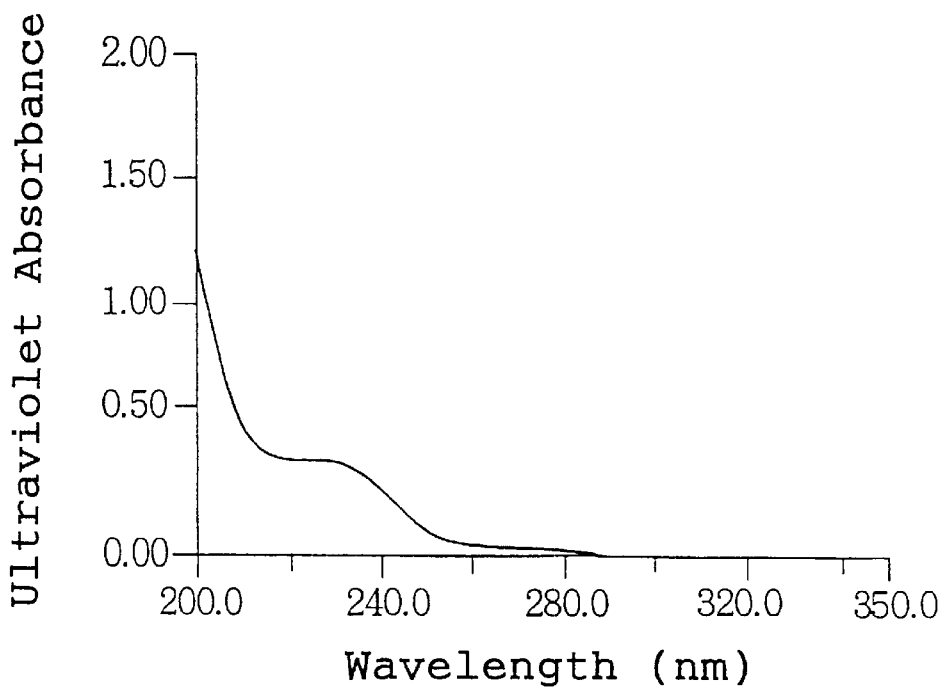
FIG. 10 is a chart showing the ultraviolet absorption spectrum of carboxymethylated dextran-2'-Leu-paclitaxel (11) (concentration: 644 pm/ml, solvent: water).

The amount of the drug introduced into compound (11) was calculated from the ultraviolet absorbance at 254 nm, and found to be 1.7% by weight, based on the weight of compound (11). The gel filtration chromatogram of compound (11) was obtained using an ultraviolet detector (wavelength: 227 nm), and is shown in FIG. 9. The ultraviolet absorption spectrum of compound (11) is shown in FIG. 10.

(Step 3) Production of propanoyl-2'-Leu-paclitaxel (12)

Propionic acid (7.4 mg, 0.1 mmol) was dissolved in 2 ml of N,N-dimethylformamide, to thereby obtain a solution. To the obtained solution were added 2'-Leu-paclitaxel (10) (45 mg, 0.05 mmol) obtained in step 1, 4-dimethylaminopyridine (12 mg, 0.1 mmol) and N,N'-diisopropylcarbodiimide (12.6 mg, 0.1 mmol), followed by stirring overnight at room temperature, to thereby obtain a reaction mixture. The obtained reaction mixture was evaporated to dryness, to thereby obtain a residue. The obtained residue was purified by silica gel column chromatography (silica gel: Art No. 9385, Silica gel 60, 200–400 mesh, manufactured and sold by E. Merck, Darmstadt, Germany, eluent: methylene chloride/acetonitrile=70/30), to thereby obtain 34 mg of compound (12) (drug complex).

$^1$H-NMR (DMSO-d$_6$): δ0.66 (d, 3H, Me-Leu), 0.70 (d, 3H, Me-Leu), 1.01 (s, 3H, Me-17), 1.03 (s, 3H, Me-16), 1.06 (t, 3H, J=7.5 Hz, Me-Pr), 1.26 (ddd, 1H, J=6.4, 8.5, 13.4 Hz, H-Leu), 1.36 (ddd, 1H, J=5.8, 7.6, 13.4 Hz, H-Leu), 1.51 (s, 3H, Me-19), 1.56 (dd, 1H, J=15.3, 9.0 Hz, H-14b), 1.64 (m, 1H, H-6b), 1.67 (m, 1H, H-Leu), 1.79 (s, 3H, Me-18), 1.84 (dd, 1H, J=15.3, 9.5 Hz, H-14a), 2.10 (s, 3H, Ac-10), 2.25 (s, 3H, Ac-4), 2.33 (ddd, 1H, J=14.7, 9.5, 6.4 Hz, H-6a), 2.40 (q, 2H, J=7.5 Hz, CH$_2$—Pr), 3.38 (dd, 1H, J=8.6, 5.8 Hz, H-Leu), 3.59 (d, 1H, J=7.0 Hz, H-3), 4.01 (d, 1H, J=16.8 Hz, H-20), 4.03 (d, 1H, J=16.8 Hz, H-20), 4.12 (ddd, 1H, J=6.9, 6.9, 11.0 Hz, H-7), 4.64 (s, 1H, OH-1), 4.90 (d, 1H, J=7.0 Hz, OH-7), 4.92 (d, 1H, J=10.1 Hz, H-5), 5.34 (d, 1H, J=9.2 Hz, H-2'), 5.42 (d, 1H, J=7.0 Hz, H-2), 5.62 (t, 1H, J=9.0 Hz, H-3'), 5.86 (t, 1H, J=9.2 Hz, H-13), 6.30 (s, 1H, H-10), 7.20–8.00 (aromatic, 15H), 9.16 (d, 1H, J=8.9 Hz, CONH-3')

(Step 4) Production of PEG-2'-Leu-paclitaxel (13)

Figure 11:
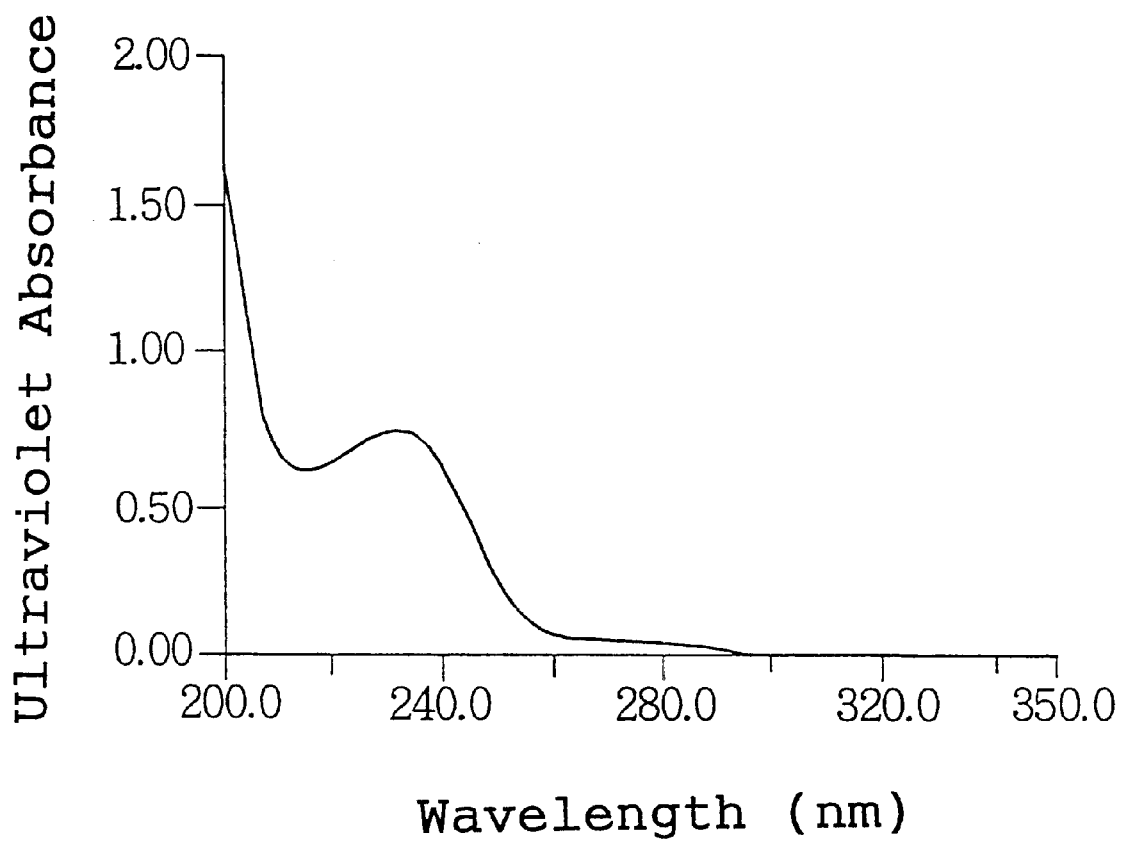
FIG. 11 is a chart showing the ultraviolet absorption spectrum of PEG-2'-Leu-paclitaxel (13) obtained in Example 3 (concentration: 209 µg/ml, solvent: water).

CM-PEG (500 mg, 0.1 mmol) obtained in step 5 of Example 1 was dissolved in 5 ml of N,N-dimethylformamide, to thereby obtain a solution. To the obtained solution were added 2'-Leu-paclitaxel (10) (45 mg, 0.05 mmol) obtained in step 1, 4-dimethylaminopyridine (12 mg, 0.1 mmol) and N,N'-diisopropylcarbodiimide (12.6 mg, 0.1 mmol), followed by stirring overnight at room temperature, to thereby obtain a reaction mixture. The obtained reaction mixture was evaporated to dryness, to thereby obtain a residue. The obtained residue was dissolved into 2-propanol while heating, and the resultant solution was subjected to recrystallization, to thereby generate a precipitate. The generated precipitate was washed with cooled 2-propanol and ether successively, followed by drying under reduced pressure, to thereby obtain 145 mg of compound (13) (drug complex). The ultraviolet absorption spectrum of compound (13) is shown in FIG. 11.

EXAMPLE 4

(Step 1) Production of 2'-Ile-paclitaxel (14)

Fmoc-Ile (212 mg, 0.6 mmol), dimethylaminopyridine (73 mg, 0.6 mmol) and paclitaxel (manufactured and sold by DABUR, India, 427 mg, 0.5 mmol) were dissolved in 20 ml of methylene chloride, to thereby obtain a solution. To the obtained solution was added N,N'-diisopropylcarbodiimide (76 mg, 0.6 mmol) and stirred overnight at room temperature, to thereby obtain a reaction mixture. The obtained reaction mixture was evaporated to dryness, to thereby obtain a residue. The obtained residue was purified by silica gel column chromatography (silica gel: Art No. 9385, Silica gel 60, 200–400 mesh, manufactured and sold by E. Merck, Darmstadt, Germany, column: 2.0×30 cm, eluent: methylene chloride/acetonitrile=70/30), to thereby obtain 552 mg of 2'-Fmoc-Ile-paclitaxel. 470 mg of the obtained compound was dissolved in 10 ml of DMF, followed by adding thereto 2 ml of piperidine at room temperature, to thereby obtain a mixture. The obtained mixture was stirred for 5 minutes to effect a reaction for removing Fmoc group, thereby obtaining a reaction mixture. The obtained reaction mixture was evaporated to dryness under reduced pressure, to thereby obtain a residue. The obtained residue was purified by silica gel column chromatography (silica gel: Art No. 9385, Silica gel 60, 200–400 mesh, manufactured and sold by E. Merck, Darmstadt, Germany, column: 4.0×30 cm, eluent: methylene chloride/methanol/acetonitrile=95/5/5) to thereby obtain 353 mg of compound (14).

$^1$H-NMR (DMSO-d$_6$): δ0.62 (t, 3H, J=7.5 Hz, Me-Ile), 0.81 (d, 3H, J=6.7 Hz, Me-Ile), 1.01 (s, 3H, Me-17), 1.03 (s, 3H, Me-16), 1.07 (ddd, 1H, J=14.4, 7.3, 4.9 Hz, H-Ile), 1.32 (ddd, 1H, J=13.4, 7.6, 4.6 Hz, H-Ile), 1.51 (s, 3H, Me-19), 1.56 (dd, 1H, J=15.3, 9.2 Hz, H-14b), 1.56–1.61 (m, 1H, H-Ile), 1.64 (dd, 1H, J=13.7, 3.1 Hz, H-6b), 1.79 (s, 3H, Me-18), 1.87 (dd, 1H, J=15.3, 9.8 Hz, H-14a), 2.10 (s, 3H, Ac-10), 2.29 (s, 3H, Ac-4), 2.33 (ddd, 1H, J=14.4, 9.6, 6.4 Hz, H-6a), 3.60 (d, 1H, J=7.3 Hz, H-3), 3.60–3.67 (m, 1H, H-Ile), 4.02 (d, 1H, J=16.6 Hz, H-20), 4.03 (d, 1H, J=16.6 Hz, H-20), 4.12 (ddd, 1H, J=10.8, 6.7, 6.7 Hz, H-7), 4.64 (s, 1H, OH-1), 4.90 (d, 1H, J=7.0, OH-7), 4.92 (d, 1H, J=9.8 Hz, H-5), 5.37 (d, 1H, J=8.9 Hz, H-2'), 5.43 (d, 1H, J=7.3 Hz, H-2), 5.64 (t, 1H, J=8.7 Hz, H-3'), 5.85 (dt, 1H, J=0.9, 9.2 Hz, H-13), 6.30 (s, 1H, H-10), 7.20–8.00 (aromatic, 15H), 9.15 (d, 1H, J=9.2 Hz, CONH-3')

HRMS: m/z 967.4234 (M+H)$^+$: the molecular weight calculated for C$_{53}$H$_{63}$O$_{15}$N$_2$ 967.4228

(Step 2) Production of carboxymethylated dextran-2'-Ile-paclitaxel (15)

100 mg of carboxymethylated dextran sodium salt (1) obtained in Example 1 was dissolved in 2 ml of water. To the resultant solution was added 2 ml of N,N-dimethylformamide while cooling over ice. To the resultant mixture were added 0.5 ml of a solution containing 30 mg of 2'-Ile-paclitaxel (14) obtained in step 2, which was dissolved in a mixture of water and N,N-dimethylformamide (1:1), and 0.5 ml of a solution containing 100 mg of 1-ethoxycarbonyl-2-ethoxy-1,2-dihydroquinoline dissolved in N,N-dimethylformamide, followed by stirring at room temperature for two hours, to thereby obtain a reaction mixture. The obtained reaction mixture was poured into 100 ml of ethanol, to thereby generate a precipitate. The generated precipitate was collected and dissolved in 10 ml of purified water. The resultant solution was poured into 100 ml of ethanol, to thereby generate a precipitate. The generated precipitate was collected and washed with acetone and ether successively, to thereby obtain 105 mg of compound (15) (drug complex) as a white amorphous substance.

Figure 12:
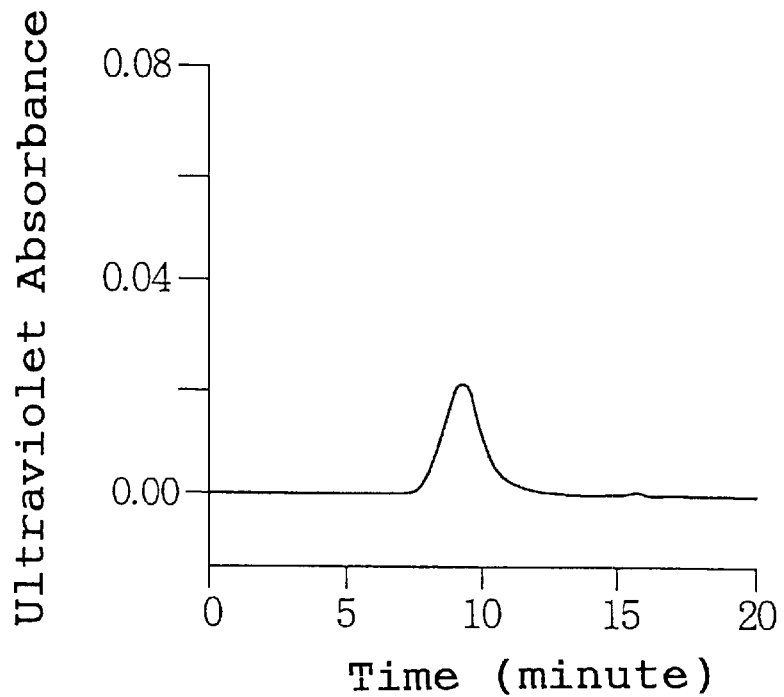
FIG. 12 is a chart showing the gel filtration chromatogram of carboxymethylated dextran-2'-Ile-paclitaxel (15) obtained in Example 4, wherein the chromatogram was obtained using an ultraviolet detector (wavelength: 227 nm).
Figure 13:
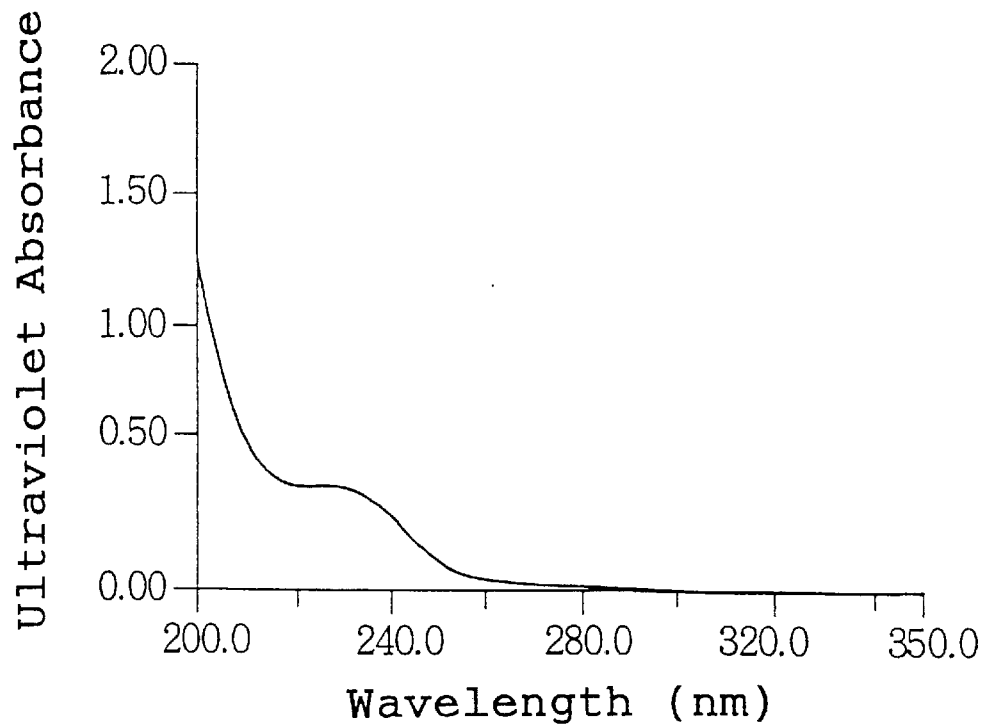
FIG. 13 is a chart showing the ultraviolet absorption spectrum of carboxymethylated dextran-2'-Ile-paclitaxel (15) obtained in Example 4 (concentration: 628 µg/ml, solvent: water).

The amount of the drug introduced into compound (15) was calculated from the ultraviolet absorbance at 254 nm, and found to be 1.6% by weight, based on the weight of compound (15). The gel filtration chromatogram of compound (15) was obtained using an ultraviolet detector (wavelength: 227 nm), and is shown in FIG. 12. The ultraviolet absorption spectrum of compound (15) is shown in FIG. 13.

(Step 3) Production of propanoyl-2'-Ile-paclitaxel (16)

Propionic acid (7.4 mg, 0.1 mmol) was dissolved in 2 ml of N,N-dimethylformamide, to thereby obtain a solution. To the obtained solution were added 2'-Ile-paclitaxel (14) (45 mg, 0.05 mmol) obtained in step 1, 4-dimethylaminopyridine (12 mg, 0.1 mmol) and N,N'-diisopropylcarbodiimide (12.6 mg, 0.1 mmol), followed by stirring overnight at room temperature, to thereby obtain a reaction mixture. The obtained reaction mixture was evaporated to dryness, to thereby obtain a residue. The obtained residue was purified by silica gel column chromatography (silica gel: Art No. 9385, Silica gel 60, 200–400 mesh, manufactured and sold by E. Merck, Darmstadt, Germany, eluent: methylene chloride/acetonitrile=70/30) to thereby obtain 28 mg of compound (16) (drug complex).

$^1$H-NMR (DMSO-d$_6$): δ0.62 (t, 3H, J=7.5 Hz, Me-Ile), 0.81 (d, 3H, J=6.7 Hz, Me-Ile), 1.01 (s, 3H, Me-17), 1.03 (s, 3H, Me-16), 1.06 (t, 3H, J=7.5 Hz, Me-Pr), 1.07 (ddd, 1H, J=14.4, 7.3, 4.9 Hz, H-Ile), 1.32 (ddd, 1H, J=13.4, 7.6, 4.6 Hz, H-Ile), 1.51 (s, 3H, Me-19), 1.56 (dd, 1H, J=15.3, 9.2 Hz, H-14b), 1.56–1.61 (m, 1H, H-Ile), 1.64 (dd, 1H, J=13.7, 3.1 Hz, H-6b), 1.79 (s, 3H, Me-18), 1.87 (dd, 1H, J=15.3, 9.8 Hz, H-14a), 2.10 (s, 3H, Ac-10), 2.29 (s, 3H, Ac-4), 2.33 (ddd, 1H, J=14.4, 9.6, 6.4 Hz, H-6a), 2.40 (q, 2H, J=7.5 Hz, $CH_2$—Pr), 3.60 (d, 1H, J=7.3 Hz, H-3), 3.60–3.67 (m, 1H, H-Ile), 4.02 (d, 1H, J=16.6 Hz, H-20), 4.03 (d, 1H, J=16.6 Hz, H-20), 4.12 (ddd, 1H, J=10.8, 6.7, 6.7 Hz, H-7), 4.64 (s, 1H, OH-1), 4.90 (d, 1H, J=7.0 Hz, OH-7), 4.92 (d, 1H, J=9.8 Hz, H-5), 5.37 (d, 1H, J=8.9 Hz, H-2'), 5.43 (d, 1H, J=7.3 Hz, H-2), 5.64 (t, 1H, J=8.7 Hz, H-3'), 5.85 (dt, 1H, J=0.9, 9.2 Hz, H-13), 6.30 (s, 1H, H-10), 7.20–8.00 (aromatic, 15H), 9.15 (d, 1H, J=9.2 Hz, CONH-3')

(Step 4) Production of PEG-2'-Ile-paclitaxel (17)

Figure 14:
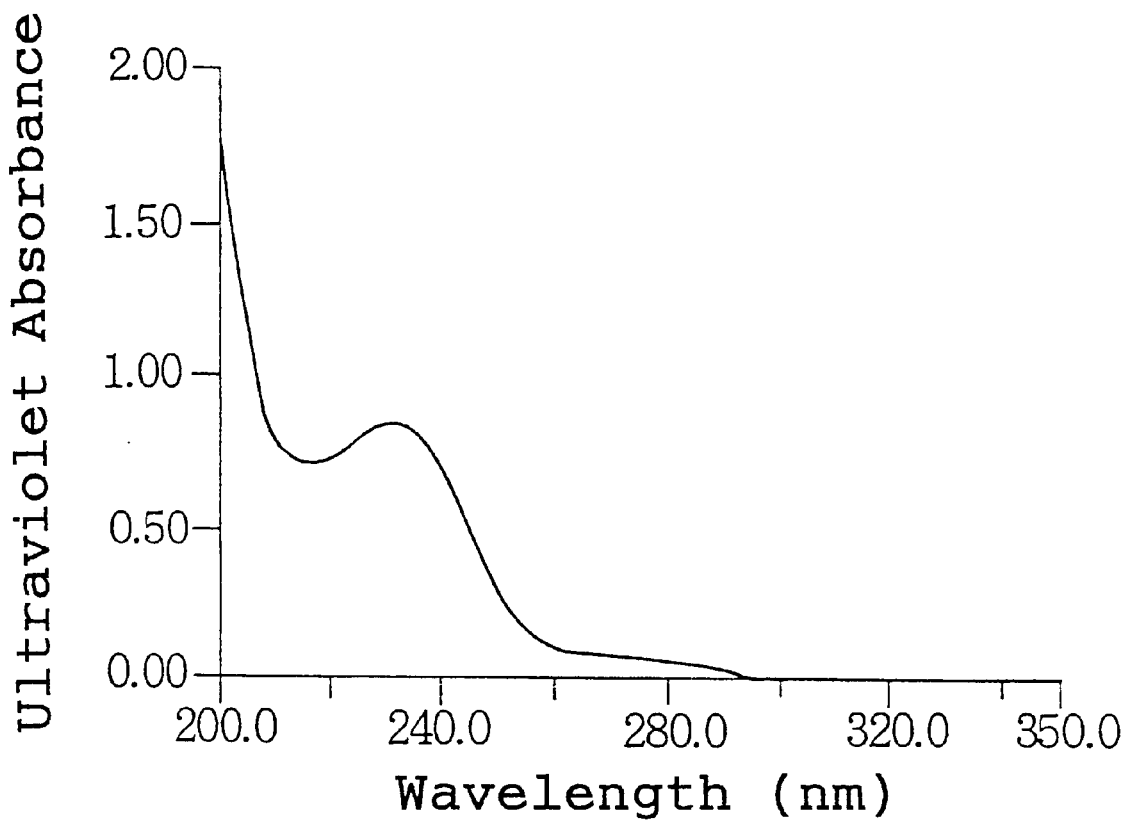
FIG. 14 is a chart showing the ultraviolet visible absorption spectrum of PEG-2'-Ile-paclitaxel (17) obtained in Example 4 (concentration: 214 µg/ml, solvent: water).

CM-PEG (500 mg, 0.1 mmol) obtained in step 5 of Example 1 was dissolved in 5 ml of N,N-dimethylformamide, to thereby obtain a solution. To the obtained solution were added 2'-Ile-paclitaxel (14) (45 mg, 0.05 mmol) obtained in step 1, 4-dimethylaminopyridine (12 mg, 0.1 mmol) and N,N'-diisopropylcarbodiimide (12.6 mg, 0.1 mmol), followed by stirring overnight at room temperature, to thereby obtain a reaction mixture. The obtained reaction mixture was evaporated to dryness, to thereby obtain a residue. The obtained residue was dissolved into 2-propanol while heating, and the resultant solution was subjected to recrystallization, to thereby generate a precipitate. The generated precipitate was washed with cooled 2-propanol and ether successively, followed by drying under reduced pressure, to thereby obtain 125 mg of compound (17) (drug complex). The ultraviolet absorption spectrum of compound (17) is shown in FIG. 14.

EXAMPLE 5

(Step 1) Production of 2'-Phe-paclitaxel (18)

Z-Phe (194 mg, 0.65 mmol), dimethylaminopyridine (79 mg, 0.65 mmol) and paclitaxel (manufactured and sold by DABUR, India, 427 mg, 0.5 mmol) were dissolved in 20 ml of methylene chloride, to thereby obtain a solution. To the obtained solution was added N,N'-diisopropylcarbodiimide (82 mg, 0.65 mmol) and stirred overnight at room temperature, to thereby obtain a reaction mixture. The obtained reaction mixture was evaporated to dryness, to thereby obtain a residue. The obtained residue was purified by silica gel column chromatography (silica gel: Art No. 9385, Silica gel 60, 200–400 mesh, manufactured and sold by E. Merck, Darmstadt, Germany, methylene chloride/acetonitrile 70/30), to thereby obtain 428 mg of 2'-Z-Phe-paclitaxel. 400 mg of the obtained compound was dissolved in 20 ml of dioxane, to thereby obtain a mixture. To the obtained mixture was added 200 mg of a palladium-carbon catalyst, followed by stirring for 4 hours in an atmosphere of hydrogen, to thereby obtain a reaction mixture. The obtained reaction mixture was subjected to filtration to remove the catalyst, thereby obtaining a solution. The obtained solution was evaporated to dryness under reduced pressure, to thereby obtain a residue. The obtained residue was purified by silica gel column chromatography (silica gel: Art No. 9385, Silica gel 60, 200–400 mesh, manufactured and sold by E. Merck, Darmstadt, Germany, column: 4.0×30 cm, eluent: methylene chloride/methanol/acetonitrile=95/5/5), to thereby obtain 269 mg of compound (18).

$^1$H-NMR (DMSO-$d_6$): δ1.02 (s, 3H, Me-17), 1.05 (s, 3H, Me-16), 1.52 (s, 3H, Me-19), 1.64 (dd, 1H, J=15.6, 9.2 Hz, H-14b), 1.66 (dd, 1H, J=14.4, 11.3 Hz, H-6b), 1.85 (s, 3H, Me-18), 1.93 (dd, 1H, J=15.3, 9.5 Hz, H-14a), 2.11 (s, 3H, Ac-10), 2.30 (s, 3H, Ac-4), 2.32 (ddd, 1H, J=14.7, 9.6, 6.6 Hz, H-6a), 2.99 (dd, 1H, 14.5, 6.9 Hz, PheCH$_2$), 3.13 (dd, 1H, 14.4, 5.2 Hz, PheCH$_2$), 3.61 (d, 1H, J=7.3 Hz, H-3), 4.10 (dd, 1H, J=11.0, 6.7 Hz, H-7), 4.52 (t, 1H, J=5.8 Hz, PheCH), 4.68 (s, 1H,.OH-1), 4.89 (d, 1H, J=7.0 Hz, OH-7), 4.92 (d, 1H, J=9.8 Hz, H-5), 5.47 (d, 1H, J=7.3-Hz, H-2'), 5.50 (d, 1H, J=7.3 Hz, H-2), 5.78 (t, 1H, J=8.2 Hz, H-3'), 5.94 (t, 1H, J=8.9 Hz, H-13), 6.30 (s, 1H, H-10), 7.00–8.10 (m, 20H, aromatic), 8.49 (brs, 2H, NH$_2$) 9.26 (d, 1H, J=8.9 Hz, CONH-3')

HRMS: m/z 1001.4076 (M+H)$^+$: the molecular weight calculated for $C_{56}H_{61}O_{15}N_2$ 1001.4072

(Step 2) Production of carboxymethylated dextran-2'-Phe-paclitaxel (19)

100 mg of carboxymethylated dextran sodium salt (1) obtained in Example 1 was dissolved in 2 ml of water. To the resultant solution was added 2 ml of N,N-dimethylformamide while cooling over ice. To the resultant mixture were added 0.5 ml of a solution containing 30 mg of 2'-Phe-paclitaxel (18) obtained in step 1, which was dissolved in a mixture of water and N,N-dimethylformamide (1:1), and 0.5 ml of a solution containing 100 mg of 1-ethoxycarbonyl-2-ethoxy-1,2-dihydroquinoline dissolved in N,N-dimethylformamide, followed by stirring at room temperature for two hours, to thereby obtain a reaction mixture. The obtained reaction mixture was poured into 100 ml of ethanol, to thereby generate a precipitate. The generated precipitate was collected and dissolved in 10 ml of purified water. The resultant solution was poured into 100 ml of ethanol, to thereby generate a precipitate. The generated precipitate was collected and washed with acetone and ether successively, to thereby obtain 106 mg of compound (19) (drug complex) as a white amorphous substance.

Figure 15:
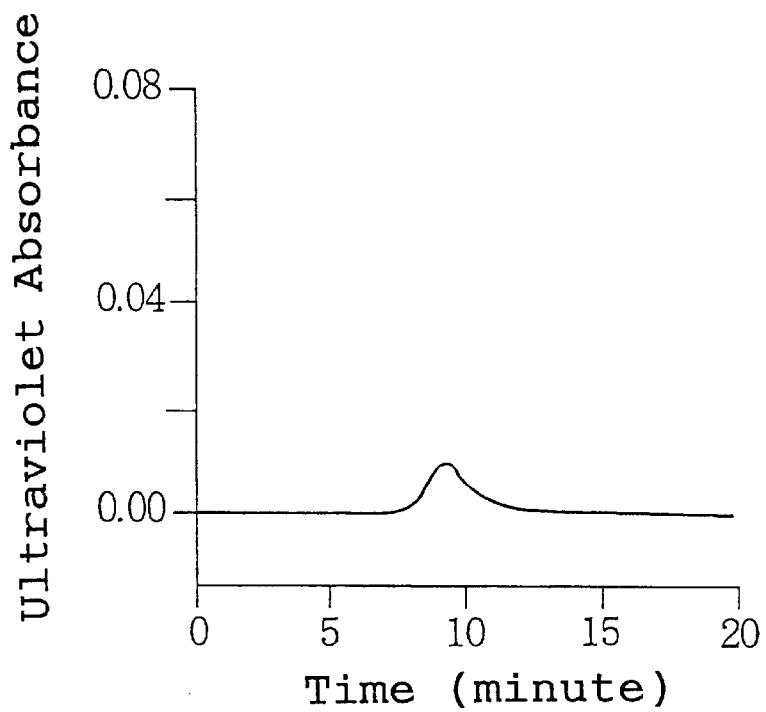
FIG. 15 is a chart showing the gel filtration chromatogram of carboxymethylated dextran-2'-Phe-paclitaxel (19) obtained in Example 5, wherein the chromatogram was obtained using an ultraviolet detector (wavelength: 227 nm).
Figure 16:
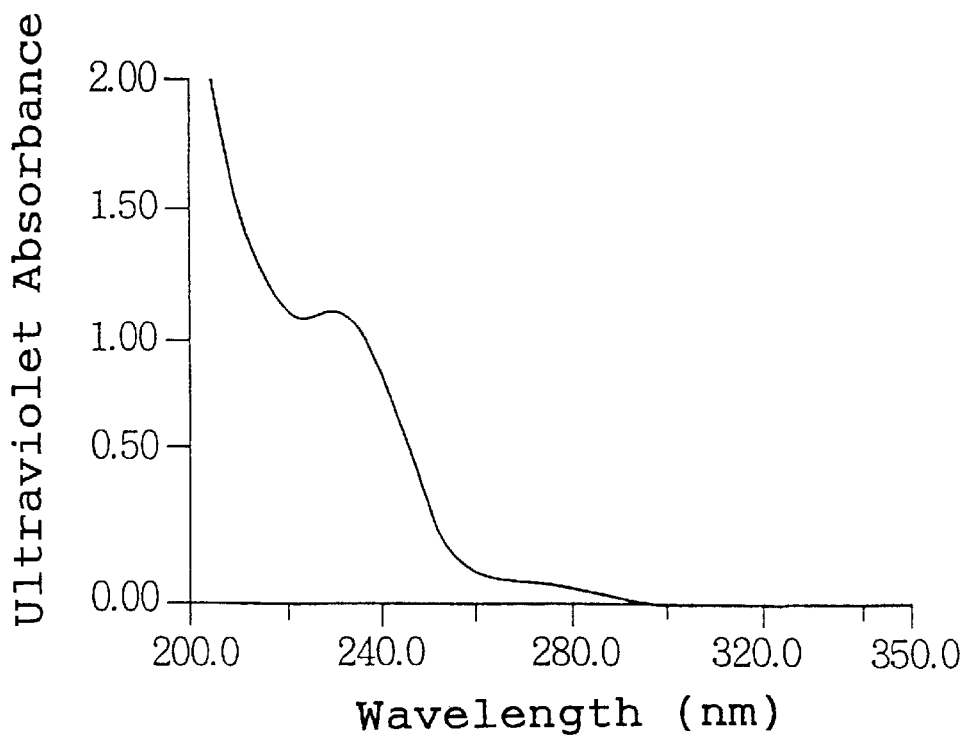
FIG. 16 is a chart showing the ultraviolet absorption spectrum of carboxymethylated dextran-2'-Phe-paclitaxel (19) obtained in Example 5 (concentration: 814 µg/ml, solvent: water).

The amount of the drug introduced into compound (19) was calculated from the ultraviolet absorbance at 254 nm, and found to be 4.7% by weight, based on the weight of compound (19). The gel filtration chromatogram of compound (19) was obtained using an ultraviolet detector (wavelength: 227 nm), and is shown in FIG. 15. The ultraviolet absorption spectrum of compound (19) is shown in FIG. 16.

EXAMPLE 6

(Step 1) Production of 21-Phe-Gly-paclitaxel hydrochloride (20)

Phe-Gly (manufactured and sold by PEPTIDE INSTITUTE INC., Japan, 1.1 g, 5 mmol) was dissolved in a 10 mixture of 2 ml of H$_2$O, 2 ml of 2-propanol and 1.5 ml of diethylamine, to thereby obtain a solution. To the obtained solution was portionwise added trityl chloride (1.8 g, 6.5 mmol), followed by stirring for one hour. To the resultant reaction mixture was added H$_2$O, to thereby generate a precipitate. The generated precipitate was collected, washed with water and then dissolved into 5 ml of acetic acid, to thereby obtain an acidic solution. The obtained acidic solution was evaporated to dryness under reduced pressure, to thereby obtain 1.5 g of Trt-Phe-Gly.

The above-obtained Trt-Phe-Gly (604 mg, 1.3 mmol), dimethylaminopyridine (158 mg, 1.3 mmol) and paclitaxel (manufactured and sold by DABUR, India, 853 mg, 1.0 mmol) were dissolved in 20 ml of methylene chloride, to thereby obtain a solution. To the obtained solution was added N,N'-diisopropylcarbodiimide (164 mg, 1.3 mmol), followed by stirring overnight at room temperature, to thereby obtain a reaction mixture. The obtained reaction mixture was evaporated to dryness, to thereby obtain a residue. The obtained residue was purified by silica gel column chromatography (silica gel: Art No. 9385, Silica gel 60, 200–400 mesh, manufactured and sold by E. Merck, Darmstadt, Germany, Column: 4.0×30 cm, eluent: methylene chloride/acetonitrile=80/20), to thereby obtain 983 mg of 2'-Trt-Phe-Gly-paclitaxel. 800 mg of the above-obtained compound was treated with 10 ml of 90% acetic acid to effect a reaction for removing N-trityl group. The resultant compound was purified by silica gel column chromatography (silica gel Art No. 9385, Silica gel 60, 200–400 mesh, manufactured and sold by E. Merck, Darmstadt, Germany, column 4.0×30 cm, eluent methylene chloride/methanol/acetonitrile=95/5/5), and subsequently converted to a corresponding hydrochloride thereof, to thereby obtain 490 mg of compound (20).

$^1$H-NMR (DMSO-$d_6$): δ1.01 (s, 3H, Me-17), 1.03 (s, 3H, Me-16), 1.42 (dd, 1H, J=15.5, 9.1 Hz, H-14b), 1.50 (s, 3H, Me-19), 1.63 (t, 1H, J=12.2 Hz, H-6b), 1.75 (dd, 1H, J=12.3, 9.5 Hz, H-14a), 1.81 (s, 3H, Me-18), 2.12 (s, 3H, Ac-10), 2.23 (s, 3H, Ac-4), 2.29 (ddd, 1H, J=14.4, 9.2, 7.0 Hz, H-6a), 2.90 (dd, 1H, 14.2, 7.8 Hz, PheCH$_2$), 3.08 (dd, 1H, 14.4, 5.2 Hz, PheCH$_2$), 3.56 (d, 1H, J=7.0 Hz, H-3), 4.05–4.10 (m, 2H, H-7, PheCH), 4.15 (dd, 1H, J=18.0, 5.8 Hz, Gly), 4.61 (brs, 1H, OH-1), 4.90 (brs, 1H, OH-7), 4.90 (d, 1H, J=5.3 Hz, H-5), 5.38 (d, 1H, J=8.9 Hz, H-2'), 5.41 (d, 1H, J=7.0 Hz, H-2), 5.53 (t, 1H, J=8.6 Hz, H-3'), 5.83 (t, 1H, J=8.8 Hz, H-13), 6.29 (s, 1H, H-10), 7.16–8.00 (m, 20H, aromatic), 8.15 (brs, 2H, NH$_2$), 9.02 (t, 1H, J=5.8 Hz, Gly-NH), 9.29 (d, 1H, J=8.9 Hz, CONH-3')

HRMS: m/z 1058.4241 (M+H)$^+$: the molecular weight calculated for $C_{58}H_{64}O_{16}N_3$ 1058.4287

(Step 2) Production of carboxymethylated dextran-2'-Phe-Gly-paclitaxel (21)

100 mg of carboxymethylated dextran sodium salt (1) obtained in Example 1 was dissolved in 2 ml of water. To the resultant solution was added 2 ml of N,N-dimethylformamide while cooling over ice. To the resultant mixture were added 0.5 ml of a solution containing 22 mg of 2'-Phe-Gly-paclitaxel (20) obtained in step 1, which was dissolved in a mixture of water and N,N-dimethylformamide (1:1), and 0.5 ml of a solution containing 100 mg of 1-ethoxycarbonyl-2-ethoxy-1,2-dihydroquinoline dissolved in N,N-dimethylformamide, followed by stirring at room temperature for two hours, to thereby obtain a reaction mixture. The obtained reaction mixture was poured into 100 ml of ethanol, to thereby generate a precipitate. The generated precipitate was collected and dissolved in 10 ml of purified water. The resultant solution was poured into 100 ml of ethanol, to thereby generate a precipitate. The generated precipitate was washed with acetone and ether successively, to thereby obtain 108 mg of compound (21) (drug complex) as a white amorphous substance.

Figure 17:
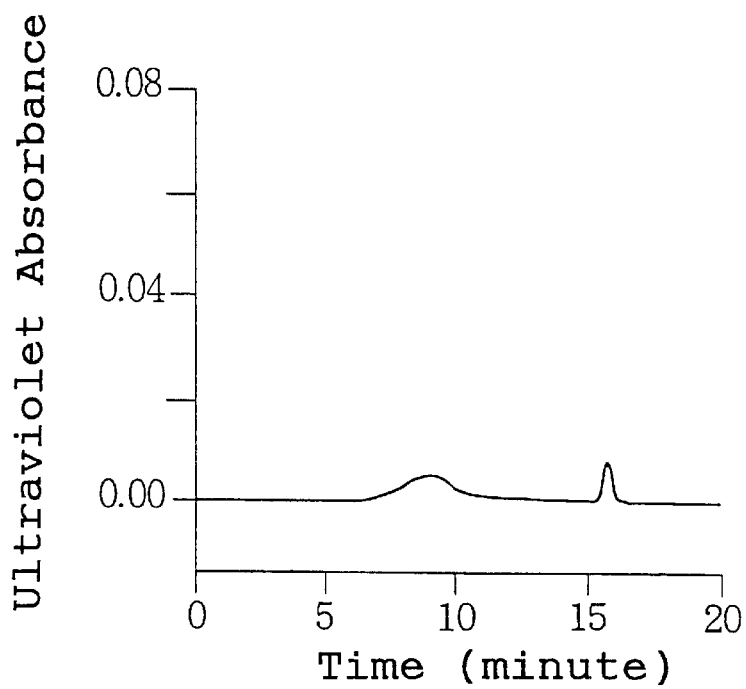
FIG. 17 is a chart showing the gel filtration chromatogram of carboxymethylated dextran-$2^1$-Phe-Gly-paclitaxel (21) obtained in Example 6, wherein the chromatogram was obtained using an ultraviolet detector (wavelength: 227 nm).
Figure 18:
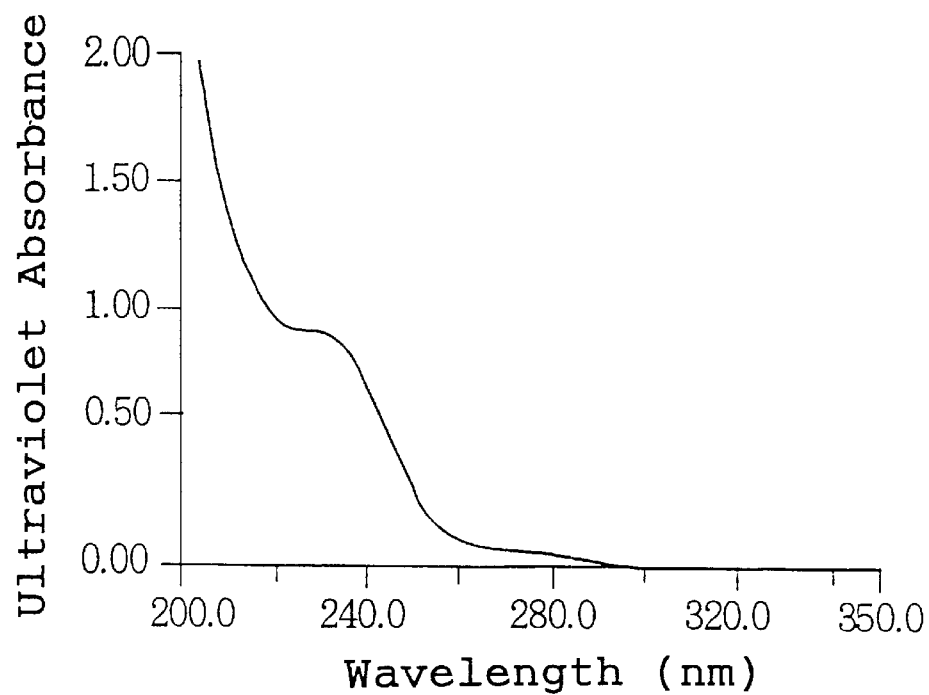
FIG. 18 is a chart showing the ultraviolet absorption spectrum of carboxymethylated dextran-2'-Phe-Gly-paclitaxel (21) obtained in Example 6 (concentration: 940 µg/ml, solvent: water).

The amount of the drug introduced into compound (21) was calculated from the ultraviolet absorbance at 254 nm, and found to be 3.3% by weight, based on the weight of compound (21). The gel filtration chromatogram of compound (21) was obtained using an ultraviolet detector (wavelength: 227 nm), and is shown in FIG. 17. The ultraviolet absorption spectrum of compound (21) is shown in FIG. 18.

EXAMPLE 7

(Step 1) Production of 2'-Gly-Phe-paclitaxel hydrochloride (22)

Production of compound (22) was conducted in substantially the same manner as in step 1 of Example 6. That is, Gly-Phe (manufactured and sold by PEPTIDE INSTITUTE INC., Japan, 1.1 g, 5 mmol) was dissolved in a mixture of 2 ml of H$_2$O, 2 ml of 2-propanol and 1.5 ml of diethylamine, to obtain a solution. To the obtained solution was portionwise added trityl chloride (1.8 g, 6.5 mmol), followed by stirring for one hour. To the resultant reaction mixture was added H$_2$O, to thereby generate a precipitate. The generated precipitate was collected, washed with water and then dissolved into 5 ml of acetic acid, to thereby obtain an acidic solution. The obtained acidic solution was evaporated to dryness under reduced pressure, to thereby obtain 1.5 g of Trt-Gly-Phe.

The above-obtained Trt-Gly-Phe (604 mg, 1.3 mmol), dimethylaminopyridine (158 mg, 1.3 mmol) and paclitaxel (manufactured and sold by DABUR, India, 853 mg, 1.0 mmol) were dissolved in 20 ml of methylene chloride, to thereby obtain a mixture. To the obtained mixture was added N,N'-diisopropylcarbodiimide (164 mg, 1.3 mmol), followed by stirring overnight at room temperature, to thereby obtain a reaction mixture. The obtained reaction mixture was evaporated to dryness to thereby obtain a residue. The obtained residue was purified by silica gel column chromatography (silica gel Art No. 9385, Silica gel 60, 200–400 mesh, manufactured and sold by E. Merck, Darmstadt, Germany, column: 4.0×30 cm, eluent: methylene chloride/acetonitrile=80/20), to thereby obtain 968 mg of 2'-Trt-Gly-Phe-paclitaxel. 800 mg of the above-obtained compound was treated with 10 ml of 90% acetic acid to effect a reaction for removing N-trityl group. The resultant compound was purified by silica gel column chromatography (silica gel: Art No. 9385, Silica gel 60, 200–400 mesh, manufactured and sold by E. Merck, Darmstadt, Germany, column: 4.0×30 cm, eluent: methylene chloride/methanol/acetonitrile 95/5/5), and subsequently converted to a corresponding hydrochloride thereof, to thereby obtain 520 mg of compound (22).

$^1$H-NMR (DMSO-$d_6$): δ1.02 (s, 3H, Me-17), 1.05 (s, 3H, Me-16), 1.52 (s, 3H, Me-19), 1.66 (dd, 1H, J=15.0, 9.5 Hz, H-14b), 1.66 (t, 1H, J=10.7 Hz, H-6b), 1.82 (s, 3H, Me-18), 1.94 (dd, 1H, J=15.2, 9.7 Hz, H-14a), 2.11 (s, 3H, Ac-10), 2.30 (br, 1H, H-6a), 2.33 (s, 3H, Ac-4), 2.76 (dd, 1H, 14.1, 9.5 Hz, PheCH$_2$), 2.97 (dd, 1H, 14.0, 3.6 Hz, PheCH$_2$), 3.46 (d, 1H, J=1–6.2, Gly), 3.51 (d, 1H, J=16.5, Gly), 3.61 (d, 1H, J=7.3 Hz, H-3), 4.03 (d, 1H, J=8.9 Hz, H-20), 4.05 (d, 1H, J=8.9 Hz, H-20), 4.10 (dd, 1H, J=10.5, 6.9 Hz, H-7), 4.71 (brs, 1H, OH-1), 4.79 (ddd, 1H, J=9.0, 9.0, 3.7 Hz, PheCH), 4.92 (brs, 1H, OH-7), 4.93 (d, 1H, J=10.4 Hz, H-5), 5.40 (d, 1H, J=7.6 Hz, H-2'), 5.44 (d, 1H, J=7.3 Hz, H-2), 5.79 (dd, 1H, J=8.6, 7.9 Hz, H-3'), 5.93 (t, 1H, J=8.9 Hz, H-13), 6.29 (s, 1H, H-10), 6.97–8.02 (m, 20H, aromatic), 7.97 (brs, 2H, GlyNH$_2$), 8.88 (d, 1H, J=8.2 Hz, Phe-NH), 9.30 (d, 1H, J=9.2 Hz, CONH-3')

HRMS: m/z 1058.4333 (M+H)$^+$: the molecular weight calculated for $C_{58}H_{64}O_{16}N_3$ 1058.4287

(Step 2) Production of carboxymethylated dextran-2'-Gly-Phe-paclitaxel (23)

100 mg of carboxymethylated dextran sodium salt (1) obtained in Example 1 was dissolved in 2 ml of water. To the resultant solution was added 2 ml of N,N-dimethylformamide while cooling over ice. To the resultant mixture were added 0.5 ml of a solution containing 15 mg of 2'-Gly-Phe-paclitaxel (22) obtained in step 1, which is dissolved in a mixture of water and N,N-dimethylformamide (1:1), and 0.5 ml of a solution containing 100 mg of 1-ethoxycarbonyl-2-ethoxy-1,2-dihydroquinoline dissolved in N,N-dimethylformamide, followed by stirring at room temperature for two hours, to thereby obtain a reaction mixture. The obtained reaction mixture was poured into 100 ml of ethanol, to thereby generate a precipitate. The generated precipitate was collected and dissolved in 10 ml of purified water. The resultant solution was poured into 100 ml of ethanol, to thereby generate a precipitate. The generated precipitate was collected and washed with acetone and ether successively, to thereby obtain 101 mg of compound (23) (drug complex) as a white amorphous substance.

Figure 19:
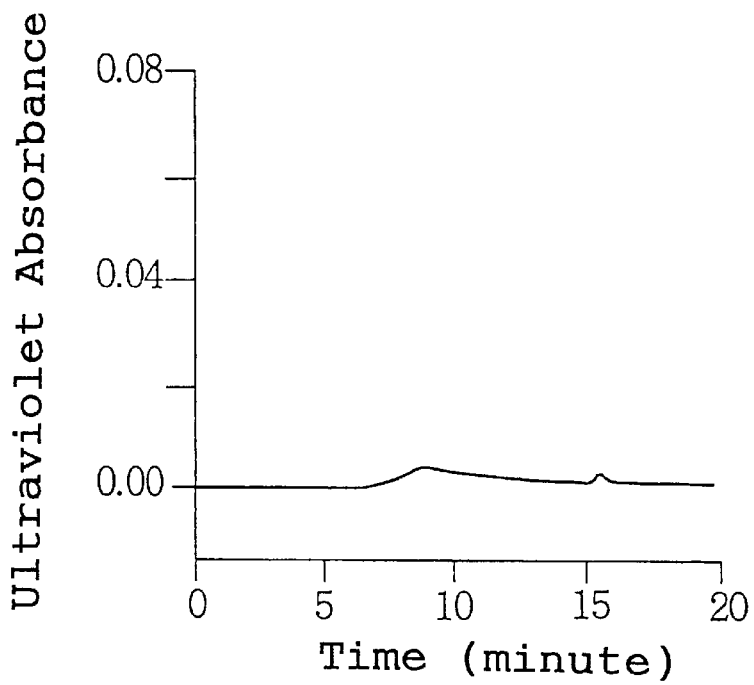
FIG. 19 is a chart showing the gel filtration chromatogram of carboxymethylated dextran-2'-Gly-Phe-paclitaxel (23) obtained in Example 7, wherein the chromatogram was obtained using an ultraviolet detector (wavelength: 227 nm).
Figure 20:
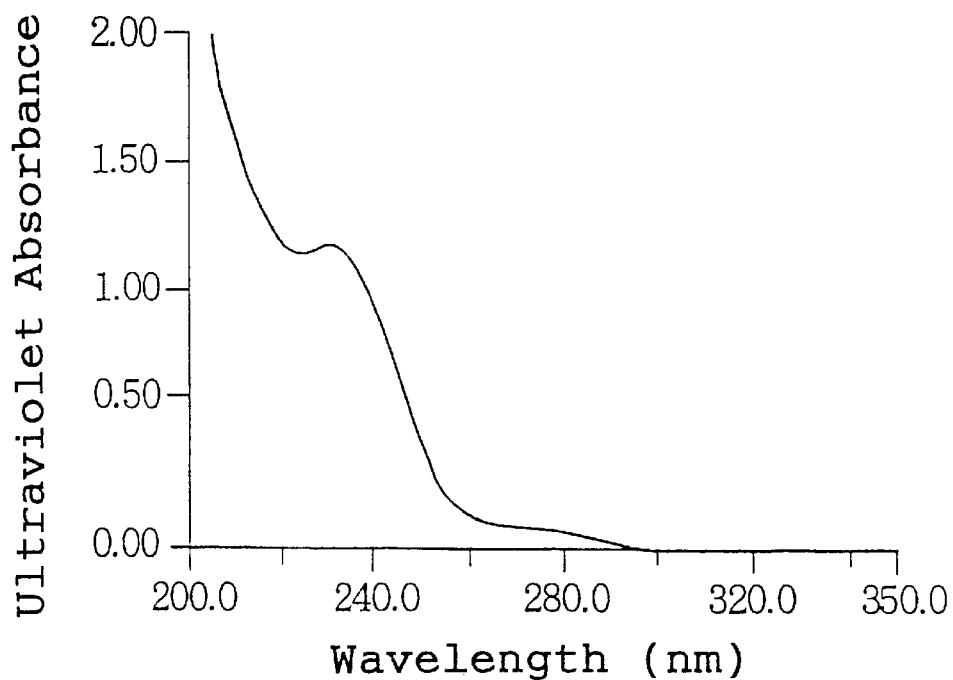
FIG. 20 is a chart showing the ultraviolet absorption spectrum of carboxymethylated dextran-2'-Gly-Phe-paclitaxel (23) obtained in Example 7 (concentration: 854 µg/ml, solvent: water)

The amount of the drug introduced into compound (23) was calculated from the ultraviolet absorbance at 254 nm, and found to be 4.7% by weight, based on the weight of compound (23). The gel filtration chromatogram of compound (23) was obtained using an ultraviolet detector (wavelength: 227 nm), and is shown in FIG. 19. The ultraviolet absorption spectrum of compound (23) is shown in FIG. 20.

EXAMPLE 8

(1) Production of 21-propanoylisoleucyl-dexamethasone (24)

Z-Ile (172 mg, 0.65 mmol), dimethylaminopyridine (79 mg, 0.65 mmol) and dexamethasone (manufactured and sold by Wako Pure Chemical Industries, Ltd., Japan, 196 mg, 0.5 mmol) were dissolved in 20 ml of DMF, to thereby obtain a solution. To the obtained solution was added N,N'-diisopropylcarbodiimide (82 mg, 0.65 mmol) and stirred overnight at room temperature, to thereby obtain a reaction mixture. The obtained reaction mixture was evaporated to dryness, to thereby obtain a residue. The obtained residue was purified by silica gel column chromatography (silica gel: Art No. 9385, Silica gel 60, 200–400 mesh, manufactured and sold by E. Merck, Darmstadt, Germany, eluent: chloroform/ethyl acetate=50/30), to thereby obtain 62 mg of 21-Z-Ile-dexamethasone. 50 mg of the obtained compound was dissolved in 20 ml of dioxane, to thereby obtain a mixture. To the obtained mixture was added 50 mg of a palladium-carbon catalyst, followed by stirring for 4 hours in an atmosphere of hydrogen, to thereby obtain a reaction mixture. The obtained reaction mixture was subjected to filtration to remove the catalyst, thereby obtaining a solution. The obtained solution was evaporated to dryness under reduced pressure, to thereby obtain a residue. The obtained residue was dissolved in DMF, to thereby obtain a solution. To the obtained solution were added 4-dimethylaminopyridine (61 mg, 0.5 mmol), N,N'-diisopropylcarbodiimide (63 mg, 0.5 mmol) and propionic acid (37 mg, 0.5 mmol), followed by stirring overnight at room temperature, to thereby obtain a reaction mixture. The obtained reaction mixture was evaporated to dryness, to thereby obtain a residue. The obtained residue was purified by silica gel column chromatography (silica gel: Art No. 9385, Silica gel 60, 200–400 mesh, manufactured and sold by E. Merck, Darmstadt, Germany, chloroform/ethyl acetate=50/25), to thereby obtain 50 mg of compound (24) (drug complex).

$^1$H-NMR (DMSO-$d_6$): $\delta$0.63 (s, 3H, J 7.5 Hz), 0.76 (d, 3H, 7.5 Hz), 0.82 (d, 3H, J=6.7 Hz), 0.87 (s, 3H), 1.07 (m, 2H), 1.10 (t, 3H, J=7.5 Hz), 1.30–1.50 (m, 3H), 1.49 (s, 3H), 1.55–1.62 (m, 2H), 1.78 (m, 1H), 2.11 (m, 2H), 2.32 (m, 2H), 2.35 (q, 2H, J=7.5 Hz), 2.60 (m, 1H), 2.94 (m, 1H), 3.60–3.68 (m, 1H), 4.16 (m, 1H), 4.68 (m, 1H), 4.68 (d, 1H, J=17.2 Hz), 5.01 (d, 1H, J=17.2 Hz), 5.16 (brs, 1H), 6.01 (s, 1H), 6.23 (d, 1H, J=10.2 Hz), 7.30 (d, 1H, J=10.2 Hz), 9.00 (d, 1H, J=7.0 Hz)

(2) Production of PEG-isoleucyl-21-dexamethasone (25)

Figure 21:
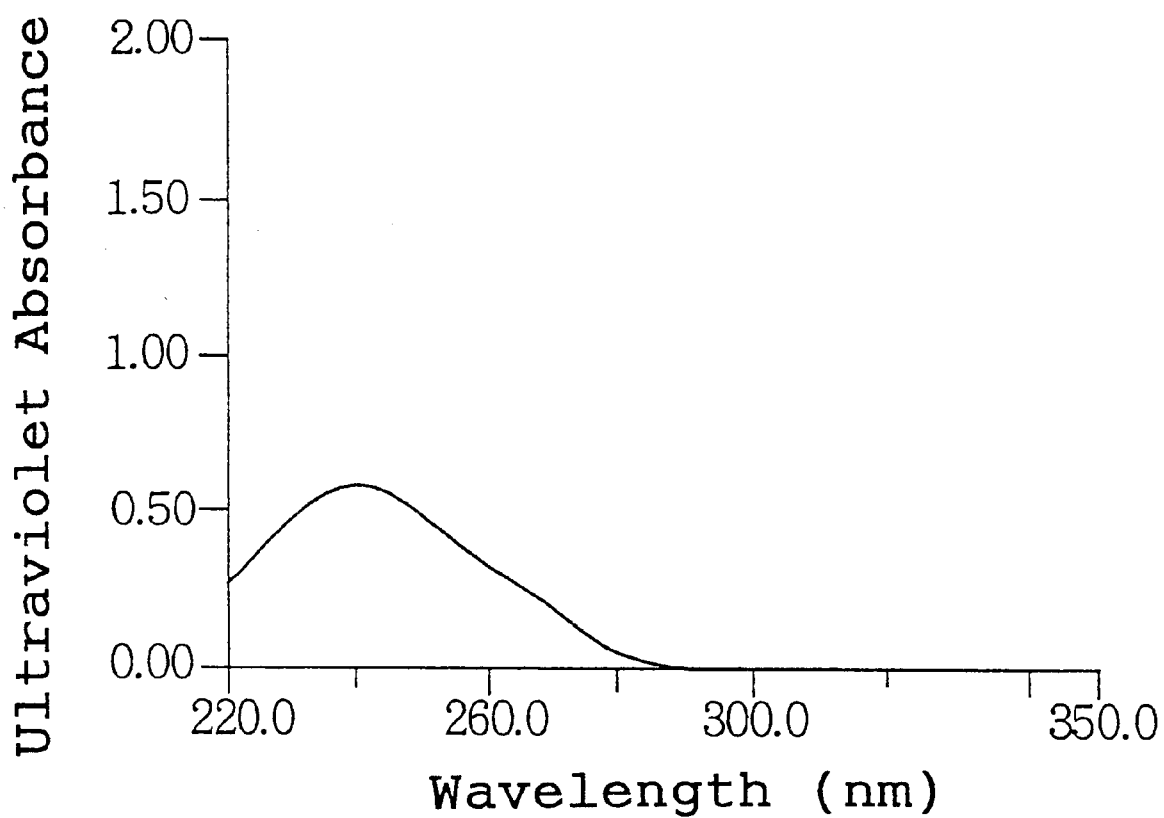
FIG. 21 is a chart showing the ultraviolet absorption spectrum of PEG-isoleucyl-21-dexamethasone (25) obtained in Example 8 (concentration: 245 µg/ml, solvent: water).

Z-Ile (172 mg, 0.65 mmol), dimethylaminopyridine (79 mg, 0.65 mmol) and dexamethasone (manufactured and sold by Wako Pure Chemical Industries, Ltd., Japan, 196 mg, 0.5 mmol) were dissolved in 20 ml of DMF, to thereby obtain a solution. To the obtained solution was added N,N'-diisopropylcarbodiimide (82 mg, 0.65 mmol) and stirred overnight at room temperature, to thereby obtain a reaction mixture. The obtained reaction mixture was evaporated to dryness, to thereby obtain a residue. The obtained residue was purified by silica gel column chromatography (silica gel Art No. 9385, Silica gel 60, 200–400 mesh, manufactured and sold by E. Merck, Darmstadt, Germany, eluent: chloroform/ethyl acetate=50/30), to thereby obtain 65 mg of 21-Z-Ile-dexamethasone. 50 mg of the obtained compound was dissolved in 20 ml of dioxane, to thereby obtain a mixture. To the obtained mixture was added 50 mg of a palladium-carbon catalyst, followed by stirring for 4 hours in an atmosphere of hydrogen, to thereby obtain a reaction mixture. The obtained reaction mixture was subjected to filtration to remove the catalyst, thereby obtaining a solution. The obtained solution was evaporated to dryness under reduced pressure, to thereby obtain a residue. The obtained residue was dissolved in DMF, to thereby obtain a solution. To the obtained solution were added 4-dimethylaminopyridine (61 mg, 0.5 mmol), N,N'-diisopropylcarbodiimide (63 mg, 0.5 mmol) and the CM-PEG (2,500 mg, 0.5 mmol) obtained in step 5 of Example 1, followed by stirring overnight at room temperature, to thereby obtain a reaction mixture. The obtained reaction mixture was evaporated to dryness, to thereby obtain a residue. The obtained residue was washed with 2-propanol and ether successively, followed by drying under reduced pressure, to thereby obtain 1,000 mg of compound (25) (drug complex). The ultraviolet absorption spectrum of compound (25) is shown in FIG. 21.

(3) Production of 21-propanoylglycyl-dexamethasone (26)

Z-Gly (135 mg, 0.65 mmol), dimethylaminopyridine (79 mg, 0.65 mmol) and dexamethasone (manufactured and sold by Wako Pure Chemical Industries, Ltd., Japan, 196 mg, 0.5 mmol) were dissolved in 20 ml of DMF, to thereby obtain a solution. To the obtained solution was added N,N'-diisopropylcarbodiimide (82 mg, 0.65 mmol) and stirred overnight at room temperature, to thereby obtain a reaction mixture. The obtained reaction mixture was evaporated to dryness, to thereby obtain a residue. The obtained residue was purified by silica gel column chromatography (silica gel Art No. 9385, Silica gel 60, 200–400 mesh, manufactured and sold by E. Merck, Darmstadt, Germany, eluent: chloroform/methanol=15/1), to thereby obtain 68 mg of 21-Z-Gly-dexamethasone. 50 mg of the obtained compound was dissolved in 20 ml of dioxane, to thereby obtain a mixture. To the obtained mixture was added 50 mg of a palladium-carbon catalyst, followed by stirring for 4 hours in an atmosphere of hydrogen, to thereby obtain a reaction mixture. The obtained reaction mixture was subjected to filtration to remove the catalyst, thereby obtaining a solution. The obtained solution was evaporated to dryness under reduced pressure, to thereby obtain a residue. The obtained residue was dissolved in DMF, to thereby obtain a solution. To the obtained solution were added 4-dimethylaminopyridine (61 mg, 0.5 mmol), N,N'-diisopropylcarbodiimide (63 mg, 0.5 mmol) and propionic acid (37 mg, 0.5 mmol), followed by stirring overnight at room temperature, to thereby obtain a reaction mixture. The obtained reaction mixture was evaporated to dryness, to thereby obtain a residue. The obtained residue was purified by silica gel column chromatography (silica gel: Art No. 9385, Silica gel 60, 200–400 mesh, manufactured and sold by E. Merck, Darmstadt, Germany, eluent: chloroform/methanol=17/1), to thereby obtain 30 mg of compound (26) (drug complex).

$^1$H-NMR (DMSO-$d_6$): $\delta$0.74 (d, 3H, 7.5 Hz), 0.88 (d, 3H), 1.04 (t, 3H, J=7.5 Hz), 1.07 (m, 2H), 1.30–1.50 (m, 3H), 1.52 (s, 3H), 1.60 (m, 2H), 1.78 (m, 1H), 2.14 (m, 2H), 2.32 (m, 2H), 2.37 (q, 2H, J=7.5 Hz), 2.62 (m, 1H), 2.94 (m, 1H), 3.96–4.06 (m, 2H), 4.16 (m, 1H), 4.68 (m, 1H), 4.82 (d, 1H, J=17.4 Hz), 4.98 (brs, 1H), 5.03 (d, 1H, J=17.4 Hz), 6.02 (s, 1H), 6.24 (dd, 1H, J=10.3, 1.7 Hz), 7.29 (d, 1H, J=10.2 Hz), 9.02 (d, 2H, J=7.0 Hz)

(4) Production of PEG-glycyl-21-dexamethasone (27)

Figure 22:
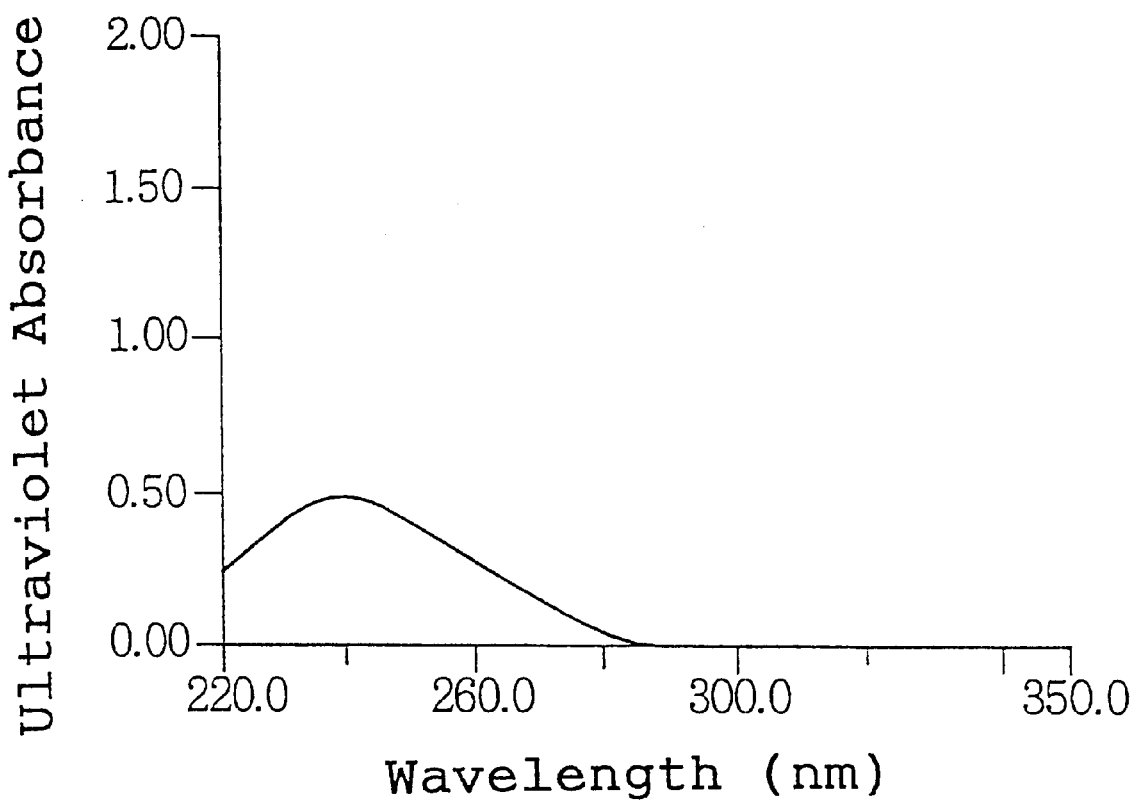
FIG. 22 is a chart showing the ultraviolet absorption spectrum of PEG-glycyl-21-dexamethasone (27) obtained in Example 8 (concentration: 201 µg/ml, solvent: water).

Z-Gly (135 mg, 0.65 mmol), dimethylaminopyridine (79 mg, 0.65 mmol) and dexamethasone (manufactured and sold by Wako Pure Chemical Industries, Ltd., Japan 196 mg, 0.5 mmol) were dissolved in 20 ml of DMF, to thereby obtain a solution. To the obtained solution was added N,N'-diisopropylcarbodiimide (82 mg, 0.65 mmol) and stirred overnight at room temperature, to thereby obtain a reaction mixture. The obtained reaction mixture was evaporated to dryness, to thereby obtain a residue. The obtained residue was purified by silica gel column chromatography (silica gel: Art No. 9385, Silica gel 60, 200–400 mesh, manufactured and sold by E. Merck, Darmstadt, Germany, eluent: chloroform/methanol=15/1) to thereby obtain 65 mg of 21-Z-Gly-dexamethasone. 50 mg of the obtained compound was dissolved in 20 ml of dioxane, to thereby obtain a mixture. To the obtained mixture was added 50 mg of a palladium-carbon catalyst, followed by stirring for 4 hours in an atmosphere of hydrogen, to thereby obtain a reaction mixture. The obtained reaction mixture was subjected to filtration to remove the catalyst, thereby obtaining a solution. The obtained solution was evaporated to dryness under reduced pressure, to thereby obtain a residue. The obtained residue was dissolved in DMF, to thereby obtain a solution. To the obtained solution were added 4-dimethylaminopyridine (61 mg, 0.5 mmol), N,N'-diisopropylcarbodiimide (63 mg, 0.5 mmol) and the CM-PEG (2,500 mg, 0.5 mmol) obtained in step 1 of Example 5, followed by stirring overnight at room temperature, to thereby obtain a reaction mixture. The obtained reaction mixture was evaporated to dryness, to thereby obtain a residue. The obtained residue was washed with 2-propanol and ether successively, followed by drying under reduced pressure, to thereby obtain 700 mg of compound (27) (drug complex). The ultraviolet absorption spectrum of compound (27) is shown in FIG. 22.

(5) Production of 21-propanoylalanyl-dexamethasone (28)

Z-Ala (145 mg, 0.65 mmol), dimethylaminopyridine (79 mg, 0.65 mmol) and dexamethasone (manufactured and sold by Wako Pure Chemical Industries, Ltd., Japan, 196 mg, 0.5 mmol) were dissolved in 20 ml of DMF, to thereby obtain a solution. To the obtained solution was added N,N'-diisopropylcarbodiimide (82 mg, 0.65 mmol) and stirred overnight at room temperature, to thereby obtain a reaction mixture. The obtained reaction mixture was evaporated to dryness, to thereby obtain a residue. The obtained residue was purified by silica gel column chromatography (silica gel: Art No. 9385, Silica gel 60, 200–400 mesh, manufactured and sold by E. Merck, Darmstadt, Germany, eluent: chloroform/methanol=20/1), to thereby obtain 70 mg of 21-Z-Ala-dexamethasone. 50 mg of the obtained compound was dissolved in 20 ml of dioxane, to thereby obtain a mixture. To the obtained mixture was added 50 mg of a palladium-carbon catalyst, followed by stirring for 4 hours in an atmosphere of hydrogen, to thereby obtain a reaction mixture. The obtained reaction mixture was subjected to filtration to remove the catalyst, thereby obtaining a solution. The obtained solution was evaporated to dryness under reduced pressure, to thereby obtain a residue. The obtained residue was dissolved in DMF, thereby to obtain a solution. To the obtained solution were added 4-dimethylaminopyridine (61 mg, 0.5 mmol), N,N'-diisopropylcarbodiimide (63 mg, 0.5 mmol) and propionic acid (37 mg, 0.5 mmol), followed by stirring overnight at room temperature, to thereby obtain a reaction mixture. The obtained reaction mixture was evaporated to dryness, to thereby obtain a residue. The obtained residue was purified by silica gel column chromatography (silica gel: Art No. 9385, Silica gel 60, 200–400 mesh, manufactured and sold by E. Merck, Darmstadt, Germany, eluent: chloroform/methanol=40/3), to thereby obtain 55 mg of compound (28) (drug complex).

$^1$H-NMR (DMSO-d$_6$): δ0.76 (d, 3H, 7.5 Hz), 0.89 (d, 3H), 1.06 (t, 3H, J=7.5 Hz), 1.07 (m, 2H), 1.14 (s, 3H), 1.30–1.50 (m, 3H), 1.50 (s, 3H), 1.60 (m,-2H), 1.78 (m, 1H), 2.14 (m, 2H), 2.32 (m, 2H), 2.40 (q, 2H, J=7.5 Hz), 2.60 (m, 1H), 2.94 (m, 1H), 3.50 (q, 1H, J=7.0 Hz), 4.16 (m, 1H), 4.68 (m, 1H), 4.78 (d, 1H, J=17.0 Hz), 4.98 (brs, 1H), 5.02 (d, 1H, J=17.0 Hz), 6.02 (s, 1H), 6.24 (dd, 1H, J=10.3, 1.7 Hz), 7.29 (d, 1H, J=10.2 Hz), 8.84 (d, 2H, J=7.0 Hz)

(6) Production of PEG-alanyl-21-dexamethasone (29)

Figure 23:
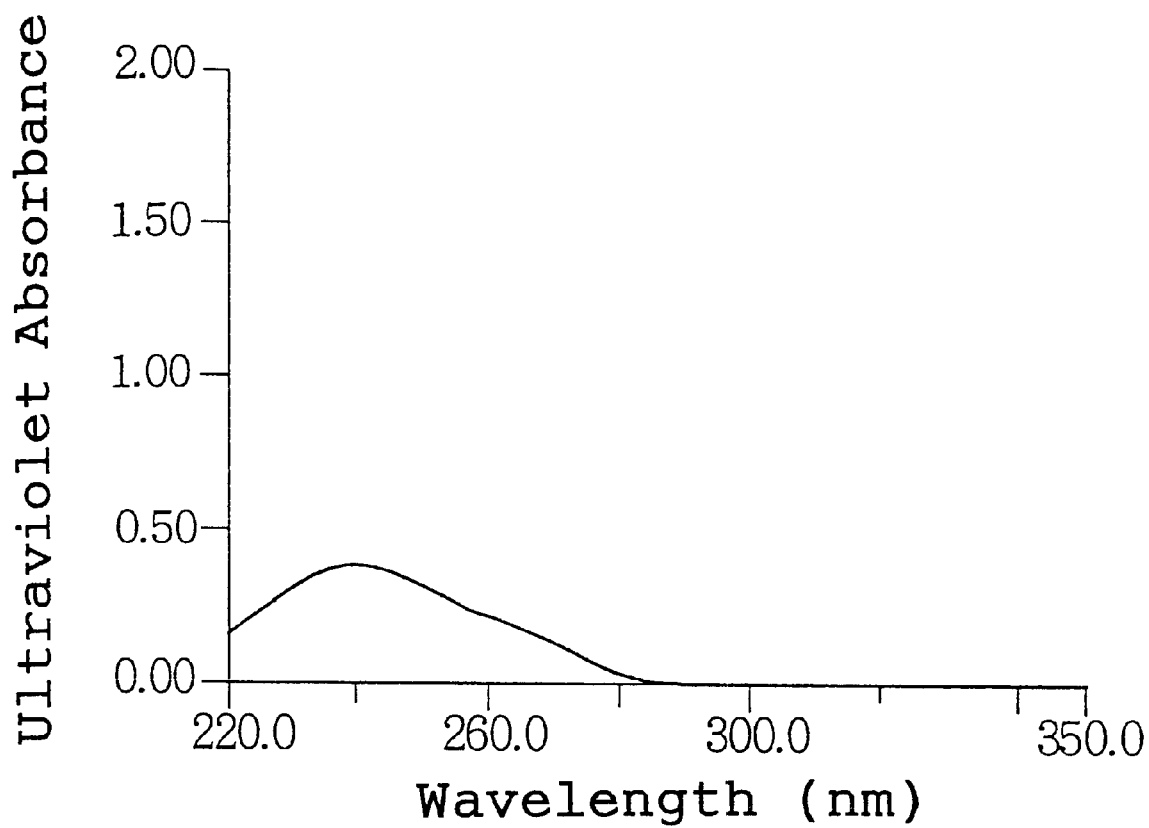
FIG. 23 is a chart showing the ultraviolet absorption spectrum of PEG-alanyl-21-dexamethasone (29) obtained in Example 8 (concentration: 163 µg/ml, solvent: water).

Z-Ala (145 mg, 0.65 mmol), dimethylaminopyridine (79 mg, 0.65 mmol) and dexamethasone (manufactured and sold by Wako Pure Chemical Industries, Ltd., Japan, 196 mg, 0.5 mmol) were dissolved in 20 ml of DMF, to thereby obtain a solution. To the obtained solution was added N,N'-diisopropylcarbodiimide (82 mg, 0.65 mmol) and stirred overnight at room temperature, to thereby obtain a reaction mixture. The obtained reaction mixture was evaporated to dryness, to thereby obtain a residue. The obtained residue was purified by silica gel column chromatography (silica gel: Art No. 9385, Silica gel 60, 200–400 mesh, manufactured and sold by E. Merck, Darmstadt, Germany, eluent: chloroform/methanol=20/1), to thereby obtain 68 mg of 21-Z-Ala-dexamethasone. 50 mg of the obtained compound was dissolved in 20 ml of dioxane, to thereby obtain a mixture. To the obtained mixture was added 50 mg of a palladium-carbon catalyst, followed by stirring for 4 hours in an atmosphere of hydrogen, to thereby obtain a reaction mixture. The obtained reaction mixture was subjected to filtration to remove the catalyst, thereby obtaining a solution. The obtained solution was evaporated to dryness under reduced pressure to thereby obtain a residue. The obtained residue was dissolved in DMF, to thereby obtain a solution. To the obtained solution were added 4-dimethylaminopyridine (61 mg, 0.5 mmol), N,N'-diisopropylcarbodiimide (63 mg, 0.5 mmol), and the CM-PEG (2,500 mg, 0.5 mmol) obtained in step 5 of Example 1, followed by stirring overnight at room temperature, to thereby obtain a reaction mixture. The obtained reaction mixture was evaporated to dryness, to thereby obtain a residue. The obtained residue was washed with 2-propanol and ether successively, followed by drying under reduced pressure, to thereby obtain 1,400 mg of compound (29) (drug complex). The ultraviolet absorption spectrum of compound (29) is shown in FIG. 23.

(7) Production of 21-propanoyl-dexamethasone (30)

Propionic acid (48 mg, 0.65 mmol), dimethylaminopyridine (79 mg, 0.65 mmol) and dexamethasone (manufactured and sold by Wako Pure Chemical Industries, Ltd., Japan, 196 mg, 0.5 mmol) were dissolved in 20 ml of DMF, to thereby obtain a solution. To the obtained solution was added N,N'-diisopropylcarbodiimide (82 mg, 0.65 mmol) and stirred overnight at room temperature, to thereby obtain a reaction mixture. The obtained reaction mixture was evaporated to dryness, to thereby obtain a residue. The obtained residue was purified by silica gel column chromatography (silica gel: Art No. 9385, Silica gel 60, 200–400 mesh, manufactured and sold by E. Merck, Darmstadt, Germany, eluent: chloroform/methanol=7/1), to thereby obtain 50 mg of compound (30).

$^1$H-NMR (DMSO-d$_6$): δ0.79 (d, 3H, 7.2 Hz), 0.89 (d, 3H), 1.07 (t, 3H, J=7.5 Hz), 1.07 (m, 1H), 1.30–1.50 (m, 3H), 1.49 (s, 3H), 1.60 (m, 2H), 1.78 (m, 1H), 2.14 (m, 2H), 2.32 (m, 2H), 2.37 (q, 2H, J=7.5 Hz), 2.62 (m, 1H), 2.94 (m, 1H), 4.14 (m, 1H), 4.80 (d, 1H, J=17.4 Hz), 5.03 (d, 1H, J=17.4 Hz), 5.16 (brs, 1H), 5.40 (m, 1H), 6.01 (s, 1H), 6.23 (d, 1H, J=9.9 Hz), 7.30 (d, 1H, J=10.2 Hz)

(8) Production of PEG-21-dexamethasone (31)

Figure 24:
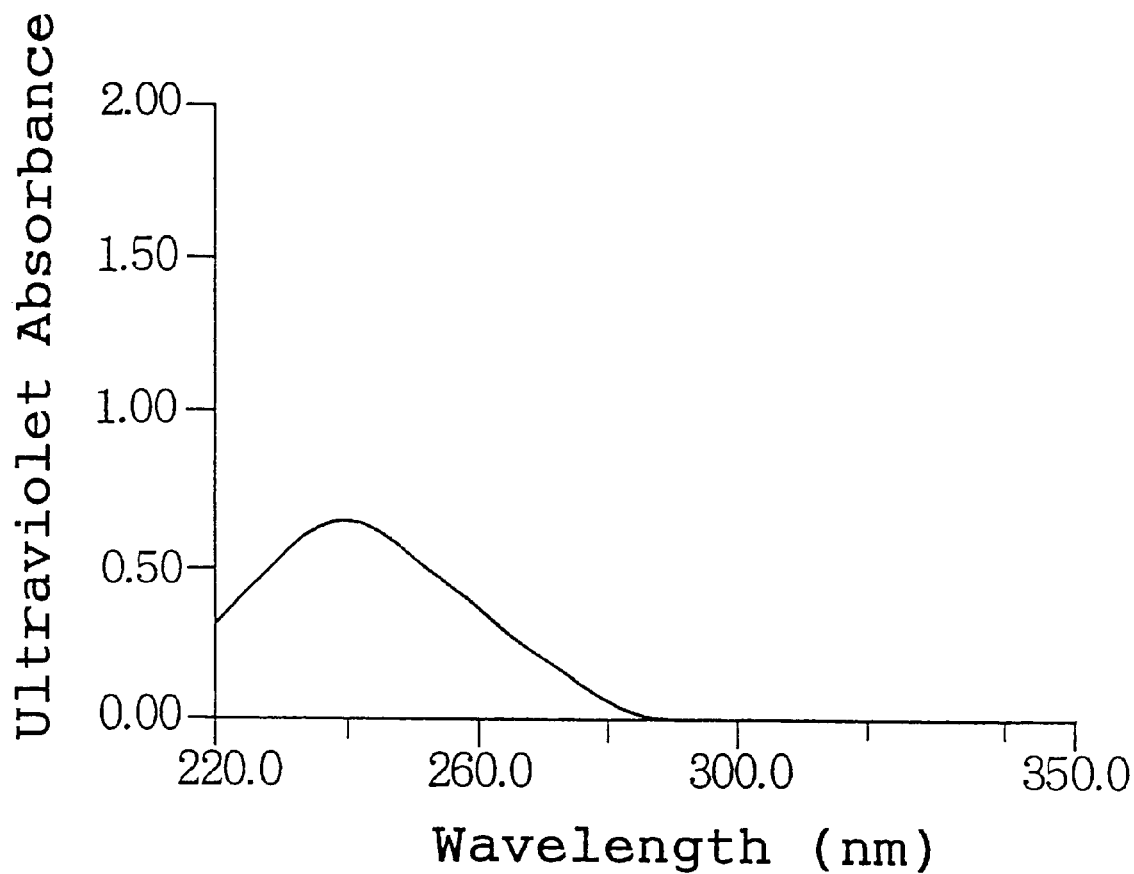
FIG. 24 is a chart showing the ultraviolet absorption spectrum of PEG-21-dexamethasone (31) obtained in Example 8 (concentration: 227 μg/ml, solvent: water).

CM-PEG (2,500 mg, 0.5 mmol) obtained in step 5 of Example 1, dimethylaminopyridine (79 mg, 0.65 mmol) and dexamethasone (manufactured and sold by Wako Pure Chemical Industries, Ltd., Japan, 196 mg, 0.5 mmol) were dissolved in 20 ml of DMF, to thereby obtain a solution. To the obtained solution was added N,N'-diisopropylcarbodiimide (82 mg, 0.65 mmol) and stirred overnight at room temperature, to thereby obtain a reaction mixture. The obtained reaction mixture was evaporated to dryness, to thereby obtain a residue. The obtained residue was collected and washed with 2-propanol and ether successively, followed by drying under reduced pressure, to thereby obtain 1,000 mg of compound (31). The ultraviolet absorption spectrum of compound (31) is shown in FIG. 24.

Reference Example 1

(Production of Trt-Gly-Gly-Phe-Gly)

(1) Synthesis of Phe-Gly-OBn

Phe-Gly.$H_2O$ (manufactured and sold by Kokusan Chemical Works Ltd., Japan, 25 g, 104 mmol) was dissolved in a mixture of para-toluenesulfonic acid monohydrate (19.8 g, 104 mmol), 25 ml of benzyl alcohol and 200 ml of toluene, to thereby obtain a mixture. The obtained mixture was refluxed for 5 hours by means of a Dean-Stark apparatus, to thereby obtain a reaction mixture. After the reaction, the obtained reaction mixture was evaporated to dryness, to thereby obtain a residue. To the obtained residue was added diethylether, to thereby obtain 40 g of Phe-Gly-OBn para-toluenesulfonate.

(2) Synthesis of Trt-Gly-Gly

Synthesis of Trt-Gly-Gly was conducted in substantially the same manner as in step 1 of Example 6. That is, Gly-Gly (manufactured and sold by PEPTIDE INSTITUTE INC., Japan, 6.6 g, 50 mmol) was dissolved in a mixture of 20 ml of $H_2O$, 40 ml of 2-propanol and 15 ml of diethylamine, to thereby obtain a solution. To the obtained solution was portionwise added trityl chloride (18.1 g, 65 mmol), followed by stirring for one hour. To the resulatant reaction mixture was added $H_2O$, to thereby generate a precipitate. The generated precipitate was collected, washed with water and then dissolved into 5 ml of acetic acid, to thereby obtain an acidic solution. The obtained acidic solution was evaporated to dryness, to thereby obtain 13.1 g of Trt-Gly-Gly.

(3) Synthesis of Trt-Gly-Gly-Phe-Gly-OBn

To 10 ml of dry DMF were added 1.54 g of Trt-Gly-Gly, 0.52 g of N-hydroxysuccinimide and 0.93 g of DCC, followed by effecting a reaction at 4° C. for 3 hours, to thereby obtain a reaction mixture. To the obtained reaction mixture was added a DMF solution containing 2.0 g of Phe-Gly-OBn para-toluenesulfonate synthesized in item (1) and 0.41 g of N-methylmorpholine, which are dissolved in 10 ml of DMF, followed by effecting a reaction at 4° C. for 15 hours, to thereby obtain a reaction mixture. A precipitate contained in the obtained reaction mixture was removed and the resultant solution was evaporated to dryness, to thereby obtain a residue. The obtained residue was purified by silica gel column chromatography (silica gel: Art No. 9365, Silica gel 60, 200–400 mesh, manufactured and sold by E. Merck, Darmstadt, Germany, eluent: chloroform/methanol=20/1), to thereby obtain 1.5 g of Trt-Gly-Gly-Phe-Gly-OBz.

(4) Synthesis of Trt-Gly-Gly-Phe-Gly 1.3 g of Trt-Gly-Gly-Phe-Gly-OBn obtained in item (3) was dissolved in 20 ml of DMF, to thereby obtain a solution. To the obtained solution were added 0.5 g of 10% palladium-carbon and 0.4 g of 4-cyclohexadiene, followed by effecting a reaction at room temperature for 30 minutes, to thereby obtain a reaction mixture. The obtained reaction mixture was subjected to filtration to remove the catalyst, to thereby obtain a solution. The obtained solution was evaporated to dryness, to thereby obtain a residue. The obtained residue was purified by silica gel column chromatography (silica gel: Art No. 9365, Silica gel 60, 200–400 mesh, manufactured and sold by E. Merck, Darmstadt, Germany, eluent: chloroform/methanol=7/1), to thereby obtain 1.0 g of Trt-Gly-Gly-Phe-Gly.

Anal. Calcd for: $C_{34}H_{34}N_4O_5$: C, 70.57; H, 5.92; N, 9.68. Found: C, 70.03; H, 6.07; N, 9.67.

Analysis of amino acids: Phe (1) 1.00, Gly (3) 2.91 Conditions of Hydrolysis: 6N HCl, 110° C., 22 hrs Reference Example 2

(Production of Z-Gly-Gly-Phe)

BOC-Phe (manufactured and sold by PEPTIDE INSTITUTE INC., Japan, 10.6 g) was dissolved in 100 ml of ethyl acetate, to thereby obtain a solution. To the obtained solution were added 10.0 g of phenacyl bromide and 5.1 g of triethylamine while cooling over ice, followed by stirring. The reaction temperature was elevated to room temperature, followed by stirring overnight to effect a reaction, thereby obtaining a reaction mixture. The obtained reaction mixture was evaporated to dryness, to thereby obtain a residue. The obtained residue was dissolved in 50 ml of ethyl acetate and the resultant solution was washed with a saturated aqueous sodium hydrogencarbonate solution and then with saturated saline. The washed solution was dried with magnesium sulfate and concentrated under reduced pressure, to thereby obtain 13.4 g of BOC-Phe phenacyl ester. Further, to 1.9 g of BOC-Phe phenacyl ester was added 5 ml of trifluoroacetic acid (TFA), followed by stirring for 10 minutes. The resultant reaction mixture was evaporated to dryness under reduced pressure for removing TFA, to thereby obtain a residue. To the obtained residue were added 20 ml of DMF, 0.61 g of N-methylmorpholine, 1.24 g of DCC, 0.81 g of HOBT and BOC-Gly (manufactured and sold by PEPTIDE INSTITUTE INC., Japan 1.05 g), followed by stirring overnight at room temperature, to thereby obtain a reaction mixture. The obtained reaction mixture was concentrated under reduced pressure, to thereby obtain a residue. The obtained residue was dissolved in 50 ml of ethyl acetate, and the resultant solution was washed with 0.1 N hydrochloride cooled with ice, saturated saline, a saturated aqueous sodium hydrogencarbonate solution and again saturated saline successively. The washed solution was dried with magnesium sulfate and concentrated under reduced pressure, to thereby obtain 1.5 g of BOC-Gly-Phe phenacyl ester. Further, to 1.6 g of BOC-Gly-Phe phenacyl ester was added 5 ml of trifluoroacetic acid (TFA), followed by stirring for 10 minutes, to thereby obtain a reaction mixture. The obtained reaction mixture was evaporated to dryness under reduced pressure for removing TFA, to thereby obtain a residue. To the obtained residue were added 20 ml of DMF, 0.40 g of N-methylmorpholine, 0.83 g of DCC, 0.54 g of HOBT and 0.84 g of Z-Gly (manufactured and sold by Kokusan Chemical Works Ltd., Japan), followed by stirring overnight at room temperature, to thereby obtain a reaction mixture. The obtained reaction mixture was concentrated under reduced pressure, to thereby obtain a residue. The obtained residue was dissolved in 50 ml of ethyl acetate and the resultant solution was washed with 0.1 N solution hydrochloride cooled with ice, saturated saline, a saturated aqueous sodium hydrogencarbonate solution and again saturated saline successively. The washed solution was dried with magnesium sulfate and concentrated under reduced pressure, to thereby obtain 1.1 g of Z-Gly-Gly-Phe phepacyl ester. 1.1 g of Z-Gly-Gly-Phe phenacyl ester was dissolved in 30 ml of 90% acetic acid, to obtain a mixture. To the obtained mixture was added 4 g of zinc dust, followed by stirring at room temperature for 5 hours, to thereby obtain a reaction mixture. The obtained reaction mixture was subjected to filtration and evaporated to dryness, to thereby obtain a residue. The obtained residue was dissolved in 30 ml of ethyl acetate and the resultant solution was washed with 10% citric acid and then with saturated saline successively, dried with magnesium sulfate and concentrated under reduced pressure, to thereby obtain 0.62 g of Z-Gly-Gly-Phe.

EXAMPLE 9

(Step 1) Production of 2'-Gly-Gly-Phe-Gly-paclitaxel hydrochloride (32)

Trt-Gly-Gly-Phe-Gly (739 mg, 1.3 mmol) obtained in Reference Example 1, dimethylaminopyridine (158 mg, 1.3 mmol) and paclitaxel (manufactured and sold by DABUR, India, 853 mg, 1.0 mmol) were dissolved in 20 ml of methylene chloride, to thereby obtain a solution. To the obtained solution was added N,N'-diisopropylcarbodiimide (164 mg, 1.3 mmol), followed by stirring at room temperature for 4 hours, to thereby obtain a reaction mixture. The obtained reaction mixture was evaporated to dryness, to thereby obtain a residue. The obtained residue was purified by silica gel column chromatography (silica gel: Art No. 9385, Silica gel 60, 200–400 mesh, manufactured and sold by E. Merck, Darmstadt, Germany, column: 4.0×50 cm, eluent: methylene chloride/methanol/acetonitrile=95/5/30), to thereby obtain 1,246 mg of 2'-Na-Trt-Gly-Gly-Phe-Gly-paclitaxel.

HRMS: m/z 1414.5763 (M+H)$^+$: the molecular weight calculated for $C_{81}H_{84}O_{18}N_5$ 1414.5811

1,100 mg of the above-obtained compound was treated with 10 ml of 75% acetic acid to effect a reaction for removing N-trityl group. The resultant compound was purified by silica gel column chromatography (silica gel: Art No. 9385, Silica gel 60, 200–400 mesh, manufactured and sold by E. Merck, Darmstadt, Germany, column: 4.0×50 cm, eluent: methylene chloride/methanol/acetonitrile=85/15/5), and subsequently converted to a corresponding hydrochloride thereof, to thereby obtain 530 mg of compound (32).

$^1$H-NMR (DMSO-d$_6$): δ1.00 (s, 3H, Me-17), 1.03 (s, 3H, Me-16), 1.42 (dd, 1H, J=15.4, 9.2 Hz, H-14b), 1.49 (s, 3H, Me-19), 1.63 (brt, 1H, J=12.1 Hz, H-6b), 1.74 (dd, 1H, J=15.4, 9.2 Hz, H-14a), 1.80 (s, 3H, Me-18), 2.11 (s, 3H, Ac-10), 2.23 (s, 3H, Ac-4), 2.30 (m, 1H, H6a), 2.72 (dd, 1H, J=13.9, 10.2 Hz, PheCH$_2$Hb), 3.02 (dd, 1H, J=13.9, 3.8 Hz, PheCH$_2$CHa), 3.52 (brs, 2H, GlyCH$_2$), 3.56 (d, 1H, J=7.2 Hz, H-3), 3.66 (dd, 1H, 16.9, 5.4 Hz, GlyCH$_2$b), 3.84 (dd, 1H, 16.9, 5.4 Hz, GlyCH$_2$a), 4.01 (dd, 2H, J=14.5, 8.4 Hz, H-20a, H-20b), 4.01 (2H, GlyCH$_2$), 4.09 (m, 1H, H-7), 4.55 (ddd, 1H, J=10.2, 8.5, 3.8 Hz, PheCH$_2$CH), 4.61 (s, 1H, OH-1), 4.89 (dd, 1H, J=8.9, 1.3 Hz, H-5), 4.92 (brs, 1H, OH-7), 5.41 (d, 1H, J=7.2 Hz, H-2), 5.43 (d, 1H, J=6.3 Hz, H-2'), 5.51 (t, 1H, J=8.5 Hz, H-3'), 5.83 (t, 1H, J=9.2 Hz, H-13), 6.29 (s, 1H, H-10), 7.10–8.00 (aromatic, 20H), 8.33 (d, 1H, PheCONH), 8.51 (t, 1H, J=5.5 Hz, GlyCONH), 8.69 (t, 1H, J=6.0 Hz, GlyCONH), 9.34 (d, 1H, J=8.5 Hz, CONH-3')

HRMS: m/z 1172.4711 (M+H)$^+$: the molecular weight calculated for $C_{62}H_{70}O_{18}N_5$ 1172.4716

Anal. Calcd for: $C_{62}H_{69}O_{18}N_5$·HCl·2.5 H$_2$O: C, 59.40; H, 6.03; N, 5.59. Found: C, 59.55; H, 6.04; N, 5.60.

(Step 2) Production of carboxymethylated dextran-2'-Gly-Gly-Phe-Gly-paclitaxel (33)

1.0 g of carboxymethylated dextran sodium salt (1) obtained in step 1 of Example 1 was dissolved in 20 ml of water. To the resultant solution was added 20 ml of N,N-dimethylformamide while cooling over ice. To the resultant mixture was added 8 ml of a solution containing 200 mg of 2'-Gly-Gly-Phe-Gly-paclitaxel (32) obtained in step 1 of Example 9, which was dissolved in a mixture of water and N,N-dimethylformamide (1:1), and 5 ml of a solution containing 1.0 g of 1-ethoxycarbonyl-2-ethoxy-1,2-dihydroquinoline dissolved in N,N-di-methylformamide, followed by stirring at room temperature for 6 hours, to thereby obtain a reaction mixture. The obtained reaction mixture was poured into 1 liter of ethanol, to thereby generate a precipitate. The generated precipitate was collected and dissolved in 100 ml of purified water. The resultant solution was poured into 1 liter of ethanol, to thereby generate a precipitate. The generated precipitate was collected and washed with acetone and ether successively, to thereby obtain 1,050 mg of compound (33) (drug complex) as a white amorphous substance.

Figure 25:
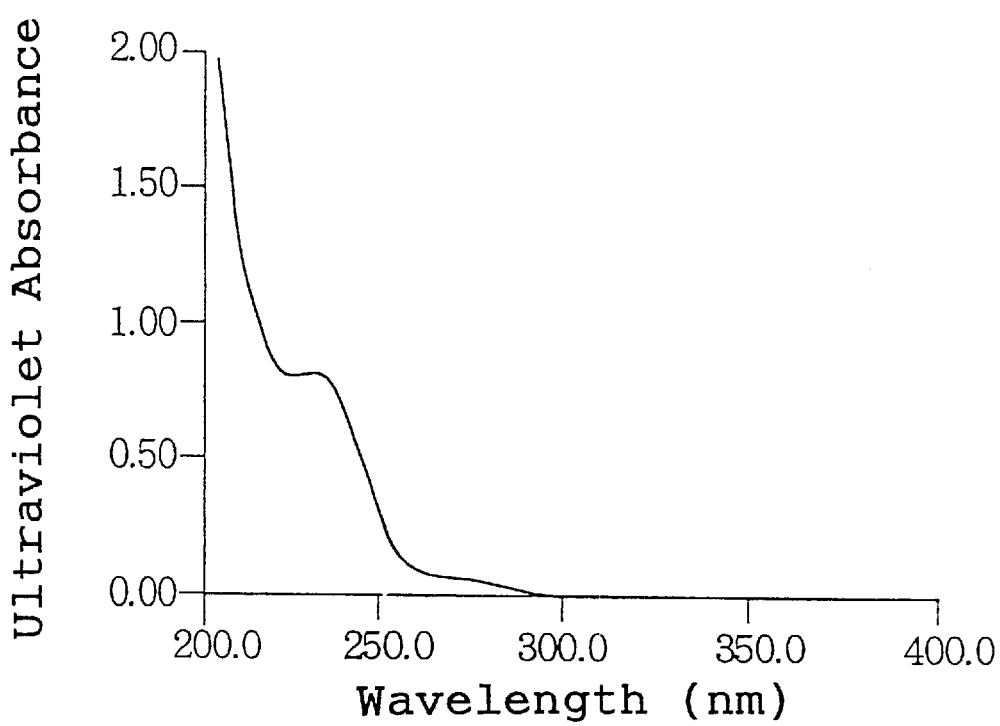
FIG. 25 is a chart showing the ultraviolet absorption spectrum of carboxymethylated dextran-2'-Gly-Gly-Phe-Gly-paclitaxel (33) obtained in Example 9 (concentration: 700 μg/ml, solvent: water).
Figure 26:
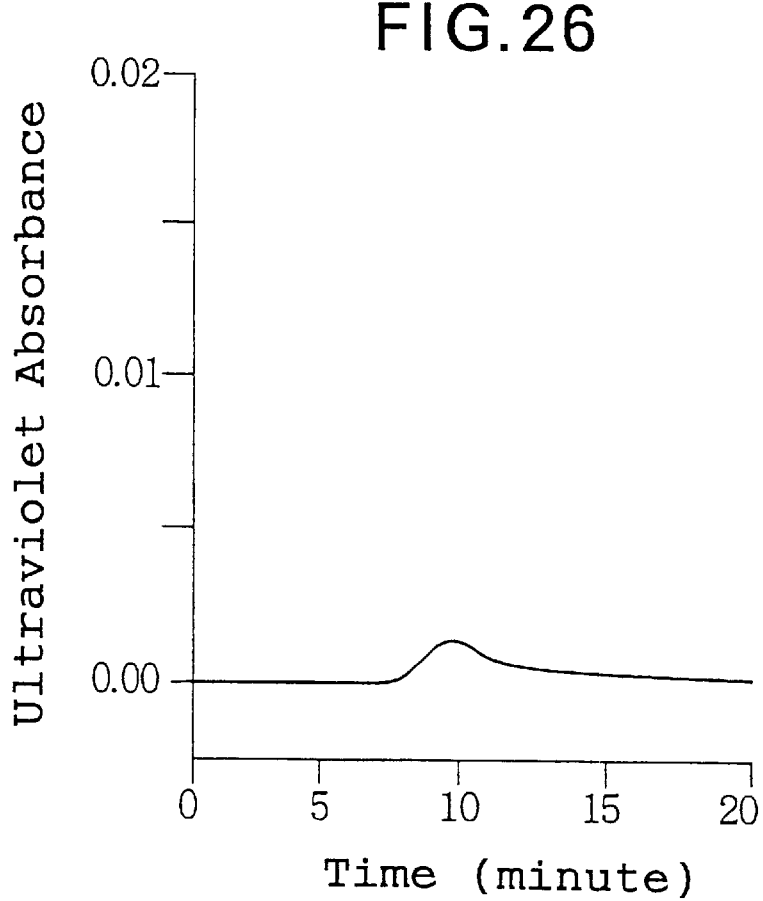
FIG. 26 is a chart showing the gel filtration chromatogram of carboxymethylated dextran-2'-Gly-Gly-Phe-Gly-paclitaxel (33) obtained in Example 9, wherein the chromatogram was obtained using an ultraviolet detector (wavelength: 220 nm).

The amount of the drug introduced into. compound (33) was calculated from the visible light absorbance at 254 nm, and found to be 3.7% by weight, based on the weight of compound (33). The gel filtration chromatogram of compound (33) was obtained using an ultraviolet detector (wavelength: 220 nm), and is shown in FIG. 25. The ultraviolet absorption spectrum of compound (33) is shown in FIG. 26.

EXAMPLE 10

(Step 1) Production of 7-Gly-Gly-Phe-Gly-paclitaxel (34)

Paclitaxel (manufactured and sold by DABUR, India, 427 mg, 0.5 mmol) was dissolved in methylene chloride, to thereby obtain a solution. To the obtained solution was added diisopropylethylamine (129 mg, 1.0 mmol), to thereby obtain a mixture. To the obtained mixture was added benzyloxycarbonyl chloride (170 mg, 1.0 mmol) while cooling over ice, followed by stirring overnight at room temperature, to thereby obtain a reaction mixture. The obtained reaction mixture was evaporated to dryness, to thereby obtain a residue. The obtained residue was purified by silica gel column chromatography (silica gel: Art No. 9385, Silica gel 60, 200–400 mesh, manufactured and sold by E. Merck, Darmstadt, Germany, column: 2.0×30 cm, eluent: methylene chloride/acetonitrile=80/20), to thereby obtain 423 mg of 2'-Z-paclitaxel.

2'-Z-paclitaxel (270 mg, 0.27 mmol) was dissolved in methylene chloride, to thereby obtain a solution. To the obtained solution were added Z-gly (85 mg, 0.41 mmol), N,N'-dicyclohexylcarbodiimide (84 mg, 0.41 mmol) and dimethylaminopyridine (50.1 mg, 0.41 mmol), followed by stirring at room temperature for 3 days, to thereby obtain a reaction mixture. The obtained reaction mixture was evaporated to dryness, to thereby obtain a residue. The obtained residue was purified by silica gel column chromatography (silica gel: Art No. 9385, Silica gel 60, 200–400 mesh, manufactured and sold by E. Merck, Darmstadt, Germany, column: 4.0×50 cm, eluent: methylene chloride/acetonitrile=80/20), to thereby obtain 300 mg of 2'-Z-7-Z-Gly-paclitaxel.

2'-Z-7-Z-Gly-paclitaxel (200 mg, 0.16 mmol) was dissolved in 100 ml of ethyl acetate, to thereby obtain a solution. To the obtained solution was added a palladium-carbon catalyst, followed by introducing thereinto hydrogen gas while stirring, to thereby effect a reaction. After completion of the reaction, the resultant reaction mixture was subjected to filtration to remove the catalyst, to thereby obtain a solution. The obtained solution was evaporated to dryness, to thereby obtain a residue. The obtained residue was purified by silica gel column chromatography (silica gel Art No. 9385, Silica gel 60, 200–400 mesh, manufactured and sold by E. Merck, Darmstadt, Germany, column: 4.0×50 cm, eluent: methylene chloride/acetonitrile=50/50), to thereby obtain 87 mg of 7-Gly-paclitaxel.

7-Gly-paclitaxel (70 mg, 0.09 mmol) was dissolved in 20 ml of N,N-dimethylformamide, to thereby obtain a solution. To the obtained solution were added the Z-Gly-Gly-Phe (58 mg, 0.13 mmol) obtained in Reference Example 2, water-soluble carbodiimide (26 mg, 0.13 mmol) and 1-hydroxybenzotriazole (18 mg, 0.13 mmol), followed by stirring at room temperature for 3 days, to thereby obtain a reaction mixture. The obtained reaction mixture was evaporated to dryness, to thereby obtain a residue. The obtained residue was purified by silica gel column chromatography (silica gel: Art No. 9385, Silica gel 60, 200–400 mesh, manufactured and sold by E. Merck, Darmstadt, Germany, column: 4.0×50 cm, eluent: methylene chloride/methanol/acetonitrile=85/15/5), to thereby obtain 94 mg of 7-Z-Gly-Gly-Phe-Gly-paclitaxel.

7-Z-Gly-Gly-Phe-Gly-paclitaxel (80 mg, 0.06 mmol) was dissolved in 20 ml of methanol, to thereby obtain a solution. To the obtained solution was added a palladium-carbon catalyst, followed by introducing hydrogen gas thereinto while stirring, to thereby effect a reaction. After completion of the reaction, the reaction mixture was subjected to filtration to remove the catalyst, to thereby obtain a solution. The obtained solution was evaporated to dryness, to thereby obtain a residue. The obtained residue was purified by silica gel column chromatography (silica gel: Art No. 9385, Silica gel 60, 200–400 mesh, manufactured and sold by E. Merck, Darmstadt, Germany, column: 4.0×30 cm, eluent: methylene chloride/methanol/acetonitrile=95/5/30), to thereby obtain 50 mg of compound (34).

$^1$H-NMR (DMSO-$d_6$): δ0.99 (s, 3H, Me-17), 1.05 (s, 3H, Me-16), 1.67 (s, 3H, Me-19), 1.68 (m, 1H, H6b), 1.75 (s, 3H, Me-18), 1.79 (dd, 1H, J=15.3, 8.9 Hz, H-14b), 1.90 (dd, 1H, J=15.3, 8.9 Hz, H-14a), 2.15 (s, 3H, Ac-10), 2.26 (s, 3H, Ac-4), 2.42 (m, 1H, H-6a), 2.74 (dd, 1H, J=13.9, 10.5 Hz, PheCH$_2$CHb), 3.05 (dd, 1H, J=13.9, 3.8 Hz, PheCH$_2$CHa), 3.54 (brs, 2H, GlyCH$_2$), 3.66 (dd, 1H, J=16.8, 5.3 Hz, GlyCH$_2$b), 3.69 (dd, 1H, J=16.8, 5.3 Hz, GlyCH$_2$a), 3.72 (d, 1H, J=6.8 Hz, H-3), 3.80 (dd, 1H, J=16.8, 5.8 Hz, GlyCH$_2$b), 3.85 (dd, 1H, J=16.8, 5.8 Hz, GlyCH$_2$a), 4.06 (s, 2H, H-20), 4.57 (ddd, 1H, J=10.5, 8.9, 3.8 Hz, PheCH$_2$CH), 4.62 (brt, 1H, J=7.0 Hz, H-2'), 4.85 (s, 1H, OH-1), 4.99 (d, 1H, J=9.8 Hz, H-5), 5.42 (t, 1H, J=8.1 Hz, H-3'), 5.43 (d, 1H, J=6.8 Hz, H-2), 5.47 (dd, 2H, J=10.4, 7.6 Hz, H-7), 5.91 (t, 1H, J=8.5 Hz, H-13), 6.23 (d, 1H, OH-2'), 7.00–8.00 (aromatic, 20H), 8.05 (brs, 1H, NH$_2$), 8.30 (d, 1H, J=8.9 Hz, PheCONH), 8.47 (t, 1H, J=5.6 Hz, GlyCONH), 8.56 (t, 1H, J=5.5 Hz, GlyCONH), 9.00 (d, 1H, J=8.5 Hz, CONH-3')

(Step 2) Production of carboxymethylated dextran-7-Gly-Gly-Phe-Gly-paclitaxel (35)

1.0 g of carboxymethylated dextran sodium salt (1) obtained in step 1 of Example 1 was dissolved in 20 ml of water. To the resultant solution was added 20 ml of N,N-dimethylformamide while cooling over ice. To the resultant mixture was added 8 ml of a solution containing 180 mg of 7-Gly-Gly-Phe-Gly-paclitaxel (34) obtained in step 1 of Example 10, which was dissolved in a mixture of water and N,N-dimethylformamide (1:1), and 5 ml of a solution containing 1.0 g of 1-ethoxycarbonyl-2-ethoxy-1,2-dihydroquinoline dissolved in N,N-di-methylformamide, followed by stirring at room temperature for 6 hours, to thereby obtain a reaction mixture. The obtained reaction mixture was poured into 1 liter of ethanol, to thereby generate a precipitate. The generated precipitate was collected and dissolved in 100 ml of purified water. The resultant solution was poured into 1 liter of ethanol, to thereby generate a precipitate. The generated precipitate was collected and washed with acetone and ether successively, to thereby obtain 1,050 mg of compound (35) (drug complex) as a white amorphous substance.

Figure 27:
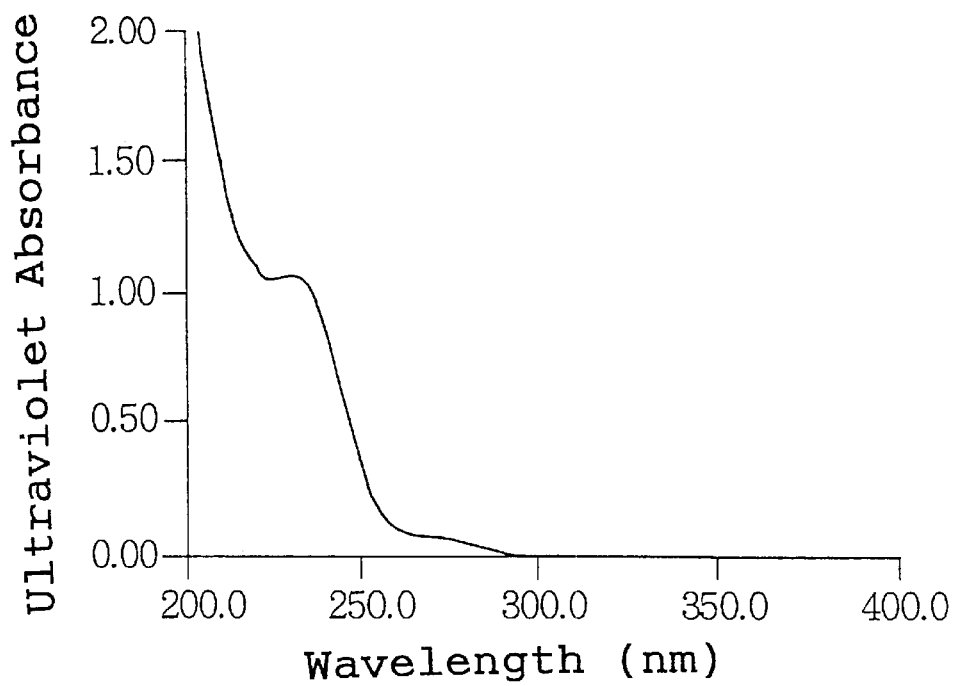
FIG. 27 is a chart showing the ultraviolet absorption spectrum of carboxymethylated dextran-7-Gly-Gly-Phe-Gly-paclitaxel (35) obtained in Example 10 (concentration: 428 μg/ml, solvent: water).
Figure 28:
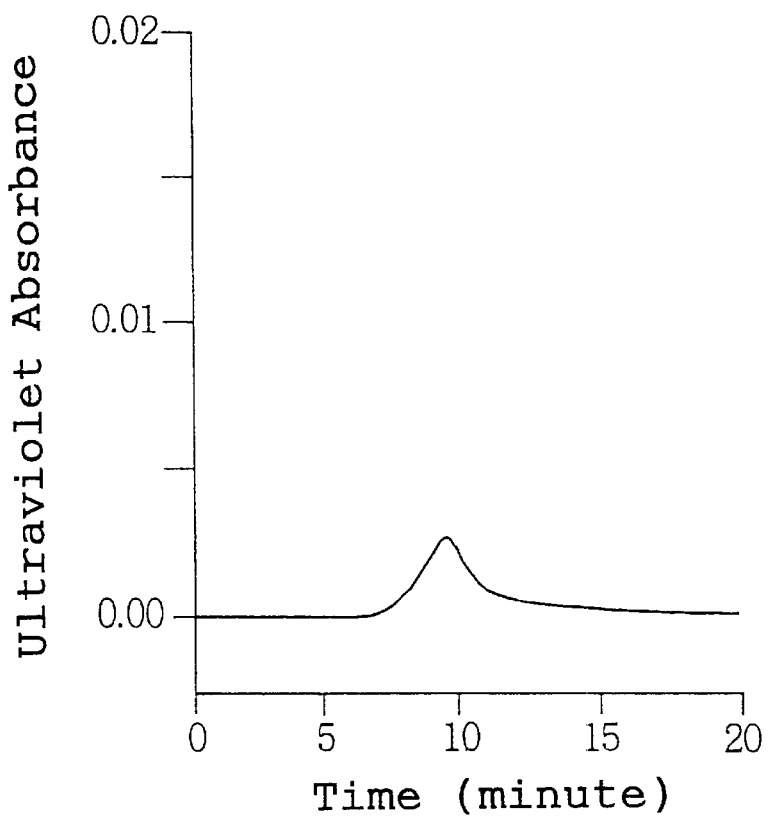
FIG. 28 is a chart showing the gel filtration chromatogram of carboxymethylated dextran-7-Gly-Gly-Phe-Gly-paclitaxel (35) obtained in Example 10, wherein the chromatogram was obtained using an ultraviolet detector (wavelength: 220 nm).

The amount of the drug introduced into compound (35) was calculated from the visible light absorbance at 254 nm, and found to be 7.4% by weight, based on the weight of compound (35). The gel filtration chromatogram of compound (35) was obtained using an ultraviolet detector (wavelength: 220 nm), and is shown in FIG. 27. The ultraviolet absorption spectrum of compound (35) is shown in FIG. 28.

Experiment 1

Dissolution of Compounds (3) and (15) in Physiological Saline 50 mg of compound (3) obtained in Example 1 was successfully dissolved completely in 0.5 ml of physiological saline. This means that 37 mg of paclitaxel dissolved in 10 ml of physiological saline, i.e., the dissolution ratio of compound (3) in terms of paclitaxel was 3.7 mg/ml (physiological saline).

50 mg of compound (15) obtained in Example 4 was successfully dissolved completely in 0.5 ml of physiological saline. This means that 16 mg of paclitaxel was dissolved in 10 ml of physiological saline, i.e. the dissolution ratio of compound (15) in terms of paclitaxel was 1.6 mg/ml (physiological saline).

On the other hand, 1 mg of paclitaxel (manufactured and sold by DABUR, India) could not be dissolved completely in 10 ml of physiological saline.

Experiment 2

Evaluation of the Release of Paclitaxel from Compounds (3), (7), (11) and (15) in Mouse Serum and Human Serum Each of compounds (3), (7), (11) and (15) (drug complexes) respectively obtained in Examples 1, 2, 3 and 4 was individually dissolved in physiological saline so that the concentration thereof in terms of paclitaxel was 125 µg/ml, to thereby obtain four solutions. 20 µl of each of the above-obtained four solutions was individually added to each of 200 µl of mouse serum and 200 µl of human serum, and the amounts of paclitaxel released from the respective compounds at 37° C. were determined as follows.

Figure 29:
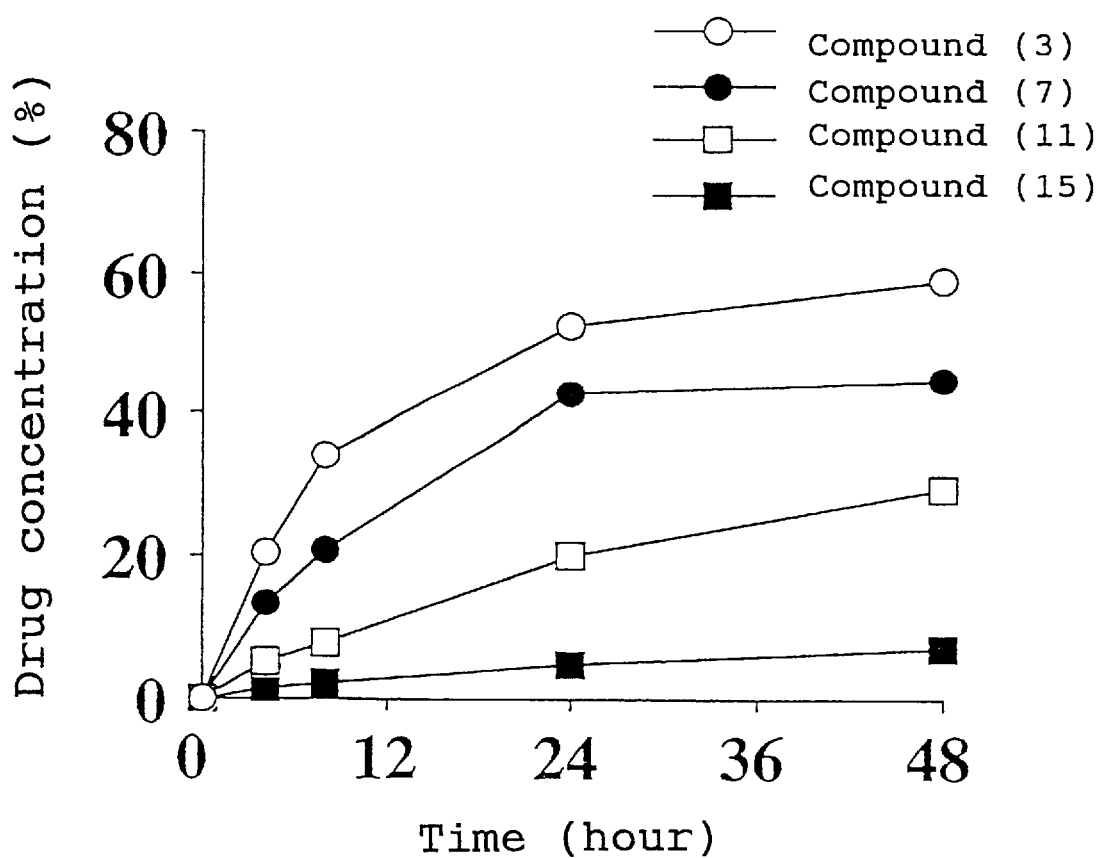
FIG. 29 is a graph showing the changes (with the lapse of time) of the release of paclitaxel from compounds (3), (7), (11) and (15) in mouse serum at 37° C., wherein the changes were measured in Experiment 2.
Figure 30:
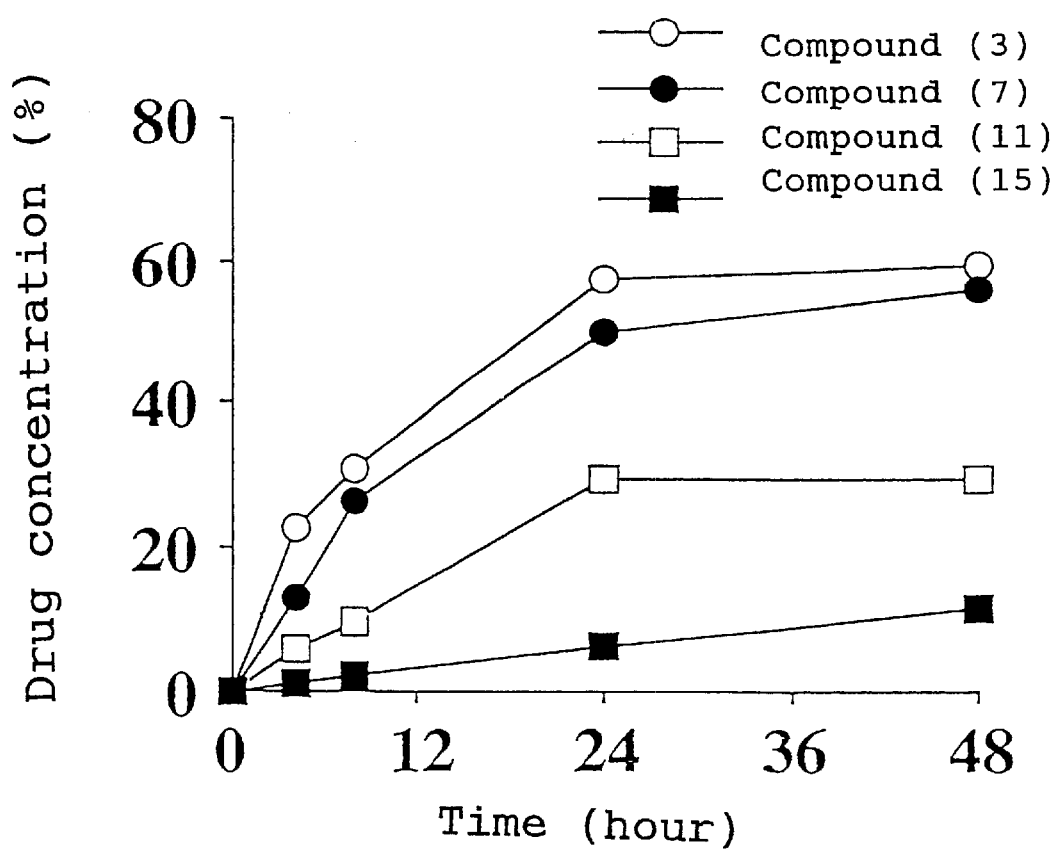
FIG. 30 is a graph showing the changes (with the lapse of time) of the release of paclitaxel from compounds (3), (7), (11) and (15) in human serum at 37° C., wherein the changes were measured in Experiment 2.

The recovery of paclitaxel from the serum by solid-phase extraction and subsequent determination of the amount of paclitaxel released from each of compounds (3), (7), (11) and (15) in serum by HPLC were conducted according to the method described in Yakugaku Zasshi, 114, P.351–355 (1994). The changes (with the lapse of time) of the release of paclitaxel from the compounds in mouse serum and human serum are shown in FIGS. 29 and 30, respectively.

With respect to the rates of the release of paclitaxel from the compounds, the same tendency was observed in both of mouse serum and human serum. The magnitudes of the rates of the release of paclitaxel from the respective compounds were in the order of (3)>(7)>(11)>(15). The rate of the release of paclitaxel has a correlation with the magnitude of the steric hindrance of the amino acid used as a spacer in the compound (drug complex).

Experiment 3

Antitumor Assays (1)

Test sample solutions were prepared by separately dissolving, into physiological saline, compounds (3), (7) and (15) respectively obtained in Examples 1, 2 and 3. Further, a control solution was prepared by dissolving paclitaxel per se into a mixture of ethanol, Cremophore EL (manufactured and sold by Sigma, U.S.A.) and physiological saline. Thus, four types of solutions, namely, three different types of test sample solutions and one control solution were obtained.

Twenty-eight female C57BL/6 mice (six weeks old) were divided into four groups, each consisting of seven mice, and subsequently, B16 melanoma cells were intradermally transplanted to the groin of each of the mice ($5 \times 10^6$ cells per mouse). After eight days from the transplantation, the above-mentioned four types of solutions were administered to the transplanted mice at the tails thereof intravenously so that the mice belonging to the same group received the administration of the same type of solution. The amounts of the test sample solutions, administered to the mice of the different groups are all the same, and each of the doses of compounds (3), (7) and (15) was 50 mg/kg in terms of paclitaxel. With respect to the control solution, the dose of paclitaxel was 50 mg/kg.

Separately, a group consisting of thirteen mice, which were transplanted with B16 melanoma cells in the same manner as mentioned above, was provided. Each of the mice of such group received the administration of physiological saline, to thereby obtain a non-treated group of mice.

After six days from the administration of the test sample solution, the control solution and the physiological saline to the mice, evaluation was made of the antitumor activity of each compound in terms of the relative average tumor volume (%), namely, the ratio of the average tumor volume of the mice of each of the four treated groups (the mice of the treated groups had received the administration of the three types of test sample solutions and the control solution, respectively), relative to the average tumor volume of the mice of the non-treated group (the mice of the non-treated group had received the administration of physiological saline).

The tumor volume was determined as follows. The external major and minor diameters (a and b, respectively) (each in mm) of the tumor were measured, and the tumor volume (V) was obtained according to the following formula.

$$V = \frac{a \times b^2}{2} (mm)^3$$

Figure 31:
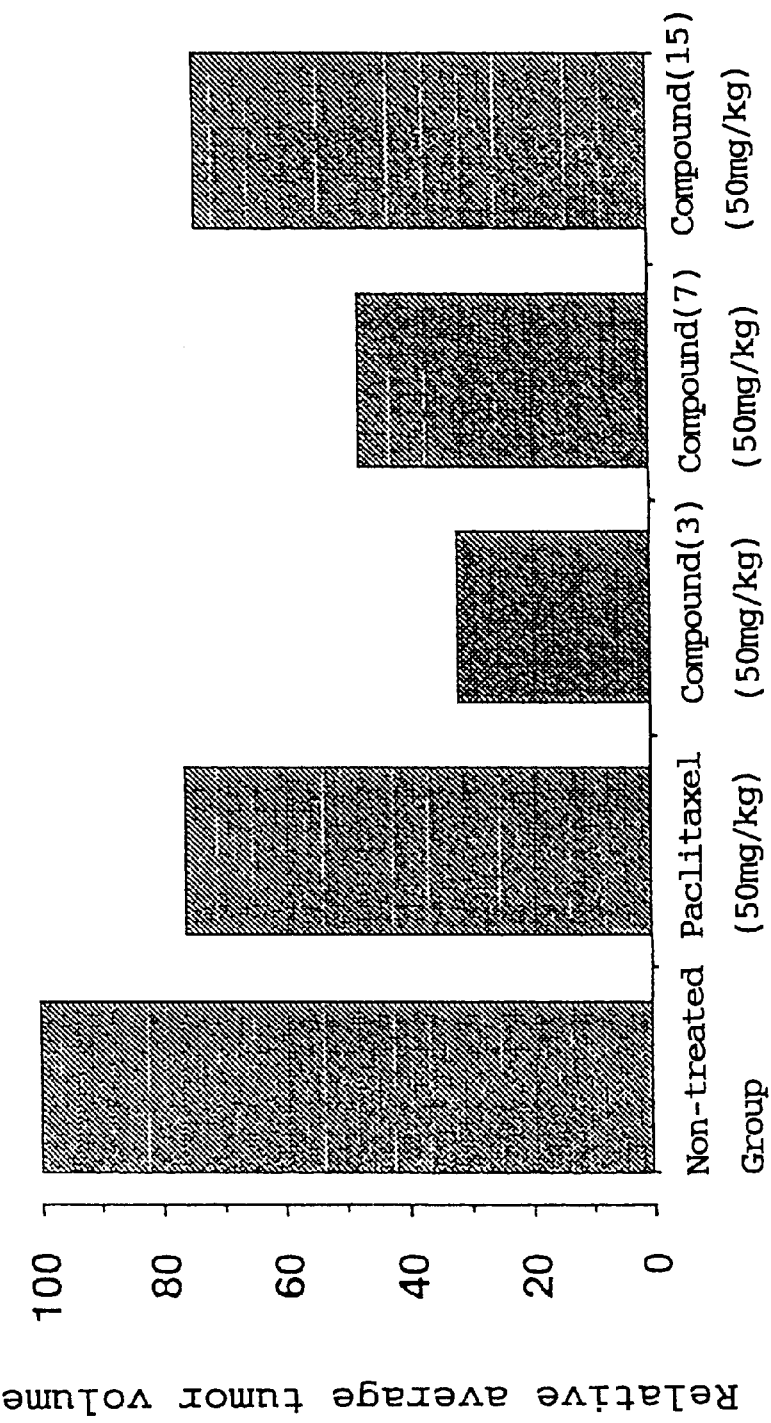
FIG. 31 is a graph showing the antitumor effects of compounds (3), (7) and (15), wherein the effects were evaluated in Experiment 3 by antitumor assay, using tumor-transplanted mice.

The relationship between the doses of compounds (3), (7) and (15) and the relative average tumor volumes (%) is shown in FIG. 31.

The antitumor activity of compound (3) of the present invention, observed with respect to the group of mice which had received the administration of 50 mg/kg (in terms of paclitaxel) of compound (3), was significantly excellent, as compared to the antitumor activity of paclitaxel, observed with respect to the group of mice which had received the administration of paclitaxel per se.

The antitumor activity of compound (7) of the present invention, observed with respect to the group of mice which had received the administration of 50 mg/kg (in terms of paclitaxel) of compound (7), was also excellent, as compared to the antitumor activity of paclitaxel, observed with respect to the group of mice which had received the administration of paclitaxel per se.

The antitumor activity of compound (15), observed with respect to the group of mice which had received the administration of 50 mg/kg (in terms of paclitaxel) of compound (15), was relatively weak, as compared to the antitumor activity of paclitaxel, observed with respect to the group of mice which had received the administration of paclitaxel per se.

The magnitudes of the antitumor activities of the respective compounds were in the order of (3)>(7)>(15). The antitumor activity has a correlation with the rate of the release of the drug, which is described in Example 2.

Experiment 4

Evaluation of the Release of Paclitaxel from Compounds (3), (19), (21) and (23) in Mouse Serum and Human Serum Each of compounds (3), (19), (21) and (23) (drug complexes) respectively obtained in Examples 1, 5, 6, and 7 was individually dissolved in physiological saline so that the concentration thereof in terms of paclitaxel was 125 µg/ml, to thereby obtain four solutions. 20 µg of each of the above-obtained four solutions was individually added to each of 200 µl of mouse serum and human serum, and the amounts of paclitaxel released from the respective compounds at 37° C. were determined as follows.

Figure 32:
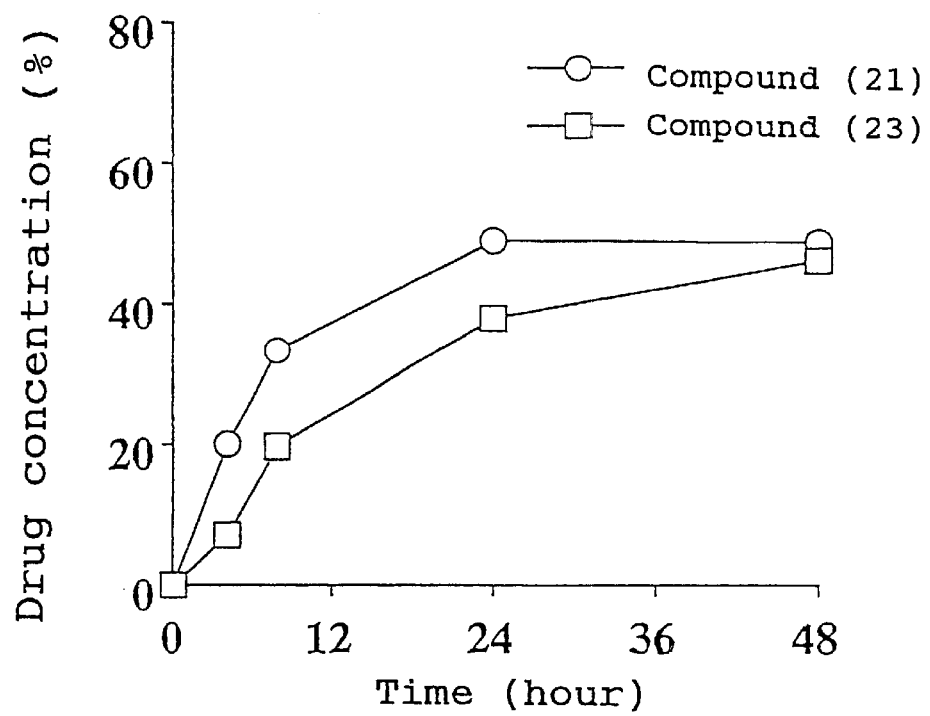
FIG. 32 includes two graphs showing the changes (with the lapse of time) of the release of paclitaxel from compounds (3) and (19), and (21) and (23) in mouse serum at 37° C., wherein the changes were measured in Experiment 4.
Figure 32:
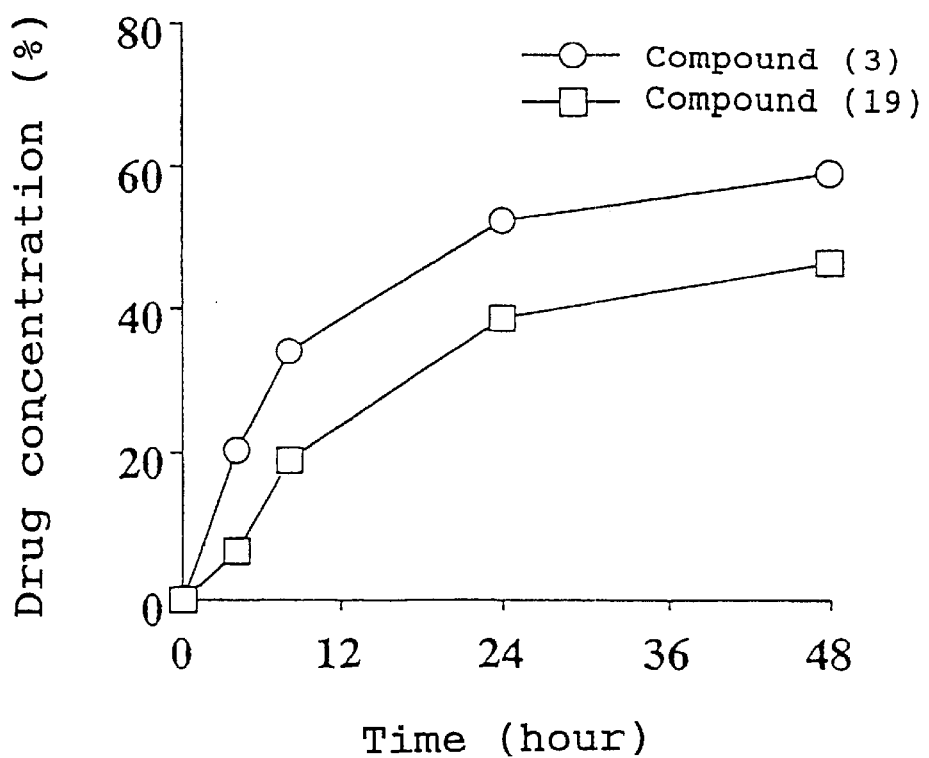
Figure 33:
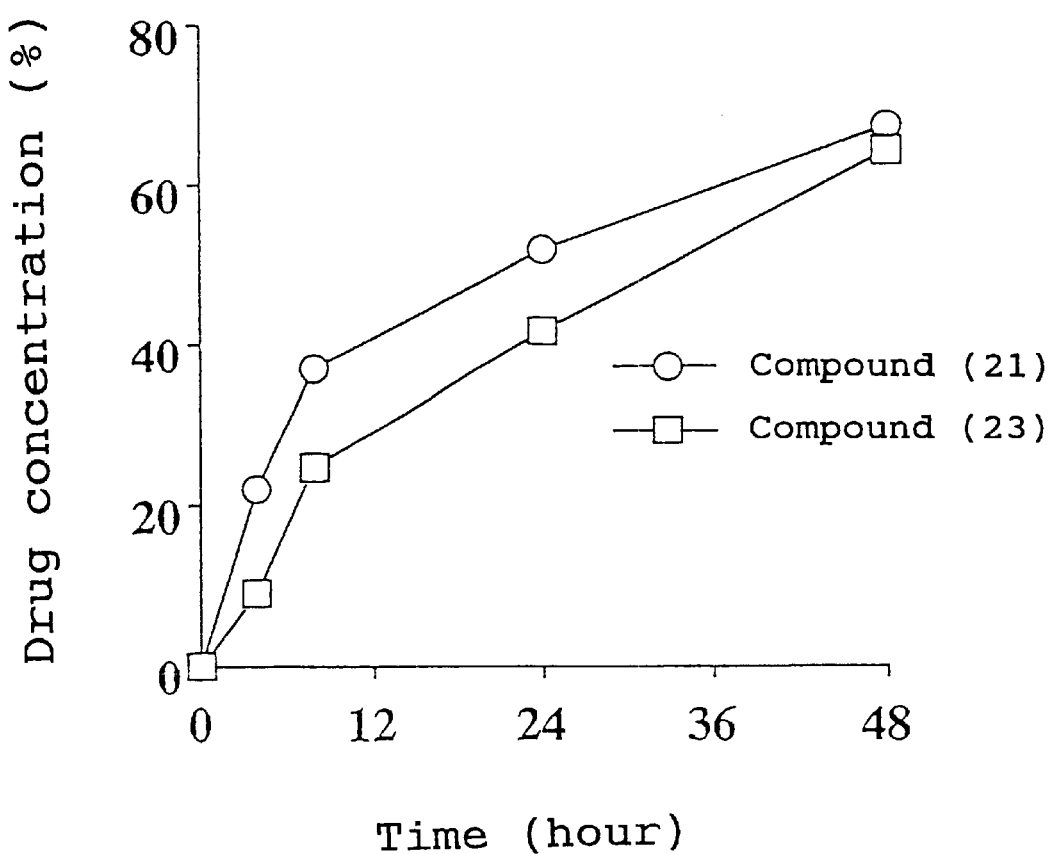
FIG. 33 is a graph showing the changes (with the lapse of time) of the release of paclitaxel from compounds (21) and (23) in human serum at 37° C., wherein the changes were measured in Experiment 4.

The recovery of paclitaxel from the serum by solid-phase extraction and subsequent determination of the amount of paclitaxel released from each of compounds (3), (19), (21) and (23) in serum by HPLC were conducted according to the method described in Yakugaku Zasshi, 114, P.351–355 (1994). The changes (with the lapse of time) of the release of paclitaxel in mouse serum and human serum are shown in FIGS. 32 and 33, respectively.

With respect to the rates of the release of paclitaxel from compounds (3) and (19) in mouse serum, the magnitudes of the rates of the release from the respective compounds were in the order of (3)>(19). The rate of the release of paclitaxel has a correlation with the magnitude of the steric hindrance of the amino acid used as a spacer in the compound (drug complex).

Further, with respect to the rates of the release of paclitaxel from compounds (21) and (23) in both of mouse serum and human serum, the magnitudes of the rate of the release of paclitaxel from the respective compounds were in the order of (21)>(23). The rate of the release of paclitaxel has a correlation with the magnitude of the steric hindrance of the amino acid directly bonded to the drug, wherein the amino acid is contained in the peptide used as a spacer in the compound (drug complex).

Experiment 5

Dissolution of Compounds (5) and (17) in Physiological Saline 25 mg of compound (5) obtained in Example 1 was successfully dissolved completely in 1 ml of a physiological saline. This means that 36 mg of paclitaxel dissolved in 10 ml of physiological saline, i.e., the dissolution ratio of compound (5) in terms of paclitaxel was 3.6 mg/ml (physiological saline).

20 mg of compound (17) obtained in Example 4 was successfully dissolved completely in 1 ml of physiological saline. This means that 28 mg of paclitaxel was dissolved in 10 ml of physiological saline, i.e., the dissolution ratio of compound (17) in terms of paclitaxel was 2.8 mg/ml (physiological saline).

On the other hand, 1 mg of paclitaxel (manufactured and sold by DABUR, India) could not be dissolved completely in 10 ml of physiological saline.

Experiment 6

Evaluation of the Release of Paclitaxel from Compounds (5), (9), (13) and (17) in Mouse Serum and Human Serum Each of compounds (5), (9), (13) and (17) (drug complexes) respectively obtained in Examples 1, 2, 3 and 4 was individually dissolved in physiological saline so that the concentration thereof in terms of paclitaxel was 250 µg/ml, to thereby obtain four solutions. 20 µl of each of the above-obtained four solutions was individually added to each of 200 µl of mouse serum and human serum, and the amounts of paclitaxel released from the respective compounds at 37° C. were determined as follows.

Figure 34:
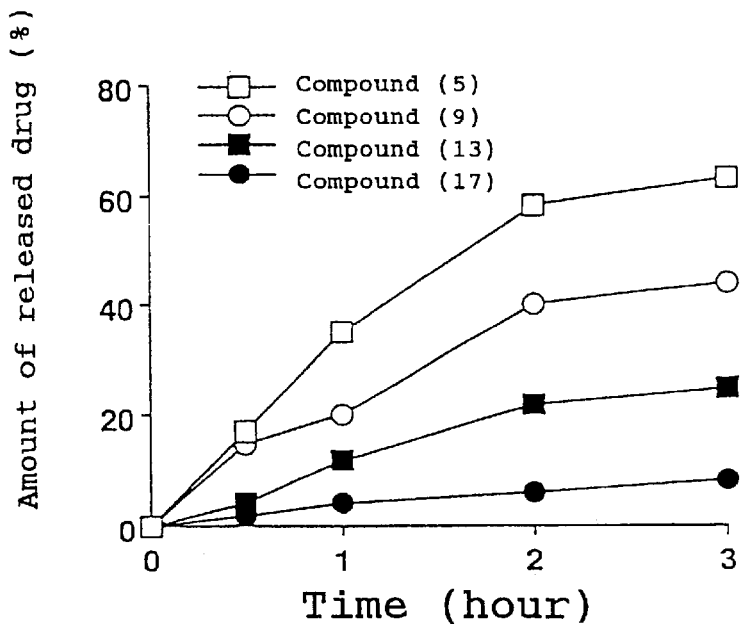
FIG. 34 is a graph showing the changes (with the lapse of time) of the release of a drug from compounds (5), (9), (13) and (17) in mouse serum at 37° C., wherein the changes were measured in Experiment 6.
Figure 35:
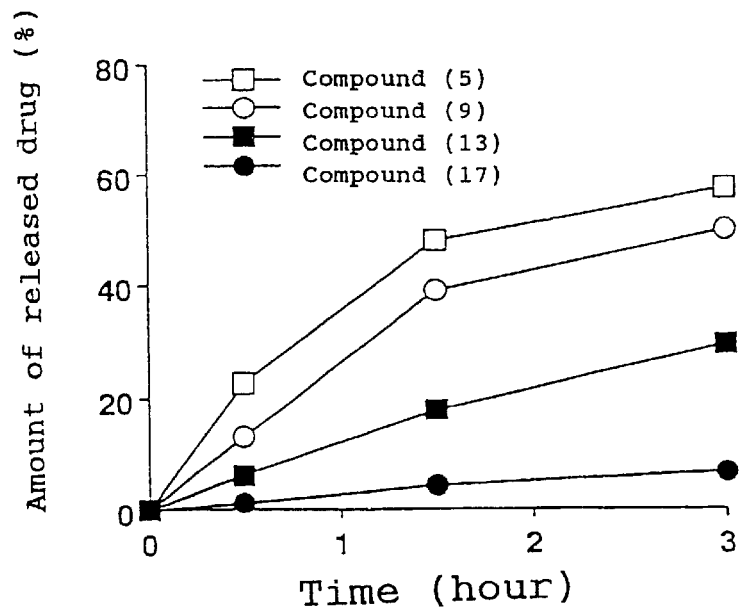
FIG. 35 is a graph showing the changes (with the lapse of time) of the release of a drug from compounds (5), (9), (13) and (17) in human serum at 37° C., wherein the changes were measured in Experiment 6.

The recovery of paclitaxel from the serum by solid-phase extraction and subsequent determination of the amount of paclitaxel released from each of compounds (5), (9), (13) and (17) in serum by HPLC were conducted according to the method described in Yakugaku Zasshi, 114, P.351–355 (1994). The changes (with the lapse of time) of the release of paclitaxel from the compounds in mouse serum and human serum are shown in FIGS. 34 and 35, respectively.

With respect to the rates of the release of paclitaxel from the compounds, the same tendency was observed in both of mouse serum and human serum. The magnitudes of the rates of the release of paclitaxel from the respective compounds were in the order of (5)>(9)>(13)>(17). The rate of the release of paclitaxel has a correlation with the magnitude of the steric hindrance of the amino acid used as a spacer in the compound (drug complex).

Experiment 7

Evaluation of the Release of Dexamethasone from Compounds (24), (26), (28) and (30) in Mouse Serum and Human Serum Each of compounds (24), (26), (28) and (30) (drug complexes) obtained in Example 8 was dissolved in physiological saline so that the concentration thereof in terms of dexamethasone was 80 µg/ml, to thereby obtain four solutions. 50 µl of each of the above-obtained four solutions was individually added to each of 250 µl of mouse serum and 250 µl of human serum, and the amounts of dexamethasone released from the respective compounds at 37° C. were determined as follows.

The recovery and quantitative analysis of dexamethasone in serum were conducted as follows: 250 µl of phosphate buffer (pH 7.4) was added to 250 ml of each of the sera to which the above-mentioned solution was added, to thereby obtain a mixture. To the obtained mixture was added 3 ml of a solution of hydrocortisone acetate (as an internal standard for the below-mentioned HPLC analysis, the concentration of hydrocortisone acetate: 10 ng/ml) in a mixture of acetonitrile and methanol (acetonitrile/methanol=4/1) and subjected to centrifugation (3,000 rpm, 10 minutes, 4° C.). To 700 µl of the resultant supernatant was added 700 pl of distilled water, to thereby obtain a mixture. The obtained mixture was subjected to filtration with a membrane filter (pore size 0.2 µm), and the resultant filtrate was used as a sample for the quantitative analysis of dexamethasone by HPLC under the following conditions. obtained mixture was subjected to filtration with a membrane filter (pore size 0.2 µm), and the resultant filtrate was used as a sample for the quantitative analysis of dexamethasone by HPLC under the following conditions.

The conditions for HPLC

Column: Asahipak HIKARISIL C18 (4.6×150 mm)

Flow rate: 1.0 ml/min.

Column temperature: room temperature

The detected wavelength: 254 nm

Mobile phase: Linear gradient 0 min.: 20% aqueous acetonitrile (20% $CH_3CN/H_2O$)

20 min.: 50% aqueous acetonitrile (50% $CH_3CN/H_2O$)

With respect to the rates of the release of dexamethasone from the compounds, the same tendency was observed in both of mouse serum and human serum. The magnitudes of the rates of the release of dexamethasone from the respective compounds were in the order of (30)>(26)>(28)>(24). The rate of the release of dexamethasone has a correlation with the magnitude of the steric hindrance of the amino acid used as a spacer in the compound (drug complex). Illustratively stated, 98% or more of dexamethasone introduced into compound (30) was released from compound (30) very quickly, whereas approximately 95% of dexamethasone introduced into compound (26) was released from compound (26), approximately 70% of dexamethasone introduced into compound (28) was released from compound (28), and only 10% or less of dexamethasone introduced into compound (24) was released from compound (24).

Experiment 8

Dissolution of Compounds (33) and (35) in Physiological Saline 1 g of compound (33) obtained in Example 9 was successfully dissolved completely in 10 ml of a physiological saline. This means that 37 mg of paclitaxel dissolved in 10 ml of physiological saline, i.e. the dissolution ratio compound (33) in terms of paclitaxel was 3.7 mg/ml (physiological saline).

1 g of compound (35) obtained in Example 10 was successfully dissolved completely in 10 ml of physiological saline. This means that 74 mg of paclitaxel was dissolved in 10 ml of physiological saline, i.e. the dissolution ratio of compound (35) in terms of paclitaxel was 7.4 mg/ml (physiological saline).

On the other hand, 1 mg of paclitaxel (manufactured and sold by DABUR, India) could not be dissolved completely in 10 ml of physiological saline.

Experiment 9

Evaluation of the Release of Paclitaxel from Compounds (33) and (35) in Serum of B-16 Melanoma-transplanted Mouse Each of compounds (33) and (35) (drug complexes) respectively obtained in Examples 9 and 10 was individually dissolved in physiological saline so that the concentration thereof in terms of paclitaxel was 250 µg/ml, to thereby obtain two solutions. 20 µl of each of the above-obtained two solutions was added to 200 µl of serum of B-16 melanoma-transplanted mouse, and the amounts of paclitaxel released from the respective compounds at 37° C. were determined as follows.

Figure 36:
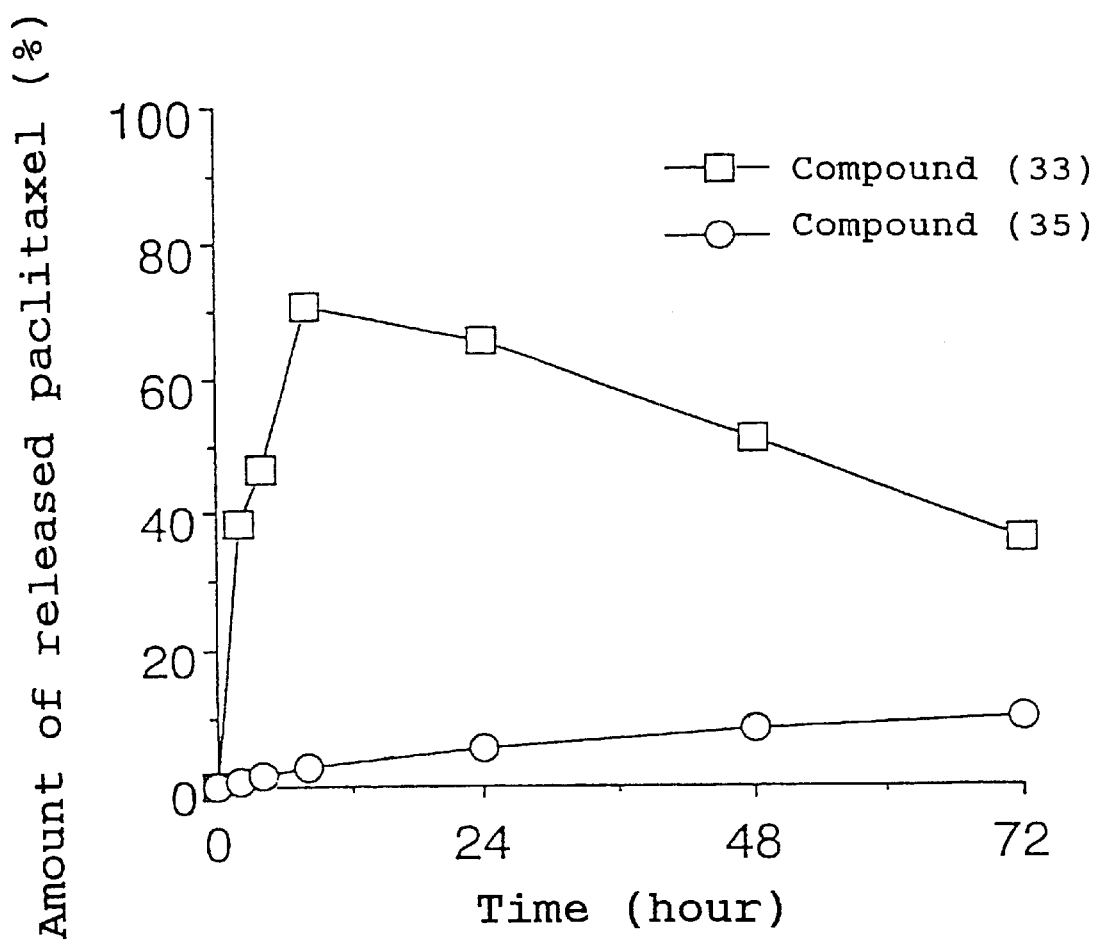
FIG. 36 is a graph showing the changes (with the lapse of time) of the release of a drug from compounds (33) and (35) in mouse serum at 37° C., wherein the changes were measured in Experiment 9.

The recovery of paclitaxel from the serum by solid-phase extraction and subsequent determination of the amount of paclitaxel released from each of compounds (33) and (35) in serum by HPLC were conducted according to the method described in Yakugaku Zasshi, 114, P.351–355 (1994). The changes (with the lapse of time) of the release of paclitaxel from the compounds in mouse serum and human serum are shown in FIG. 36.

In mouse serum, the concentration of paclitaxel released from compound (33) became maximum at a point in time between 8 and 24 hours after the addition of compound (33) to serum. The release of paclitaxel from compound (35) was slow, as compared to that from compound (33).

Experiment 10

Antitumor assays (2)

A test sample solution was prepared by dissolving compound (33) obtained in Example 9 into physiological saline. Further, a control solution was prepared by dissolving paclitaxel per se into a mixture of ethanol, Cremophore EL (manufactured and sold by Sigma, U.S.A.) and physiological saline. Thus, two types of solutions, namely, one sample solution and one control solution were obtained.

Twenty-one female C57BL/6 mice (six weeks old) were divided into three groups, each consisting of seven mice, and subsequently, B16 melanoma cells were intradermally transplanted to the groin of each of the mice ($5 \times 10^6$ cells per mouse). After eight days from the transplantation, the above-mentioned two types of solutions were administered to the transplanted mice at the tails thereof intravenously so that the mice belonging to the same group received the administration of the same type of solution. The amount of the test sample solution was varied depending on the group of mice. That is, two different doses of compound (33), 20 mg/kg and 50 mg/kg, in terms of paclitaxel, were administered so that the mice belonging to the same group received the administration of the same dose of compound (33). With respect to the control solution, the dose of paclitaxel was 50 mg/kg.

Separately, a group consisting of thirteen mice, which were transplanted with B16 melanoma cells in the same manner as mentioned above, was provided. Each of the mice of such group received the administration of physiological saline, to thereby obtain a non-treated group of mice.

After six days from the administration of the test sample solution, the control solution and the physiological saline to the mice, evaluation was made of the antitumor activity of the compound in terms of the relative average tumor volume (%), namely, the ratio of the average tumor volume of the mice of each of the three treated groups (the mice of the treated groups received the administrations of the test sample solution and the control solution, respectively), relative to the average tumor volume of the mice of the non-treated group (the mice of the non-treated group had received the administration of physiological saline).

The tumor volume was determined as follows. The external major and minor diameters (a and b, respectively) (each in mm) of the tumor were measured and the tumor volume was obtained according to the following formula.

$$V = \frac{a \times b^2}{2} (mm)^3$$

Figure 37:
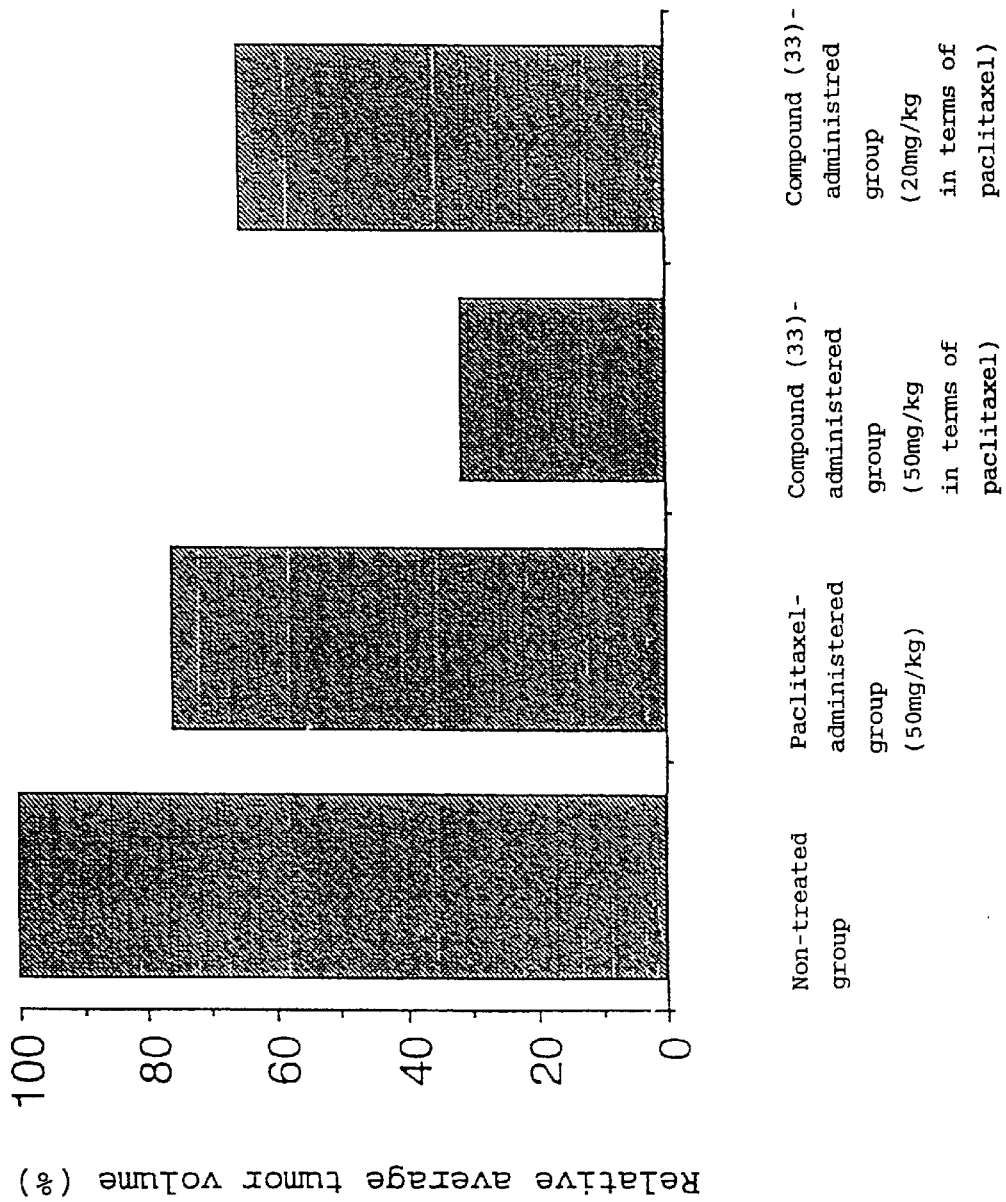
FIG. 37 is a graph showing the results of the antitumor assays conducted in Experiment 10, i.e., the relationship between the doses of compound (33) and the relative average tumor volumes (%) which is measured after six days from the intravenous administration of the test sample solution.

The relationship between the doses of compound (33) and the relative average tumor volume (%) is shown in FIG. 37.

The antitumor activity of compound (33), observed with respect to the group of mice which had received the administration of 50 mg/kg (in terms of paclitaxel) of compound (33), was significantly excellent, as compared to the antitumor activity of paclitaxel, observed with respect to the group of mice which had received the administration of paclitaxel per se.

Experiment 11

Antitumor Assays (3)

A test sample solution was prepared by dissolving compound (33) obtained in Example 9 into physiological saline. Further, a control solution was prepared by dissolving paclitaxel per se into a mixture of ethanol, Cremophore EL (manufactured and sold by Sigma, U.S.A.) and physiological saline. Thus, two types of solutions, namely, one type of test sample solution and one control solution were obtained.

Six female Balb/C mice (six weeks old) were divided into two groups, each consisting of three mice, and subsequently, a 4% suspension of colon 26 tumor cells was intradermally transplanted to the flank of each of the mice. After two days from the transplantation, each of the above-mentioned two types of solutions was individually administered to each of the transplanted mice at the tails thereof intravenously. That is, one group of mice received the administration of the test sample solution, and another group of mice received administration of the control solution. With respect to the test sample solution, the dose of compound (33) was to 50 mg/kg in terms of paclitaxel. With respect to the control solution, the dose of paclitaxel was 50 mg/kg. And every 4 days after the above administration, substantially the same administration was repeated several times.

Separately, a group consisting of five mice, which were transplanted with Colon 26 tumor cells in the same manner as mentioned above, was provided. Each of the mice of such group received the administration of only physiological saline in the same manner as in the case of the administration of the test sample solution, to thereby obtain a non-treated group of mice.

Evaluation was made of the antitumor activity in terms of the change (with the lapse of time) of the average tumor volume (%).

The tumor volume was determined as follows. The external major and minor diameters (a and b, respectively) (each in mm) of the tumor were measured, and the tumor volume was obtained according to the following formula.

$$V = \frac{a \times b^2}{2} (mm)^3$$

Figure 38:
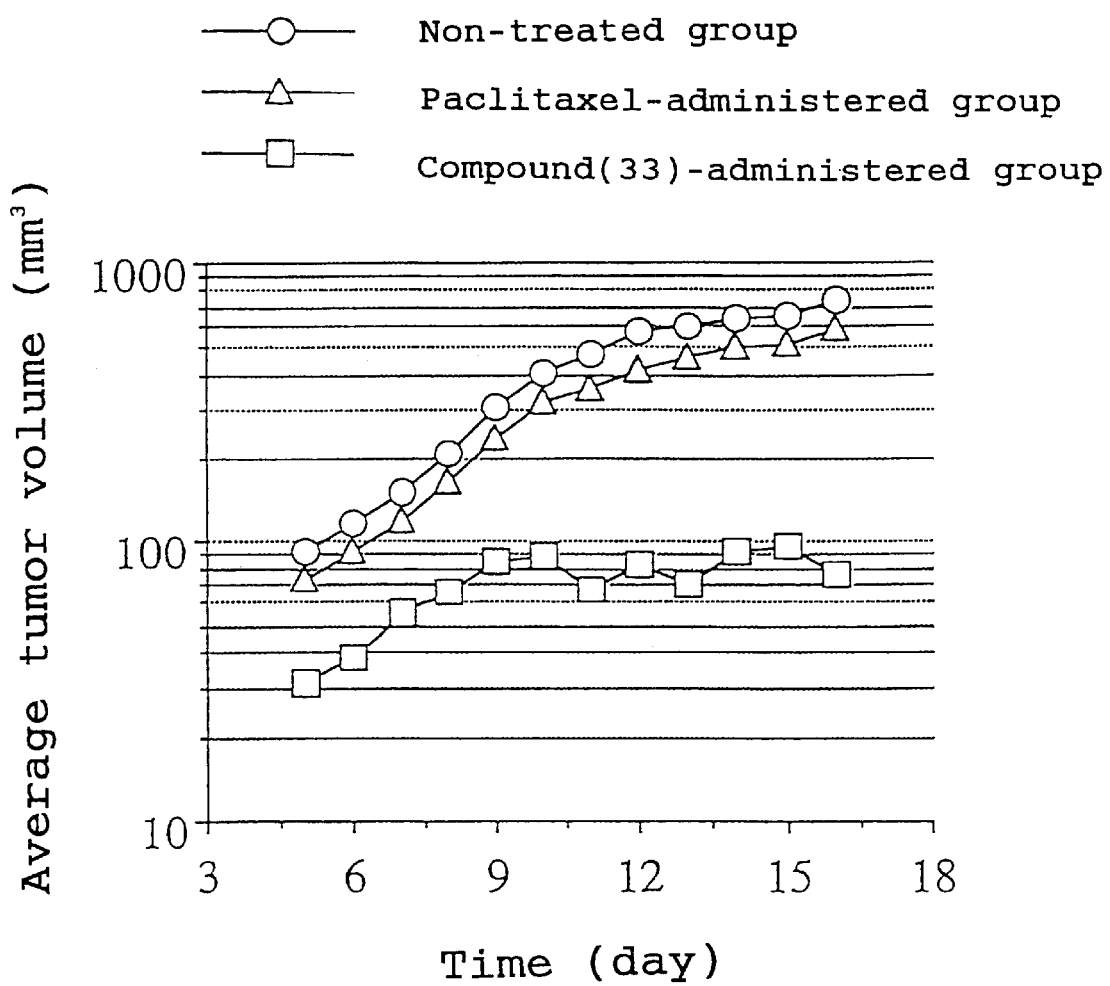
FIG. 38 is a graph showing the results of the antitumor assays conducted in Experiment 11, i.e., the changes (with the lapse of time) in the average tumor volume with respect to mice which had received the administrations of each of the test sample solution, the control solution and the physiological saline.

The changes (with the lapse of time) in average tumor volume of the mice which had received the administrations with respect to each of the test sample solution, the control solution and the physiological saline are shown in FIG. 38.

As is apparent from FIG. 38, the antitumor activity of compound (33), observed with respect to the group of mice which had received the administrations of 50 mg/kg (in terms of paclitaxel) of compound (3), was significantly excellent, as compared to the antitumor activity of paclitaxel, observed with respect to the group of mice which had received the administration of paclitaxel per se.

INDUSTRIAL APPLICABILITY

The drug complex of the present invention is capable of not only surely controlling the rate of the release of a drug therefrom, but also enhancing the transferability of the drug to target tissues and the pharmacological effect of the drug. Therefore, the drug complex of the present invention is extremely valuable in the field of medicine.

For example, when drug complex of the present invention has a structure in which the drug is a taxane compound, the spacer is an amino acid and the carrier is a carboxyalkyldextran, the drug complex is capable of not only surely controlling the rate of release of the taxane compound therefrom, but also exhibiting various advantageous effects, such as an improved solubility in physiological saline, as compared to that of taxane compounds per se. Thus, it becomes possible to administer a taxane compound intravenously without using an adjuvant for dissolving the taxane compound.

What is claimed is:

1. A drug complex of a drug having a hydroxyl group, which is capable of controlling the rate of the release of the drug therefrom in blood, said drug complex comprising:

(A) at least one carrier selected from the group consisting of saccharides each having at least one carboxyl group, polyethylene glycols each having at least one carboxyl group, straight or branched $C_2$–$C_8$ aliphatic carboxylic acids each having at least one carboxyl group, and derivatives thereof each having at least one carboxyl group;

(B) at least one spacer comprised of a compound having at least one amino group and at least one carboxyl group, which is selected from the group consisting of amino acids and peptides, said at least one spacer (B) having a substituent X at the α-position relative to said carboxyl group of said at least one spacer (B); and (C) at least one drug having a hydroxyl group, wherein said at least one drug (C) is bonded to said at least one spacer (B) through an ester bond formed between the hydroxyl group of said drug (C) and the carboxyl group of said spacer (B) to form at least one drug-spacer block, and wherein said at least one drug-spacer block is bonded to said at least one carrier (A) through an amide bond formed between the amino group of said spacer (B) of said at least one drug-spacer block and the carboxyl group of said at least one carrier (A), and wherein, when the hydroxyl group of said at least one drug (C), which is bonded to the carboxyl group of said at least one spacer (B) to form the ester bond, is a primary hydroxyl group, said substituent X has a steric hindrance parameter (Es) value of from –1.0 to –2.5, and when the hydroxyl group of said at least one drug (C), which is bonded to the carboxyl group of said at least one spacer (B) to form the ester bond, is a secondary hydroxyl group, said substituent X has a steric hindrance parameter (Es) value of from –0.0 to –2.5, said Es value being defined by the following formula (1):

$$Es = \log(k_X/k_H) \quad (1)$$

wherein $k_X$ is the reaction rate constant for the acid hydrolysis reaction of an α-monosubstituted acetic acid ester, wherein the acid hydrolysis reaction is represented by the following formula:

$$X\text{—}CH_2COOR^x + H_2O \rightarrow X\text{—}CH_2COOH + R^xOH$$

wherein X is as defined above and $R^x$ is a group selected from the group consisting of $C_1$–$C_8$ alkyl groups and $C_6$–$C_{18}$ aryl groups; and $k_H$ is the reaction rate constant for the acid hydrolysis reaction of an unsubstituted acetic acid ester corresponding to said α-monosubstituted acetic acid ester, wherein the acid hydrolysis reaction is represented by the following formula:

$$CH_3COOR^y + H_2O \rightarrow CH_3COOH + R^yOH$$

wherein $R^y$ has the same meaning as defined for $R^x$;

and wherein said X substituent is selected in relation to said drug to provide an Es value causing dissociation of said ester bond in vivo to occur at a selected and controlled rate.

2. The drug complex according to claim 1, wherein the hydroxyl group of said at least one drug (C), which is bonded to the carboxyl group of said at least one spacer (B) to form the ester bond, is a primary hydroxyl group, and said at least one spacer (B) has a substituent X at the α-position relative to said carboxyl group of said at least one spacer (B), wherein said substituent X has an ES value of from –1.0 to –2.5.

3. The drug complex according to claim 1, wherein the hydroxyl group of said at least one drug (C), which is bonded to the carboxyl group of said at least one spacer (B) to form the ester bond, is a secondary hydroxyl group, and said at least one spacer (B) has a substituent X at the α-position relative to said carboxyl group of said at least one spacer (B), wherein said substituent X has an ES value of from –0.0 to –2.5.

4. The drug complex according to claim 1, wherein said carrier (A) is selected from the group consisting of polysaccharides each having at least one carboxyl group and derivatives thereof each having at least one carboxyl group.

5. The drug complex according to claim 4, wherein said carrier (A) is a carboxyalkyldextran.

6. The drug complex according to claim 1, wherein said at least one carrier (A) is selected from the group consisting of monosaccharides each having at least one carboxyl group and derivatives thereof each having at least one carboxyl group.

7. The drug complex according to claim 1, wherein said at least one spacer (B) is selected from the group consisting of glycine, alanine, leucine, isoleucine and phenylalanine.

8. The drug complex according to claim 1, wherein said at least one drug (C) is selected from the group consisting of taxane compounds.

9. The drug complex according to claim 1, wherein said at least one drug (C) is selected from the group consisting of steroids.

10. A medicine comprising the drug complex of claim 1 in combination with a pharmaceutically acceptable diluent or excipient.

11. A medicine comprising the drug complex of claim 8 in combination with a pharmaceutically acceptable diluent or excipient.

12. A medicine comprising the drug complex of claim 9 in combination with a pharmaceutically acceptable diluent or excipient.

13. A drug complex of a drug having a hydroxyl group, which is capable of controlling the rate of the release of the drug therefrom in blood, said drug complex comprising:
(A) at least one carrier selected from the group consisting of saccharides each having at least one carboxyl group, polyethylene glycols each having at least one carboxyl group, straight or branched $C_2$–$C_8$ aliphatic carboxylic acids each having at least one carboxyl group, and derivatives thereof each having at least one carboxyl group;
(B) at least one spacer comprised of a compound having at least one amino group and at least one carboxyl group, which is selected from the group consisting of amino acids and peptides,
said at least one spacer (B) having a substituent X at the α-position relative to said carboxyl group of said at least one spacer (B); and
(C) at least one drug having a hydroxyl group,
wherein said at least one drug (C) is bonded to said at least one spacer (B) through an ester bond formed between the hydroxyl group of said drug (C) and the carboxyl group of said spacer (B) to form at least one drug-spacer block, and wherein said at least one drug-spacer block is bonded to said at least one carrier (A) through an amide bond formed between the amino group of said spacer (B) of said at least one drug-spacer block and the carboxyl group of said at least one carrier (A), and
wherein, when the hydroxyl group of said at least one drug (C), which is bonded to the carboxyl group of said at least one spacer (B) to form the ester bond, is a primary hydroxyl group, said substituent X has a steric hindrance parameter (Es) value of from –1.0 to –2.5, and when the hydroxyl group of said at least one drug (C), which is bonded to the carboxyl group of said at least one spacer (b) to form the ester bond, is a secondary hydroxyl group, said substituent X has a steric hindrance parameter (Es) value of from –0.0 to –2.5,
said Es value being defined by the following formula (1):

$$Es = \log(k_X/k_H) \quad (1)$$

wherein $k_X$ is the reaction rate constant for the acid hydrolysis reaction of an α-monosubstituted acetic acid ester, wherein the acid hydrolysis reaction is represented by the following formula:

X—CH$_2$COOR$^x$+H$_2$O→X—CH$_2$COOH+R$^x$OH wherein X is as defined above and R$^x$ is a group selected from the group consisting of $C_1$–$C_{18}$ alkyl groups and $C_6$–$C_{18}$ aryl groups; and
$k_H$ is the reaction rate constant for the acid hydrolysis reaction of an unsubstituted acetic acid ester corresponding to said α-monosubstituted acetic acid ester, wherein the acid hydrolysis reaction is represented by the following formula:

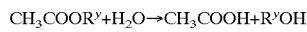

CH$_3$COOR$^y$+H$_2$O→CH$_3$COOH+R$^y$OH wherein R$^y$ has the same meaning as defined for R$^x$, wherein:
said drug (C) is at least one taxane compound represented by the following formula (2):

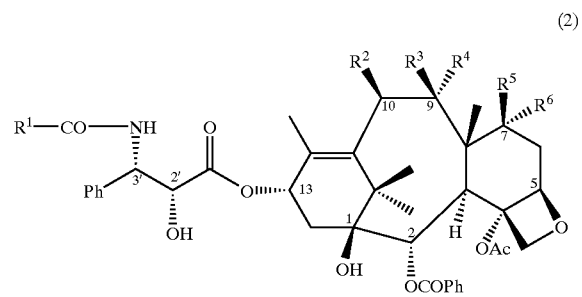

wherein R$^1$ represents a group selected from the group consisting of a straight or branched $C_1$–$C_6$ alkyl group, a straight or branched $C_2$–$C_6$ alkenyl group, a straight or branched $C_2$–$C_6$ alkynyl group, a straight or branched $C_1$–$C_6$ alkoxy group and an unsubstituted or substituted phenyl group; R$^2$ represents a group selected from the group consisting of a hydrogen atom, a hydroxyl group and an acetyloxy group; one of R$^3$ and R$^4$ represents a hydrogen atom and the other represents a hydroxyl group, or R$^3$ and R$^4$ together form an oxo group; one of R$^5$ and R$^6$ represents a hydrogen atom and the other represents a hydroxyl group; Ac represents an acetyl group; and Ph represents a phenyl group,
said at least one taxane compound of formula (2) is bonded, at the 2'- or 7-positioned hydroxyl group thereof, to said at least one spacer (B) at the carboxyl group thereof through the ester bond formed between said hydroxyl group and said carboxyl group,
said carrier (A) is a carboxyalkyldextran represented by the following formula (3):

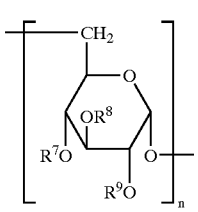

wherein each of R$^7$, R$^8$ and R$^9$ independently represents a hydrogen atom or a carboxylalkyl group selected from the group consisting of —(CH$_2$)$_m$—COOH, —CH(CH$_3$)—COOH, —CH$_2$CH(CH$_3$)—COOH and —CH(CH$_3$)CH$_2$—COOH, wherein m represents an integer of from 1 to 4; and n represents an integer of from 50 to 1000, with the proviso that the ratio of the number of carboxylalkyl groups to the number of n is 0.1 to 2.0, and
said carboxyalkyldextran is bonded, at the carboxyl moiety of at least one of the carboxyalkyl groups thereof, to said at least one spacer (B) at the amino group thereof through the amide bond formed between said amino group and said carboxyl group, and
said at least one spacer (B) has a substituent X at the α-position relative to said carboxyl group of said at least one spacer (B), wherein said substituent X has an ES value of from –0.0 to –2.5.

14. The drug complex according to claim 13, wherein said drug (C) is at least one paclitaxel.

15. The drug complex according to claim 13, wherein said drug (C) is at least one docetaxel.

16. An antitumor medicine, which comprises the drug complex of claim 13 in combination with a pharmaceutically acceptable diluent or excipient.

17. An antitumor medicine, which comprises the drug complex of claim 14 in combination with a pharmaceutically acceptable diluent or excipient.

18. An antitumor medicine, which comprises the drug complex of claim 15 in combination with a pharmaceutically acceptable diluent or excipient.

19. The drug complex according to claim 4, wherein said carrier (A) is a carboxymethyldextran.

20. The drug complex according to claim 1, wherein said at least one spacer (B) is selected from the group consisting of glycylglycylphenylalanylglycine, phenylalanylglycine and glycylphenylalanine.

21. The drug complex according to claim 1, wherein said at least one drug (C) is at least one paclitaxel.

22. The drug complex according to claim 13, wherein:
said at least one taxane compound is at least one paclitaxel,
said at least one spacer (B) is at least one glycylglycylphenylalanylglycine,
said at least one paclitaxel is bonded, at the 2'-positioned hydroxyl group thereof, to said at least one glycylglycylphenylalanylglycine at the carboxyl group thereof through the ester bond formed between said hydroxyl group and said carboxyl group,
said carrier (A) is a carboxymethyldextran,
the molecular weight of said carboxymethyldextran is approximately 150,000 as measured by gel filtration chromatography using 0.1. M NaCl as an eluate, pullulan as a standard and chromatograph including a column for gel filtration, said gel filtration chromatography being conducted under conditions wherein the column is TSKgel G4000PW$_{XL}$ (trade name) (manufactured and sold by Tosoh Corporation, Japan), the flow rate of the eluate is 0.8 ml/min. and the temperature of the column is 40° C. and wherein approximately 50 $\mu$g of said carboxymethyldextran is injected to said chromatograph, and
the amount of said paclitaxel introduced into said carboxymethyldextran is from 1 to 10% by weight, based on the weight of said drug complex.

23. The drug complex according to claim 22, wherein the ratio of the number of carboxyalkyl groups to the number of n is 0.6.

24. A medicine comprising the drug complex of claim 19 in combination with a pharmaceutically acceptable diluent or excipient.

25. A medicine comprising the drug complex of claim 20 in combination with a pharmaceutically acceptable diluent or excipient.

26. A medicine comprising the drug complex of claim 21 in combination with a pharmaceutically acceptable diluent or excipient.

27. An antitumor medicine, which comprises the drug complex of claim 22 in combination with a pharmaceutically acceptable diluent or excipient.

28. An antitumor medicine, which comprises the drug complex of claim 23 in combination with a pharmaceutically acceptable diluent or excipient.

* * * * *